United States Patent [19]
Slade et al.

[11] Patent Number: 5,389,526
[45] Date of Patent: Feb. 14, 1995

[54] PLASMID VECTORS FOR CELLULAR SLIME MOULDS OF THE GENUS DICTYOSTELIUM

[76] Inventors: Martin B. Slade, 40 Conrad Street, East Ryde NSW 2113; Andy C. M. Chang, 7/19 Bowden Street, Harris Park NSW 2150; Keith L. Williams, 25 Kara Street, Lane Cove NSW 2066, all of Australia

[21] Appl. No.: 867,106

[22] PCT Filed: Nov. 2, 1990

[86] PCT No.: PCT/AU90/00530
§ 371 Date: Jun. 25, 1992
§ 102(e) Date: Jun. 25, 1992

[87] PCT Pub. No.: WO91/06644
PCT Pub. Date: May 16, 1991

[30] Foreign Application Priority Data

Nov. 2, 1989 [AU] Australia .................. PJ7187

[51] Int. Cl.$^6$ .............. C12N 1/15; C12N 15/80; C12P 21/00
[52] U.S. Cl. .................. 435/69.1; 435/254.11; 435/320.1; 435/172.3; 435/91.42
[58] Field of Search ............ 530/350; 435/69.1, 254, 435/320.1, 172.3, 254.11, 91.42; 536/23.7; 935/27, 56, 60, 68

[56] References Cited

PUBLICATIONS

Chang, A. C. et al. 1990, *Plasmid* vol. 24 pp. 208–217.
Slade, M. B. et al. 1990, *Plasmid* vol. 24, pp. 195–207.
Ahern, K. G. 1988 *Nucleic Acids Res.* vol. 16 pp. 6825–6837.
Orii, H. et al. 1989, *Nucleic Acids Res.* vol. 17, pp. 1395–1408.
Minghetti, P. P. et al. 1986, *J. Biol. Chem.* vol. 261 pp. 6747–6757.
Skern, T. et al. 1985, *Nucleic Acids Res.* vol. 13 pp. 2111–2126.
Leiting, B. et al. 1988, *Plasmid* vol. 20 pp. 241–248.
Leiting, B. et al. 1990, *Mol. Cell. Biol.* vol. 10 pp. 3727–3736.
Egelhoff, T. T. et al. 1989, *Mol. Cell. Biol.* vol. 9 pp. 1965–1968.
Early, A. E. et al. 1988, *Molec. Cell. Biol.* vol. 8 pp. 3458–3466.
Glenn, D. et al. 1988, *Austral. J. Biotechnol.* vol. 1 pp. 46–57.
Proc. Natl. Acad. Sci. USA, vol. 86, Oct. 1989 Joseph L. Dynes and Richard A. Firtel (Molecular complementation of a genetic marker in *Dictyostelium* using a genomic library) pp. 7966–7970.
Gene, vol. 39 (1985) Wolfgang Nellen & Richard A. Firtel "High Copy Number Transformants & Co. Transformation in *Dictyostelium*", pp. 155–163.
The Embo Journal vol. 2 No. 4 (1983) Metz et al. "Identification of An Endoyenous Plasmid in *Dictyostelium Discoideum*", pp. 515–519.

*Primary Examiner*—Christine M. Nucker
*Assistant Examiner*—Mary E. Mosher
*Attorney, Agent, or Firm*—Woodcock Washburn Kurtz Mackiewicz & Norris

[57] ABSTRACT

The present invention relates generally to the fields of molecular biology and the production of recombinant protein using cellular slime moulds of the genus Dictyostelium. Most particularly, the present invention relates to novel strains of the genus Dictyostelium, recombinant plasmids for use with strains of the genus Dictyostelium, and polypeptides which facilitate the extrachromosomal replication of such plasmids in strains of the genus Dictyostelium. In particular, the present invention provides a polypeptide which facilitates the extrachromosomal replication of a recombinant plasmid in *Dictyostelium spp* in which the recombinant plasmid includes an origin of replication derived from a Ddp2-like plasmid but which lacks functional genes for extrachromosomal replication in wild type *Dictyostelium spp*. The extrachromosomal replicating plasmid constructed in accordance with the present invention are suitable for carrying a wide variety of genes and promoter sequences for control production of recombinant proteins by the biotechnology industry.

20 Claims, 30 Drawing Sheets

FIG. 1-1

```
SalI
TCGACAAATA TCAAGGGTTG GAATCTTGTA AAAATTTTCC CGTTATCGCA
    10         20         30         40         50
              HindIII
AACAATCAAA GTTTAAGCTT CAATCTTCAA TAATAATTTT AACTTTATCT
    60         70         80         90        100
                                              ClaI
CTTTCAATTT TAATAATTTT TTTCAAAAAT TGAAAATGGT ATAGATCGAT
   110        120        130        140        150

AGATCACCTT TTTTAGAGAT AAACCATGAA AAAGACATAA AAAATAAAGG
   160        170        180        190        200

TCATCAAAGT ATTAAAAAAA ATTAATTATC TTTTTAACTT TGAAAAAAAA
   210        220        230        240        250

AAATAAAAAA AAATAAAAAA AAAAAATTCT TTGTTTTAAT AACTTTTAAA
   260        270        280        290        300

ATTATTAAAA ATAGTATAGA TTTAAAGATC ACAATTTTTT ATAATTAACT
   310        320        330        340        350

ACATAAAATT TATAAAAAAT GAGGGTCATG AAGATATATA AATAATTATT
   360        370        380        390        400

TAATTATTAA ATATTTAATT ATTTATTTAA CTTAAAAAAA AAAAAAGGA
   410        420        430        440        450

AAAAAGGAA AAAAAAAGTG AAAAAGGTGG GAAAATGAAA AAAAAAGTGA
   460        470        480        490        500

AAAAAATGCC CAAAAAAATT TTTATATGAG AAAAAAATTA CGTAAAAAAA
   510        520        530        540        550

AAATAAGTCT GACCCAAATC GAAAATAAT AAAAGAGGGG AAAGTAATTA
   560        570        580        590        600

TAACTAGGTT AGTTTTTTAT AATTTTTACA TATTTGTTAA TAACTTTTAA
   610        620        630        640        650
         NdeI
TTTTGAATCA TATGATATTA CATCGTCCCG TTGAAAAAAA AAAAAAAAAT
   660        670        680        690        700

TTTTTTTTCA AACATTTCA TTTTTTAAAA AATGATATAA AATTTTAAAC
   710        720        730        740        750

TAAACTATTT TATTAAATAC AAATATATAA CTTTATCTTA ATCAATTTTT
   760        770        780        790        800
                                          BalII
TTGGTTTATA CATATTTATG TTCGTACTGA AGTATAGATC TTATTACTAA
   810        820        830        840        850

AGTTTCAAAA GTTTTAAAAA AAATTAAAGG GGGTAAATAT ATAACTTTCT
   860        870        880        890        900
```

FIG. 1-2

| | | | | |
|---|---|---|---|---|
| GTTTTTTTCA | ATTCTGTCAT | GACAGAAAGG | TAAAAAGTGT | CATGACAAAA |
| 910 | 920 | 930 | 940 | 950 |
| AAAAAAAAAA | AAAAAATTTA | TTTCTTCAAT | AGGTATTGAA | ATGACCTCCG |
| 960 | 970 | 980 | 990 | 1000 |
| TTTTTAATAA | AAAGTATATA | TTTGTGCTTT | CCTAGATGAA | ATAAGGTTAT |
| 1010 | 1020 | 1030 | 1040 | 1050 |
| TTGAGCTTAA | TTCAGATTAT | TATAAGATTA | TTATAAAAAA | ATGAAAAACT |
| 1060 | 1070 | 1080 | 1090 | 1100 |
| GTCATGACAG | TTTTTGTAAG | TTTCTTATAG | TTTTTTTTAA | TGATCTGAAT |
| 1110 | 1120 | 1130 | 1140 | 1150 |
| HindIII | | XbaI | | |
| TAAGCTTAAA | TAACCTTATT | TCATCTAGAC | GAGCACAAAT | ATATACTTTT |
| 1160 | 1170 | 1180 | 1190 | 1200 |
| TATTAAAAAC | GGAGGTCATT | TCAATACCTA | TTGAAGAAAT | AAATTTTTTT |
| 1210 | 1220 | 1230 | 1240 | 1250 |
| TTTTTTTTTT | TTTGTCATGA | CACTTTTTTT | TTTTGTCAT | GACAGAATTG |
| 1260 | 1270 | 1280 | 1290 | 1300 |
| AAAAAAACAG | AAAGTTATAT | ATTTACCCCC | TTTAATTTTT | TTTAAAACTT |
| 1310 | 1320 | 1330 | 1340 | 1350 |
| | BglII | | | |
| TTGAAACTTT | AGTAATAAGA | TCTATACTTC | AGTACGAACA | TAAATATGTA |
| 1360 | 1370 | 1380 | 1390 | 1400 |
| TAAACCAAAA | AAATTGATTA | AGATAAAGTT | ATATGTTTGT | ATTTAATAAA |
| 1410 | 1420 | 1430 | 1440 | 1450 |
| ATAGTTTAGT | TTAAAATTTT | ATATCATTTT | TTAAAAAATG | AAAATGTTTG |
| 1460 | 1470 | 1480 | 1490 | 1500 |
| | | | | NdeI |
| AAAAAAAAAA | TTTTTTTTTT | TTTTTTCAAC | GGGACGATGT | AATATCATAT |
| 1510 | 1520 | 1530 | 1540 | 1550 |
| GATTCAAAAT | TAAAAGTTAT | TAACAAATAT | GTAAAAATTA | TAAAAAACTA |
| 1560 | 1570 | 1580 | 1590 | 1600 |
| ACCTAGTTAT | AATTACTTTC | CCCTCTTTTT | TTTTTTTTTT | TTTGTCATGA |
| 1610 | 1620 | 1630 | 1640 | 1650 |
| CACTTTTTTT | TTTTGTCAT | GACACTTTTT | TTTTAAAAAA | AAAAAAAAAA |
| 1660 | 1670 | 1680 | 1690 | 1700 |
| ATGTTAAAAT | ACTATTTGAT | GACATTCATT | TTTCCTAGTT | TTTTTTTAGA |
| 1710 | 1720 | 1730 | 1740 | 1750 |
| | | ClaI | | |
| TAGATATAAA | AATAAATTGC | CTATCGATAT | ATACTTAATT | TATTAAGATT |
| 1760 | 1770 | 1780 | 1790 | 1800 |

FIG. 1-3

| | | | | |
|---|---|---|---|---|
| GAATAATATT | TTAATTTTTA | ATAAATTCTA | CTTTTTTTTT | TTTTTTCTTT |
| 1810 | 1820 | 1830 | 1840 | 1850 |

<u>BglII</u>

| | | | | |
|---|---|---|---|---|
| TTTTTTTAAA | TTTTAAAATT | TTTTTTTTTT | ATTAGATCTC | ATAATTAAAA |
| 1860 | 1870 | 1880 | 1890 | 1900 |
| ATCAATTTAA | AATTAAAAGT | TATTTTTAAA | TATGCAAAAA | CTATAAAAAA |
| 1910 | 1920 | 1930 | 1940 | 1950 |
| CTAATGTAGT | TTAACCAACT | TTTTCTATT | TCTTTTTTTT | TTTTTTTTTT |
| 1960 | 1970 | 1980 | 1990 | 2000 |
| TTTTTACTTT | GAAAAAAAAA | AAAAAAAAAA | AAAAAAAAAA | AACCCTCATT |
| 2010 | 2020 | 2030 | 2040 | 2050 |
| ATAAATATTA | ATTACTTTGG | TTTTTTTTGA | TTTTTTTTTT | AATAAATTTA |
| 2060 | 2070 | 2080 | 2090 | 2100 |
| AAATTTTATT | CTCTATCTAA | TTATACCTTA | TTTATAAATA | TTGGAATAAT |
| 2110 | 2120 | 2130 | 2140 | 2150 |
| ATATCAAATA | TTTATCAGTT | TTGGCATGAC | AATTTTAATT | ATATTTATTT |
| 2160 | 2170 | 2180 | 2190 | 2200 |
| TTTGATTAGT | TTTTTTTTTT | TTTTTTTTTT | AAAATTTCTT | TTTTTTTTTT |
| 2210 | 2220 | 2230 | 2240 | 2250 |
| TTTATTTTTA | ATTTTTAATT | TTTATTTTTC | CCACACTTTC | ATTTTATTTT |
| 2260 | 2270 | 2280 | 2290 | 2300 |
| ATTTTATTTA | TTGTAAATTC | ATTTTATTTA | TTTTTAATTA | AATAGTTTTG |
| 2310 | 2320 | 2330 | 2340 | 2350 |

START

| | | | | |
|---|---|---|---|---|
| GTTTAATTTT | ATTCAAAGAT | TTTAAAAATG | GACGAACTTA | TTTCTTGGGA |
| 2360 | 2370 | 2380 | 2390 | 2400 |

<u>EcoRI</u>

| | | | | |
|---|---|---|---|---|
| TAGGTTTTTT | AAGTTTTTTG | TAATACTTTT | GGAAGAATTC | AAAGGTTGTA |
| 2410 | 2420 | 2430 | 2440 | 2450 |
| AAAGAAATGA | TGTGCGTTTG | AGTGTCGATT | ATGACATTCT | TTCTGGTATT |
| 2460 | 2470 | 2480 | 2490 | 2500 |
| TATTCGCCAC | GTACATTTGT | ACTAAAGGAA | GTCTTTAGAG | CAGTGGCCGT |
| 2510 | 2520 | 2530 | 2540 | 2550 |
| CTCTTATGAT | GAATCTGAAA | TAGATTTATT | CAGATTGGGT | TCAGTGTTTC |
| 2560 | 2570 | 2580 | 2590 | 2600 |
| CTGGTACTTC | TTTATATTCA | TATATTCCAG | GTATTTCAG | TTTAAAAGAT |
| 2610 | 2620 | 2630 | 2640 | 2650 |
| TTCCTTTTAA | TTTCAAAAAC | TAAATCGGGT | AAAATAAGAG | TTTCGGATGT |
| 2660 | 2670 | 2680 | 2690 | 2700 |

FIG. 1-4

```
                              BclI
AGATCAAGCA ATATTAATTT TTGATCATTT TTCTAGAATT TCAGATAAAC
    2710       2720       2730       2740       2750

AAGTATTTCG TAAAGATATT ATTCCAGGTT ATAGAACCTT TGAAAAATCA
    2760       2770       2780       2790       2800
                                   PstI
ATATCGAGCG AGTACAAAAT CTCGGATGGT CGTGCTGCAG GAGTGAGTTG
    2810       2820       2830       2840       2850

GTTCAATTTA GTTAGTAAAA TAAGCACTTA TTGTAAAAAT CATCCCTTGT
    2860       2870       2880       2890       2900

TTGCCGAAAA TCCAACATAT AAACATGTGG ATTTTATATC AATGTTATCA
    2910       2920       2930       2940       2950

CTGGTGCATG GAATCATTGT TGATTCCCAA AATGAAGATG AGAATAATGT
    2960       2970       2980       2990       3000

TTCGGCAATG TACTCTCTGA ATCCTTTTGT GGATCTTGAA AAAAGTGATA
    3010       3020       3030       3040       3050

TACCAGGGGC TGTTCAAAGT AGAGTTACTA CAAATAGAAC TAGAGGTTCA
    3060       3070       3080       3090       3100

AGGTCTAATT CCAATTTGAA TAATCCAACA ACAACAACAA CTACTACTAC
    3110       3120       3130       3140       3150

CACTACTACA ACTACCGCAC CAATTACTAC TAGAAGTAAA AGAAAATCTG
    3160       3170       3180       3190       3200
                                             XhoI
ACGACTCTGT ACAAGAACAA AGCTCACGAC AACCAAAAAC CTCGAGAAAG
    3210       3220       3230       3240       3250

TCTGGTTCTC TTAAGGATGT CAGAATTAAC AATATATCAG TAGATTCAAG
    3260       3270       3280       3290       3300

TTCCAGTGAA TCTGATGTGA TTATGTCAGT TTCAAACCGT TTAAAATGTT
    3310       3320       3330       3340       3350

ATCTTTTGGA AGCAGTTGTA AACAAAGGAG AGATCGGTTT AGAAGTCGTC
    3360       3370       3380       3390       3400

AAAGAAGTTT TAAAAGATTT ACAGGACAAA AATTATTCCA CAGGTTTACT
    3410       3420       3430       3440       3450

TGAAAACATT TTCAATCACA ACAAGTCTGA AAGGGTCATA ACACTTTCAA
    3460       3470       3480       3490       3500

GTAGTTTTTT TGAAATTGCT TCAAAAATTA ACTATGATGA AGTTAAGTTC
    3510       3520       3530       3540       3550

AGTGAACTCA GTATTGATGT TCTGGAATCG GCAAAGAGAT TAACATTCGA
    3560       3570       3580       3590       3600
```

FIG. 1-5

| | | | | |
|---|---|---|---|---|
| GAAAAATACA | AATATATTAA | TTCCAACCAA | TAATTTTAAA | GAAGGTTTTG |
| 3610 | 3620 | 3630 | 3640 | 3650 |
| AATTTTTATG | GGTTCCAATT | GTTAATGGTA | TTGCTTCAAC | TTCTGTCTTT |
| 3660 | 3670 | 3680 | 3690 | 3700 |
| GTTTCACCAA | ATAATTATTC | AAGTGGTTCA | TTTGCAAATG | TAGAATCTGC |
| 3710 | 3720 | 3730 | 3740 | 3750 |
| TTTAAAGTTG | ATTCATCTTT | GCATTTCTTT | AGGAAATATA | AATGGTTTCC |
| 3760 | 3770 | 3780 | 3790 | 3800 |
| | | | ClaI | |
| TCTCTATTAG | ATCAATTACA | TTTGATACAT | TTAAATCGAT | TACAAAGGAT |
| 3810 | 3820 | 3830 | 3840 | 3850 |
| CTTATTCCAA | TGTCGAAAAG | AATGCTGGAC | CTTGAACAAG | GCTTCCGAAA |
| 3860 | 3870 | 3880 | 3890 | 3900 |
| ACTTAGAGAT | GCTTGGAATA | ATAGTAATAA | AAAATCCAAA | GTTCAAGATA |
| 3910 | 3920 | 3930 | 3940 | 3950 |
| | ClaI | | EcoRV | |
| GTGATATTAG | TGGCATCGAT | ACAGAGGATA | CAAAGTTGAT | ATCATTTGTC |
| 3960 | 3970 | 3980 | 3990 | 4000 |
| CACGAGTTTA | TAAATGATAA | TTTATATTTA | AAACTATCAA | AAGAAGAAGA |
| 4010 | 4020 | 4030 | 4040 | 4050 |
| | AccI | | | |
| TGGACTAATG | CTAGTAGACT | TTCCAACATC | AACACTTTTT | ATGAGATACA |
| 4060 | 4070 | 4080 | 4090 | 4100 |
| ATCCAAATAG | CATTGATAAC | AAAGTTGGTT | TCATGTTCCA | TTGCCGTTCA |
| 4110 | 4120 | 4130 | 4140 | 4150 |
| GAGATTTCAA | AGTTTCAAAG | TTGTAAAAAC | CACTCGATAG | ATAACCTTGT |
| 4160 | 4170 | 4180 | 4190 | 4200 |
| TTTATCATTT | ACTCCAAATA | ACATTAAAAA | TATATCACAG | GATAATGAAA |
| 4210 | 4220 | 4230 | 4240 | 4250 |
| ATGAGCTTAA | AAAGAAATAT | TCGTTGATGG | TCAGTGATTT | TAGAAATGTT |
| 4260 | 4270 | 4280 | 4290 | 4300 |
| CCAAAGGTGA | CACCAAAATT | TATACCTTCT | GAATTTAAAA | GGTTTACAAT |
| 4310 | 4320 | 4330 | 4340 | 4350 |
| CATTACGTTC | ACAAACAATT | CATACAATGC | CAATAGAGTA | TTTGCGTTTG |
| 4360 | 4370 | 4380 | 4390 | 4400 |
| ACGACATCTC | AAGTGGAATT | TCAATCACAA | ATGTTAAAAA | TATCCACGCA |
| 4410 | 4420 | 4430 | 4440 | 4450 |
| HindII | | | | |
| AAGGGTCAAC | GAAACTTTGA | AATCTACGAA | ACATTACTGG | GAAGTACCAG |
| 4460 | 4470 | 4480 | 4490 | 4500 |

FIG. 1-6

| | | | | |
|---|---|---|---|---|
| GATTATTCGT | GCATTTTTCT | GCGCTCCATG | CTTGATCCAA | ATCAATAATT |
| 4510 | 4520 | 4530 | 4540 | 4550 |
| TTAAATTTGC | CACAGATAAG | TTAATTGATG | ACCAAAGTGT | AAATCACCAG |
| 4560 | 4570 | 4580 | 4590 | 4600 |
| ATTGCATCTT | TGGAAATTAA | AAACTTATCA | TATCTTCCGC | TCGACATCAA |
| 4610 | 4620 | 4630 | 4640 | 4650 |
| GGTTAGAGGT | AGTACAGTTG | GAACGATTAA | GGGTGGAGAG | ACAGCTCCTA |
| 4660 | 4670 | 4680 | 4690 | 4700 |
| TTATTATAAA | CTCAGAAGAA | TTTACGTTTT | CTATCTCATG | CCTTGATATT |
| 4710 | 4720 | 4730 | 4740 | 4750 |
| AGATTTAGTG | CATCCTTAAT | TTCTAAAACA | AAACTAAGCC | AACTTCCAAC |
| 4760 | 4770 | 4780 | 4790 | 4800 |
| ATTTGCTCCA | GATGAAAGGT | ACAATAAAGA | GACTAACATT | TTAAAAGTTT |
| 4810 | 4820 | 4830 | 4840 | 4850 |
| TGGATCAATG | TGATGAACTT | ACTCGAACGT | TTTTAAATAA | CTATAAAATA |
| 4860 | 4870 | 4880 | 4890 | 4900 |
| GCTAATAAAC | TATCAACCAT | TGAAAATTAT | TTATATAATA | ATTTTATGGG |
| 4910 | 4920 | 4930 | 4940 | 4950 |
| ACTAGAAGAT | GAAGATGAAG | ATGAAGATGA | AGATGAAGAT | GAAGATGAAG |
| 4960 | 4970 | 4980 | 4990 | 5000 |
| | | | | STOP |
| ATGAAGATGA | AGATGAAGAT | GAAGACGAAG | ATGGGTATTG | AATTATCATA |
| 5010 | 5020 | 5030 | 5040 | 5050 |
| CTTTAAAAAT | TAATTAAATA | AATAAAAAAA | AAAAAATGAT | TTCAATTTAA |
| 5060 | 5070 | 5080 | 5090 | 5100 |
| ATATATACAT | ATATATATAT | ATAAAATGAG | ATTAATAAAA | CTTTTGAGAC |
| 5110 | 5120 | 5130 | 5140 | 5150 |
| CAACATTTAA | TGAGATTTCT | GATGCTGTTT | ATTTTGCCTG | GAATGAGAGC |
| 5160 | 5170 | 5180 | 5190 | 5200 |
| AAAAGGCTAA | AAAACATGAG | AGAGAATATA | ATAATAAAGG | AAAACTTGGG |
| 5210 | 5220 | 5230 | 5240 | 5250 |
| | | | | ScaI |
| AAAAAGGATC | TAGTATCCAT | TTCCATATTA | ATCCGTGCAG | TACTATTAAT |
| 5260 | 5270 | 5280 | 5290 | 5300 |
| TAAAAAAATA | CTTTAAAAAA | AATTTTAAAA | ACATGGAAAA | TTATATAGAT |
| 5310 | 5320 | 5330 | 5340 | 5350 |
| ClaI | | | | |
| CGATAGATCA | CTAATTTTTA | AAATTAAATA | TATTAAATTT | ATAAAAATTG |
| 5360 | 5370 | 5380 | 5390 | 5400 |

FIG. 1-7

| | | | | |
|---|---|---|---|---|
| AAGTTCATCA | AGATATATAG | ATAATTATTT | AATTATTTGA | ATTTTTAAAA |
| 5410 | 5420 | 5430 | 5440 | 5450 |
| AAAAAAAAAA | AAAAAAAAAA | AAAATCAAAT | ATGTTTATTG | TTTTAAGATT |
| 5460 | 5470 | 5480 | 5490 | 5500 |

<u>ClaI</u>

| | | | | |
|---|---|---|---|---|
| TTTTAATCTC | GTCAATGATT | TTAAAATAAA | AATCGATACA | TAATTTTAAA |
| 5510 | 5520 | 5530 | 5540 | 5550 |
| AAAAACCCTT | TACATTTTTT | ATTTTAATTC | CAAATTTATA | CATTTTTTAT |
| 5560 | 5570 | 5580 | 5590 | 5600 |
| TTTTTTTTTT | TTTTTTTTTT | TTTTTTTTAA | TTTAAATTTT | TTTTTTTTTT |
| 5610 | 5620 | 5630 | 5640 | 5650 |
| TTTTTTTTAT | TTATTTAAAA | TTTAATTATT | AATTTTATAA | ATAAAAAATA |
| 5660 | 5670 | 5680 | 5690 | 5700 |
| GAAATATAAG | TAAAAAAACA | AACAACAAAT | AACATATATA | AAAAAATACA |
| 5710 | 5720 | 5730 | 5740 | 5750 |
| AATAACAAAT | AATTAAATAA | ATTAAATAAC | CATTAAAAAT | GTATATTAAT |
| 5760 | 5770 | 5780 | 5790 | 5800 |

<u>BglII</u>     <u>ScaI</u>

| | | | | |
|---|---|---|---|---|
| AAATTTAAAA | GATCTTTATT | AGTACTATTG | TTACTTTGTA | ATATTCTTCC |
| 5810 | 5820 | 5830 | 5840 | 5850 |

<u>SalI</u>
TG

FIG. 2-1

REP GENE:

```
          2386          2395          2404          2413          2422
ATG GAC GAA CTT ATT TCT TGG GAT AGG TTT TTT AAG TTT TTT GTA
 m   d   e   l   i   s   w   d   r   f   f   k   f   f   v 2431          2440          2449          2458          2467
ATA CTT TTG GAA GAA TTC AAA GGT TGT AAA AGA AAT GAT GTG CGT
 i   l   l   e   e   f   k   g   c   k   r   n   d   v   r 2476          2485          2494          2503          2512
TTG AGT GTC GAT TAT GAC ATT CTT TCT GGT ATT TAT TCG CCA CGT
 l   s   v   d   y   d   i   l   s   g   i   y   s   p   r 2521          2530          2539          2548          2557
ACA TTT GTA CTA AAG GAA GTC TTT AGA GCA GTG GCC GTC TCT TAT
 t   f   v   l   k   e   v   f   r   a   v   a   v   s   y 2566          2575          2584          2593          2602
GAT GAA TCT GAA ATA GAT TTA TTC AGA TTG GGT TCA GTG TTT CCT
 d   e   s   e   i   d   l   f   r   l   g   s   v   f   p 2611          2620          2629          2638          2647
GGT ACT TCT TTA TAT TCA TAT ATT CCA GGT ATT TTC AGT TTA AAA
 g   t   s   l   y   s   y   i   p   g   i   f   s   l   k 2656          2665          2674          2683          2692
GAT TTC CTT TTA ATT TCA AAA ACT AAA TCG GGT AAA ATA AGA GTT
 d   f   l   l   i   s   k   t   k   s   g   k   i   r   v 2701          2710          2719          2728          2737
TCG GAT GTA GAT CAA GCA ATA TTA ATT TTT GAT CAT TTT TCT AGA
 s   d   v   d   q   a   i   l   i   f   d   h   f   s   r 2746          2755          2764          2773          2782
ATT TCA GAT AAA CAA GTA TTT CGT AAA GAT ATT ATT CCA GGT TAT
 i   s   d   k   q   v   f   r   k   d   i   i   p   g   y 2791          2800          2809          2818          2827
AGA ACC TTT GAA AAA TCA ATA TCG AGC GAG TAC AAA ATC TCG GAT
 r   t   f   e   k   s   i   s   s   e   y   k   i   s   d 2836          2845          2854          2863          2872
GGT CGT GCT GCA GGA GTG AGT TGG TTC AAT TTA GTT AGT AAA ATA
 g   r   a   a   g   v   s   w   f   n   l   v   s   k   i 2881          2890          2899          2908          2917
AGC ACT TAT TGT AAA AAT CAT CCC TTG TTT GCC GAA AAT CCA ACA
 s   t   y   c   k   n   h   p   l   f   a   e   n   p   t 2926          2935          2944          2953          2962
TAT AAA CAT GTG GAT TTT ATA TCA ATG TTA TCA CTG GTG CAT GGA
 y   k   h   v   d   f   i   s   m   l   s   l   v   h   g
```

FIG. 2-2

```
        2971        2980        2989        2998        3007
ATC ATT GTT GAT TCC CAA AAT GAA GAT GAG AAT AAT GTT TCG GCA
 i   i   v   d   s   q   n   e   d   e   n   n   v   s   a 3016        3025        3034        3043        3052
ATG TAC TCT CTG AAT CCT TTT GTG GAT CTT GAA AAA AGT GAT ATA
 m   y   s   l   n   p   f   v   d   l   e   k   s   d   i 3061        3070        3079        3088        3097
CCA GGG GCT GTT CAA AGT AGA GTT ACT ACA AAT AGA ACT AGA GGT
 p   g   a   v   q   s   r   v   t   t   n   r   t   r   g 3106        3115        3124        3133        3142
TCA AGG TCT AAT TCC AAT TTG AAT AAT CCA ACA ACA ACA ACA ACT
 s   r   s   n   s   n   l   n   n   p   t   t   t   t   t 3151        3160        3169        3178        3187
ACT ACT ACC ACT ACT ACA ACT ACC GCA CCA ATT ACT ACT AGA AGT
 t   t   t   t   t   t   t   t   a   p   i   t   t   r   s 3196        3205        3214        3223        3232
AAA AGA AAA TCT GAC GAC TCT GTA CAA GAA CAA AGC TCA CGA CAA
 k   r   k   s   d   d   s   v   q   e   q   s   s   r   q 3241        3250        3259        3268        3277
CCA AAA ACC TCG AGA AAG TCT GGT TCT CTT AAG GAT GTC AGA ATT
 p   k   t   s   r   k   s   g   s   l   k   d   v   r   i 3286        3295        3304        3313        3322
AAC AAT ATA TCA GTA GAT TCA AGT TCC AGT GAA TCT GAT GTG ATT
 n   n   i   s   v   d   s   s   s   s   e   s   d   v   i 3331        3340        3349        3358        3367
ATG TCA GTT TCA AAC CGT TTA AAA TGT TAT CTT TTG GAA GCA GTT
 m   s   v   s   n   r   l   k   c   y   l   l   e   a   v 3376        3385        3394        3403        3412
GTA AAC AAA GGA GAG ATC GGT TTA GAA GTC GTC AAA GAA GTT TTA
 v   n   k   g   e   i   g   l   e   v   v   k   e   v   l 3421        3430        3439        3448        3457
AAA GAT TTA CAG GAC AAA AAT TAT TCC ACA GGT TTA CTT GAA AAC
 k   d   l   q   d   k   n   y   s   t   g   l   l   e   n 3466        3475        3484        3493        3502
ATT TTC AAT CAC AAC AAG TCT GAA AGG GTC ATA ACA CTT TCA AGT
 i   f   n   h   n   k   s   e   r   v   i   t   l   s   s 3511        3520        3529        3538        3547
AGT TTT TTT GAA ATT GCT TCA AAA ATT AAC TAT GAT GAA GTT AAG
 s   f   f   e   i   a   s   k   i   n   y   d   e   v   k 3556        3565        3574        3583        3592
TTC AGT GAA CTC AGT ATT GAT GTT CTG GAA TCG GCA AAG AGA TTA
 f   s   e   l   s   i   d   v   l   e   s   a   k   r   l
```

FIG. 2-3

```
         3601        3610        3619        3628        3637
ACA TTC GAG AAA AAT ACA AAT ATA TTA ATT CCA ACC AAT AAT TTT
 t   f   e   k   n   t   n   i   l   i   p   t   n   n   f 3646        3655        3664        3673        3682
AAA GAA GGT TTT GAA TTT TTA TGG GTT CCA ATT GTT AAT GGT ATT
 k   e   g   f   e   f   l   w   v   p   i   v   n   g   i 3691        3700        3709        3718        3727
GCT TCA ACT TCT GTC TTT GTT TCA CCA AAT AAT TAT TCA AGT GGT
 a   s   t   s   v   f   v   s   p   n   n   y   s   s   g 3736        3745        3754        3763        3772
TCA TTT GCA AAT GTA GAA TCT GCT TTA AAG TTG ATT CAT CTT TGC
 s   f   a   n   v   e   s   a   l   k   l   i   h   l   c 3781        3790        3799        3808        3817
ATT TCT TTA GGA AAT ATA AAT GGT TTC CTC TCT ATT AGA TCA ATT
 i   s   l   g   n   i   n   g   f   l   s   i   r   s   i 3826        3835        3844        3853        3862
ACA TTT GAT ACA TTT AAA TCG ATT ACA AAG GAT CTT ATT CCA ATG
 t   f   d   t   f   k   s   i   t   k   d   l   i   p   m 3871        3880        3889        3898        3907
TCG AAA AGA ATG CTG GAC CTT GAA CAA GGC TTC CGA AAA CTT AGA
 s   k   r   m   l   d   l   e   q   g   f   r   k   l   r 3916        3925        3934        3943        3952
GAT GCT TGG AAT AAT AGT AAT AAA AAA TCC AAA GTT CAA GAT AGT
 d   a   w   n   n   s   n   k   k   s   k   v   q   d   s 3961        3970        3979        3988        3997
GAT ATT AGT GGC ATC GAT ACA GAG GAT ACA AAG TTG ATA TCA TTT
 d   i   s   g   i   d   t   e   d   t   k   l   i   s   f 4006        4015        4024        4033        4042
GTC CAC GAG TTT ATA AAT GAT AAT TTA TAT TTA AAA CTA TCA AAA
 v   h   e   f   i   n   d   n   l   y   l   k   l   s   k 4051        4060        4069        4078        4087
GAA GAA GAT GGA CTA ATG CTA GTA GAC TTT CCA ACA TCA ACA CTT
 e   e   d   g   l   m   l   v   d   f   p   t   s   t   l 4096        4105        4114        4123        4132
TTT ATG AGA TAC AAT CCA AAT AGC ATT GAT AAC AAA GTT GGT TTC
 f   m   r   y   n   p   n   s   i   d   n   k   v   g   f 4141        4150        4159        4168        4177
ATG TTC CAT TGC CGT TCA GAG ATT TCA AAG TTT CAA AGT TGT AAA
 m   f   h   c   r   s   e   i   s   k   f   q   s   c   k 4186        4195        4204        4213        4222
AAC CAC TCG ATA GAT AAC CTT GTT TTA TCA TTT ACT CCA AAT AAC
 n   h   s   i   d   n   l   v   l   s   f   t   p   n   n
```

FIG. 2-4

```
           4231            4240            4249            4258            4267
ATT AAA AAT ATA TCA CAG GAT AAT GAA AAT GAG CTT AAA AAG AAA
 i   k   n   i   s   q   d   n   e   n   e   l   k   k   k 4276            4285            4294            4303            4312
TAT TCG TTG ATG GTC AGT GAT TTT AGA AAT GTT CCA AAG GTG ACA
 y   s   l   m   v   s   d   f   r   n   v   p   k   v   t 4321            4330            4339            4348            4357
CCA AAA TTT ATA CCT TCT GAA TTT AAA AGG TTT ACA ATC ATT ACG
 p   k   f   i   p   s   e   f   k   r   f   t   i   i   t 4366            4375            4384            4393            4402
TTC ACA AAC AAT TCA TAC AAT GCC AAT AGA GTA TTT GCG TTT GAC
 f   t   n   n   s   y   n   a   n   r   v   f   a   f   d 4411            4420            4429            4438            4447
GAC ATC TCA AGT GGA ATT TCA ATC ACA AAT GTT AAA AAT ATC CAC
 d   i   s   s   g   i   s   i   t   n   v   k   n   i   h 4456            4465            4474            4483            4492
GCA AAG GGT CAA CGA AAC TTT GAA ATC TAC GAA ACA TTA CTG GGA
 a   k   g   q   r   n   f   e   i   y   e   t   l   l   g 4501            4510            4519            4528            4537
AGT ACC AGG ATT ATT CGT GCA TTT TTC TGC GCT CCA TGC TTG ATC
 s   t   r   i   i   r   a   f   f   c   a   p   c   l   i 4546            4555            4564            4573            4582
CAA ATC AAT AAT TTT AAA TTT GCC ACA GAT AAG TTA ATT GAT GAC
 q   i   n   n   f   k   f   a   t   d   k   l   i   d   d 4591            4600            4609            4618            4627
CAA AGT GTA AAT CAC CAG ATT GCA TCT TTG GAA ATT AAA AAC TTA
 q   s   v   n   h   q   i   a   s   l   e   i   k   n   l 4636            4645            4654            4663            4672
TCA TAT CTT CCG CTC GAC ATC AAG GTT AGA GGT AGT ACA GTT GGA
 s   y   l   p   l   d   i   k   v   r   g   s   t   v   g 4681            4690            4699            4708            4717
ACG ATT AAG GGT GGA GAG ACA GCT CCT ATT ATT ATA AAC TCA GAA
 t   i   k   g   g   e   t   a   p   i   i   i   n   s   e 4726            4735            4744            4753            4762
GAA TTT ACG TTT TCT ATC TCA TGC CTT GAT ATT AGA TTT AGT GCA
 e   f   t   f   s   i   s   c   l   d   i   r   f   s   a 4771            4780            4789            4798            4807
TCC TTA ATT TCT AAA ACA AAA CTA AGC CAA CTT CCA ACA TTT GCT
 s   l   i   s   k   t   k   l   s   q   l   p   t   f   a 4816            4825            4834            4843            4852
CCA GAT GAA AGG TAC AAT AAA GAG ACT AAC ATT TTA AAA GTT TTG
 p   d   e   r   y   n   k   e   t   n   i   l   k   v   l
```

FIG. 2-5

```
      4861          4870          4879          4888          4897
GAT CAA TGT GAT GAA CTT ACT CGA ACG TTT TTA AAT AAC TAT AAA
 d   q   c   d   e   l   t   r   t   f   l   n   n   y   k 4906          4915          4924          4933          4942
ATA GCT AAT AAA CTA TCA ACC ATT GAA AAT TAT TTA TAT AAT AAT
 i   a   n   k   l   s   t   i   e   n   y   l   y   n   n 4951          4960          4969          4978          4987
TTT ATG GGA CTA GAA GAT GAA GAT GAA GAT GAA GAT GAA GAT GAA
 f   m   g   l   e   d   e   d   e   d   e   d   e   d   e 4996          5005          5014          5023          5032
GAT GAA GAT GAA GAT GAA GAT GAA GAT GAA GAT GAA GAC GAA GAT
 d   e   d   e   d   e   d   e   d   e   d   e   d   e   d

GGG TAT
 g   y
```

FIG.10-1

```
ClaI      10         20         30         40         50
     CGATAGGTGG CACTTTTCGG GGAAATGTGC GCGGAACCCC TATTTGTTTA 60         70         80         90        100
     TTTTTCTAAA TACATTCAAA TATGTATCCG CTCATGAGAC AATAACCCTG 110        120        130        140        150
     ATAAATGCTT CAATAATATT GAAAAGGAA GAGTATGAGT ATTCAACATT 160        170        180        190        200
     TCCGTGTCGC CCTTATTCCC TTTTTGCGG CATTTGCCT TCCTGTTTTT 210        220        230        240        250
     GCTCACCCAG AAACGCTGGT GAAAGTAAAA GATGCTGAAG ATCAGTTGGG 260        270        280        290        300
     TGCACGAGTG GGTTACATCG AACTGGATCT CAACAGCGGT AAGATCCTTG 310        320        330        340        350
     AGAGTTTTCG CCCCGAAGAA CGTTTTCCAA TGATGAGCAC TTTTAAAGTT 360        370        380        390        400
     CTGCTATGTG GCGCGGTATT ATCCCGTATT GACGCCGGGC AAGAGCAACT 410        420        430        440 ScaI  450
     CGGTCGCCGC ATACACTATT CTCAGAATGA CTTGGTTGAG TACTCACCAG 460        470        480        490        500
     TCACAGAAAA GCATCTTACG GATGGCATGA CAGTAAGAGA ATTATGCAGT 510        520        530        540        550
     GCTGCCATAA CCATGAGTGA TAACACTGCG GCCAACTTAC TTCTGACAAC 560        570        580        590        600
     GATCGGAGGA CCGAAGGAGC TAACCGCTTT TTTGCACAAC ATGGGGGATC 610        620        630        640        650
     ATGTAACTCG CCTTGATCGT TGGGAACCGG AGCTGAATGA AGCCATACCA 660        670        680        690        700
     AACGACGAGC GTGACACCAC GATGCCTGTA GCAATGCCAA CAACGTTGCG 710        720        730        740        750
     CAAACTATTA ACTGGCGAAC TACTTACTCT AGCTTCCCGG CAACAATTAA 760        770        780        790        800
     TAGACTGGAT GGAGGCGGAT AAAGTTGCAG GACCACTTCT GCGCTCGGCC 810        820        830        840        850
     CTTCCGGCTG GCTGGTTTAT TGCTGATAAA TCTGGAGCCG GTGAGCGTGG 860        870        880        890        900
     GTCTCGCGGT ATCATTGCAG CACTGGGGCC AGATGGTAAG CCCTCCCGTA
```

FIG.10-2

```
          910        920        930        940        950
     TCGTAGTTAT CTACACGACG GGGAGTCAGG CAACTATGGA TGAACGAAAT 960        970        980        990       1000
     AGACAGATCG CTGAGATAGG TGCCTCACTG ATTAAGCATT GGTAACTGTC 1010       1020       1030       1040       1050
     AGACCAAGTT TACTCATATA TACTTTAGAT TGATTTAAAA CTTCATTTTT 1060       1070       1080       1090       1100
     AATTTAAAAG GATCTAGGTG AAGATCCTTT TTGATAATCT CATGACCAAA 1110       1120       1130       1140       1150
     ATCCCTTAAC GTGAGTTTTC GTTCCACTGA GCGTCAGACC CCGTAGAAAA 1160       1170       1180       1190       1200
     GATCAAAGGA TCTTCTTGAG ATCCTTTTTT TCTGCGCGTA ATCTGCTGCT 1210       1220       1230       1240       1250
     TGCAAACAAA AAAACCACCG CTACCAGCGG TGGTTTGTTT GCCGGATCAA 1260       1270       1280       1290       1300
     GAGCTACCAA CTCTTTTTCC GAAGGTAACT GGCTTCAGCA GAGCGCAGAT 1310       1320       1330       1340       1350
     ACCAAATACT GTCCTTCTAG TGTAGCCGTA GTTAGGCCAC CACTTCAAGA 1360       1370       1380       1390       1400
     ACTCTGTAGC ACCGCCTACA TACCTCGCTC TGCTAATCCT GTTACCAGTG 1410       1420       1430       1440       1450
     GCTGCTGCCA GTGGCGATAA GTCGTGTCTT ACCGGGTTGG ACTCAAGACG 1460       1470       1480       1490       1500
     ATAGTTACCG GATAAGGCGC AGCGGTCGGG CTGAACGGGG GGTTCGTGCA 1510       1520       1530       1540       1550
     CACAGCCCAG CTTGGAGCGA ACGACCTACA CCGAACTGAG ATACCTACAG 1560       1570       1580       1590       1600
     CGTGAGCTAT GAGAAAGCGC CACGCTTCCC GAAGGGAGAA AGGCGGACAG 1610       1620       1630       1640       1650
     GTATCCGGTA AGCGGCAGGG TCGGAACAGG AGAGCGCACG AGGGAGCTTC 1660       1670       1680       1690       1700
     CAGGGGGAAA CGCCTGGTAT CTTTATAGTC CTGTCGGGTT TCGCCACCTC 1710       1720       1730       1740       1750
     TGACTTGAGC GTCGATTTTT GTGATGCTCG TCAGGGGGGC GGAGCCTATC 1760       1770       1780       1790       1800
     GAAAACGCC AGCAACGCGG CCTTTTTACG GTTCCTGGCC TTTTGCTGGC
```

FIG.10-3

```
      1810        BamHI    1830          1840          1850
CTTTTGCTGG  CCTTTGGATC  CGCTAGACGA  GCACAAATAT  ATACTTTTTA 1860          1870          1880          1890          1900
TTAAAAACGG  AGGTCATTTC  AATACCTATT  GAAGAAATAA  ATTTTTTTTT 1910          1920          1930          1940          1950
TTTTTTTTTT  TGTCATGACA  CTTTTTTTTT  TTTGTCATGA  CAGAATTGAA 1960          1970          1980          1990          2000
AAAAACAGAA  AGTTATATAT  TTACCCCCTT  TAATTTTTTT  TAAAACTTTT

2010        BglII    2030          2040          2050
GAAACTTTAG  TAATAAGATC  TATACTTCAG  TACGAACATA  AATATGTATA 2060          2070          2080          2090          2100
AACCAAAAAA  ATTGATTAAG  ATAAAGTTAT  ATGTTTGTAT  TTAATAAAAT 2110          2120          2130          2140          2150
AGTTTAGTTT  AAAATTTTAT  ATCATTTTTT  AAAAAATGAA  AATGTTTGAA 2160          2170          2180          2190        NdeI2200
AAAAAAAATT  TTTTTTTTTT  TTTCAACGG  GACGATGTAA  TATCATATGA 2210          2220          2230          2240          2250
TTCAAAATTA  AAAGTTATTA  ACAAATATGT  AAAAATTATA  AAAAACTAAC 2260          2270          2280          2290          2300
CTAGTTATAA  TTACTTTCCC  CTCTTTTTTT  TTTTTTTTTT  TGTCATGACA 2310          2320          2330          2340          2350
CTTTTTTTTT  TTTGTCATGA  CACTTTTTTT  TTAAAAAAAA  AAAAAAAAAT 2360          2370          2380          2390          2400
GTTAAAATAC  TATTTGATGA  CATTCATTTT  TCCTAGTTTT  TTTTTAGATA 2410          2420  ClaI
GATATAAAAA  TAAATTGCCT  AT
```

FIG.15-1

```
ClaI     10           20          30          40          50
CGATAGGTGG  CACTTTTCGG  GGAAATGTGC  GCGGAACCCC  TATTTGTTTA 60           70          80          90         100
TTTTTCTAAA  TACATTCAAA  TATGTATCCG  CTCATGAGAC  AATAACCCTG 110          120         130         140         150
ATAAATGCTT  CAATAATATT  GAAAAGGAA  GAGTATGAGT  ATTCAACATT 160          170         180         190         200
TCCGTGTCGC  CCTTATTCCC  TTTTTGCGG   CATTTGCCT   TCCTGTTTTT 210          220         230         240         250
GCTCACCCAG  AAACGCTGGT  GAAAGTAAAA  GATGCTGAAG  ATCAGTTGGG 260          270         280         290         300
TGCACGAGTG  GGTTACATCG  AACTGGATCT  CAACAGCGGT  AAGATCCTTG 310          320         330         340         350
AGAGTTTTCG  CCCCGAAGAA  CGTTTTCCAA  TGATGAGCAC  TTTTAAAGTT 360          370         380         390         400
CTGCTATGTG  GCGCGGTATT  ATCCCGTATT  GACGCCGGGC  AAGAGCAACT 410          420         430         440 ScaI    450
CGGTCGCCGC  ATACACTATT  CTCAGAATGA  CTTGGTTGAG  TACTCACCAG 460          470         480         490         500
TCACAGAAAA  GCATCTTACG  GATGGCATGA  CAGTAAGAGA  ATTATGCAGT 510          520         530         540         550
GCTGCCATAA  CCATGAGTGA  TAACACTGCG  GCCAACTTAC  TTCTGACAAC 560          570         580         590         600
GATCGGAGGA  CCGAAGGAGC  TAACCGCTTT  TTTGCACAAC  ATGGGGGATC 610          620         630         640         650
ATGTAACTCG  CCTTGATCGT  TGGGAACCGG  AGCTGAATGA  AGCCATACCA 660          670         680         690         700
AACGACGAGC  GTGACACCAC  GATGCCTGTA  GCAATGCCAA  CAACGTTGCG 710          720         730         740         750
CAAACTATTA  ACTGGCGAAC  TACTTACTCT  AGCTTCCCGG  CAACAATTAA 760          770         780         790         800
TAGACTGGAT  GGAGGCGGAT  AAAGTTGCAG  GACCACTTCT  GCGCTCGGCC 810          820         830         840         850
CTTCCGGCTG  GCTGGTTTAT  TGCTGATAAA  TCTGGAGCCG  GTGAGCGTGG 860          870         880         890         900
GTCTCGCGGT  ATCATTGCAG  CACTGGGGCC  AGATGGTAAG  CCCTCCCGTA
```

FIG.15-2

```
            910        920        930        940        950
       TCGTAGTTAT CTACACGACG GGGAGTCAGG CAACTATGGA TGAACGAAAT 960        970        980        990       1000
       AGACAGATCG CTGAGATAGG TGCCTCACTG ATTAAGCATT GGTAACTGTC 1010       1020       1030       1040       1050
       AGACCAAGTT TACTCATATA TACTTTAGAT TGATTTAAAA CTTCATTTTT 1060       1070       1080       1090       1100
       AATTTAAAAG GATCTAGGTG AAGATCCTTT TTGATAATCT CATGACCAAA 1110       1120       1130       1140       1150
       ATCCCTTAAC GTGAGTTTTC GTTCCACTGA GCGTCAGACC CCGTAGAAAA 1160       1170       1180       1190       1200
       GATCAAAGGA TCTTCTTGAG ATCCTTTTTT TCTGCGCGTA ATCTGCTGCT 1210       1220       1230       1240       1250
       TGCAAACAAA AAAACCACCG CTACCAGCGG TGGTTTGTTT GCCGGATCAA 1260       1270       1280       1290       1300
       GAGCTACCAA CTCTTTTTCC GAAGGTAACT GGCTTCAGCA GAGCGCAGAT 1310       1320       1330       1340       1350
       ACCAAATACT GTCCTTCTAG TGTAGCCGTA GTTAGGCCAC CACTTCAAGA 1360       1370       1380       1390       1400
       ACTCTGTAGC ACCGCCTACA TACCTCGCTC TGCTAATCCT GTTACCAGTG 1410       1420       1430       1440       1450
       GCTGCTGCCA GTGGCGATAA GTCGTGTCTT ACCGGGTTGG ACTCAAGACG 1460       1470       1480       1490       1500
       ATAGTTACCG GATAAGGCGC AGCGGTCGGG CTGAACGGGG GGTTCGTGCA 1510       1520       1530       1540       1550
       CACAGCCCAG CTTGGAGCGA ACGACCTACA CCGAACTGAG ATACCTACAG 1560       1570       1580       1590       1600
       CGTGAGCTAT GAGAAAGCGC CACGCTTCCC GAAGGGAGAA AGGCGGACAG 1610       1620       1630       1640       1650
       GTATCCGGTA AGCGGCAGGG TCGGAACAGG AGAGCGCACG AGGGAGCTTC 1660       1670       1680       1690       1700
       CAGGGGGAAA CGCCTGGTAT CTTTATAGTC CTGTCGGGTT TCGCCACCTC 1710       1720       1730       1740       1750
       TGACTTGAGC GTCGATTTTT GTGATGCTCG TCAGGGGGGC GGAGCCTATC 1760       1770       1780       1790       1800
       GAAAAACGCC AGCAACGCGG CCTTTTTACG GTTCCTGGCC TTTTGCTGGC
```

FIG. 15-3

```
         1810       1820       1830       1840       1850
    CTTTTGCTGG CCTTTGGATC TACAAATTAA TTAATCCCAT CAAATCTTTA 1860       1870       1880       1890       1900
    AAAAAAAAAA TGGTTTAAAA AAACTTGGGT TGGTTAATTA TTATTTGAAA 1910       1920       1930       1940       1950
    ATTTTAAAAC CCAAATTAAA AAAAAAAAAT GGGATTCAAA AATTTTTTTT 1960       1970       1980       1990       2000
    TTTTTTTTTT TTTTTTTTTT TTTTTTTTTT TTTTTTTTCA GATTGCATAA 2010       2020       2030       2040       2050
    AAAGATTTTT TTTTTTTTTT TTTCTTATTT CTTAAAACAA ATAAATTAAA

2060       START      2080       2090       2100
    TTAAATAAAA AATAAAAATG AAATTCCAAC ATACATTTAT TGCATTATTA 2110       2120 NsiI  HindIII  2140       2150
    TCACTATTAA CATACGCCAA TGCATATGAA AGCTTGCATG CCTGCAGGTC 2160      SmaI KpnI   2180       2190       2200
    GACTCTAGAG GATCCCCGGG TACCTAAATC ATGAATGAAA GTGCTTCACA 2210       2220       2230       2240       2250
    TAAAAATAAT AATAATAATA TAACAATAAT AATATTTAAA TGTATAATAA 2260       2270       2280       2290       2300
    AATTTAATTA CTTTTTTTTT AATGGTTGTT GATCTTTATC CGACCTTAAA 2310       2320       2330       2340       2350
    AAAAAAAAAA TAAAACCAAT AGGCTATTGG TTTTTTTTTT AATTGTTTTT 2360       2370       2380       2390       2400
    TTATTTTTA  TTATTACTTT AATTATCATT TTTTAAATTA CAAAAAAAAT 2410       2420       2430       2440       2450
    TAAAAATCCA GATATTAAGG TATTTGCACT AGTGCTTTAA CGTTAAAATT 2460       2470       2480       2490       2500
    TGAAAAAAAA AAAAAATTAA TAATTTTACC CTTTATGGGT AAACGATTCT 2510       2520       2530       2540       2550
    CACATATAAT .ACAATCTCCA TGAAAAGATC CGCTAGACGA GCACAAATAT 2560       2570       2580       2590       2600
    ATACTTTTTA TTAAAAACGG AGGTCATTTC AATACCTATT GAAGAAATAA 2610       2620       2630       2640       2650
    ATTTTTTTTT TTTTTTTTTT TGTCATGACA CTTTTTTTTT TTTGTCATGA 2660       2670       2680       2690       2700
    CAGAATTGAA AAAAACAGAA AGTTATATAT TTACCCCCTT TAATTTTTTT
```

FIG. 15-4

```
        2710       2720      ClaI  2740       2750
   TAAAACTTTT GAAACTTTAG TAATAAGATC GATCTATACT TCAGTACGAA 2760       2770       2780       2790       2800
   CATAAATATG TATAAACCAA AAAAATTGAT TAAGATAAAG TTATATGTTT 2810       2820       2830       2840       2850
   GTATTTAATA AAATAGTTTA GTTAAAATT TTATATCATT TTTTAAAAAA 2860       2870       2880       2890       2900
   TGAAAATGTT TGAAAAAAAA AATTTTTTTT TTTTTTTCA ACGGGACGAT 2910       2920       2930       2940       2950
   GTAATATCAT ATATGATTCA AAATTAAAAG TTATTAACAA ATATGTAAAA 2960       2970       2980       2990       3000
   ATTATAAAAA ACTAACCTAG TTATAATTAC TTTCCCTCT TTTTTTTTTT 3010       3020       3030       3040       3050
   TTTTTTTGTC ATGACACTTT TTTTTTTTTG TCATGACACT TTTTTTTTAA 3060       3070       3080       3090       3100
   AAAAAAAAAA AAAAATGTTA AAATACTATT TGATGACATT CATTTTCCT 3110       3120       3130
   AGTTTTTTTT TAGATAGATA TAAAAATAAA TTGCCTAT
```

PLASMID VECTORS FOR CELLULAR SLIME MOULDS OF THE GENUS DICTYOSTELIUM

FIELD OF THE INVENTION

The present invention relates generally to the fields of molecular biology and the production of recombinant proteins by the biotechnology industry. More particularly, the present invention relates to novel strains of the genus Dictyostelium, recombinant plasmid vectors for use with strains of the genus Dictyostelium, and polypeptides which facilitate the extrachromosomal replication of such plasmids in strains of the genus Dictyostelium. Such extrachromosomally replicating plasmids, constructed with the art disclosed in this invention, are suitable for carrying a wide variety of genes and promoter sequences for the controlled production of recombinant proteins by the biotechnology industry.

BACKGROUND ART

As is well known in the art, genetic information is encoded on double stranded DNA molecules according to the sequence of four nucleotides containing different bases, adenine (A), thymine (T), cytosine (C) and guanine (G). Blocks of DNA sequences flanking genes often control gene activity by binding regulatory proteins and acting as recognition signals for enzymes of the cells biosynthetic machinery. Thus each cell contains a web of regulatory molecules which, by binding to specific DNA sequences, control gene activity. Other DNA sequences have crucial functions related to the control of DNA synthesis and partitioning of DNA into separate cells during cell division. These functions must be present on every DNA molecule in every cell or the DNA will be lost within a few cell generations.

Plasmids are usually circular DNA molecules possessing DNA sequences allowing them to replicate independently from chromosomal DNA. The DNA sequence block where the replication of plasmid DNA is initiated is commonly called the "origin of replication" and the ability to replicate independently from chromosomal DNA is referred to as "extrachromosomal" replication.

Molecular biologists have developed techniques for cutting DNA molecules into fragments using sequence specific restriction enzymes, purifying the fragments and rejoining them in a different order. If one of the fragments of DNA used contains an origin of replication from an E. coli plasmid, the DNA can be inserted (transformed) into E. coli where it will replicate as a plasmid and can be produced in relatively large quantities. These techniques mean that genes from one organism, for example a human gene, can be flanked by regulatory DNA sequences from another organism, for example the bacterium E. coli, causing the human gene to be active in E. coli under entirely different regulatory controls. If the plasmid in question is constructed to include a second origin of replication allowing replication in a separate host cell, for example a mouse cell line, the gene can easily be transferred to the second host cell. Such a plasmid containing origins of replication for more than one host is commonly called a "shuttle vector". Plasmids are usually constructed to contain selectable markers, which are usually genes that confer antibiotic resistance or a metabolic advantage on the host cell to allow cells containing the plasmid to be distinguished from cells that have not received any plasmid during the transformation. Selectable marker genes must be flanked by appropriate DNA sequences to permit gene activity in the required host cell. It is possible to insert a plasmid into a host cell where it will be unable to replicate and so the only cells that survive the selection procedure will be those with the plasmid inserted into the host's chromosomal DNA. Such a plasmid without an appropriate origin of replication is called an "integrating plasmid".

A cell produces polypeptides and proteins by initially making a messenger RNA copy of the gene, a process called transcription which is under the control of the flanking DNA sequences as summarised above. The cellular biosynthetic machinery then reads (translates) the RNA sequence in three nucleotide groups called codons which specify the amino acids to be incorporated into the polypeptide chain. The genetic code and mechanism of protein synthesis is very similar in all organisms so molecular biology techniques can be used to construct plasmid vectors to produce recombinant proteins in many different host cells irrespective of the source of the original gene. However, different host cells may process the protein in different ways so it may, for example, be folded incorrectly or cleaved by protease enzymes. Most importantly, eukaryotic cells differ from bacteria by frequently linking further chemical structures onto their proteins, a process called "post-translational modification". The chemical structures linked to eukaryotic proteins may include several types of oligosaccharide chains, glycolipids, lipids, sulphate and phosphate groups, all of which may affect the physical and biological properties of the molecule. Common effects of these post-translational modifications include increased resistance to proteolysis, altered immunogenicity, altered in vivo clearance and uptake by different cell types.

Post-translational modifications frequently occur on proteins that are secreted from cells or are present on cell membranes. Such proteins include a wide variety of soluble proteins that mediate inter-cellular interactions, blood proteins and cell surface receptors and so are of considerable interest to the pharmaceutical industry as either the targets for drug research or for in vivo administration as therapeutic drugs in their own right. Since post-translational modifications may substantially alter the biological activity of such proteins (for example, tissue plasminogen activator (Ezzell, 1988, Nature 333, 383)), it is a goal of the biotechnology industry to produce each protein with a range of different modifications, both those that occur naturally and new modifications such as truncated oligosaccharide chains. However, proteins with post-translational modifications can only be produced in eukaryotic hosts and only a few eukaryotes have been used industrially. Mammalian tissue culture, for example Chinese Hamster Ovary Cells, is usually able to produce proteins with post-translational modifications similar to the natural protein, but is very expensive since these cells frequently require serum components in their growth media, have a slow growth rate and are relatively difficult to grow in large fermentors. Consequently, simple eukaryotes such as insect cells infected with baculovirus or yeast cells have been used to produce proteins with some post-translational modifications at a considerably lower cost. However, no one host is suitable for all recombinant proteins or can produce more than a few of the wide range of desirable post-translational modifications.

Dictyostelium has some advantages as a host for the production of low cost recombinant proteins with post-translational modifications (reviewed by Glenn & Williams, 1988, Australian J. Biotech. 1(4), 46–56). These include the production of N-linked gycosylation indistinguishable from the mammalian "high mannose form" and a wide variety of other structures including phosphatidyl-inositol-glycan tails. It is possible to alter the post-translational modifications produced by Dictyostelium by either using a range of mutant cultures which produce altered glycan structures or by simply harvesting the Dictyostelium cells at different stages of the life cycle. A considerable body of scientific literature is available on the culture and genetics of Dictyostelium (Spudich J. Ed. (1987) Methods in Cell Biology Vol. 28, Academic Press, London). Dictyostelium has a number of characteristics suitable for use in the production of recombinant proteins in fermenters since they grow rapidly (4–10 hour cell cycle) and reach high densities (around 50 million cells per ml) in a nutrient medium. For some purposes, the ability of Dictyostelium to grow on a lawn of bacteria on a simple nutrient medium provides a remarkably simple and cheap culture technique when compared with mammalian or event insect tissue culture.

Dictyostelium strains are known to posses at least thirteen different plasmids (Farrat & Williams (1988) Trends in Genetics 4, 343–348), but only Ddp1, Ddp2 and pDG1 have been studied in detail. Plasmid pDG1 is very unstable when cloned in *E. coli* (Orii et al (1989) Nucleic Acids Research 17, 1395–1408) so most constructions of shuttle vectors have used sequences from either Ddp1 or Ddp2. Plasmid Ddp1 is 12.3 Kb in size, but Ahern et al (Nucleic Acids Research (1988) 16, 6825–6837) showed that a vector containing a selectable marker (G418) resistance and only 2.2 Kb of Ddp1 was able to replicate extrachromosomally in *D. discoideum*. However, but the copy number per cell of this truncated plasmids lowered from the 150 characteristic of the parent plasmid to only 10–15 copies per cell. It is probable that this low copy number plasmid may not segregate efficiently at cell division and so may be unstable in the absence of continuous selection with the antibiotic G418. Incorporation of additional Dictyostelium DNA into such plasmids based on the Ddp1 origin of replication prevents them being maintained extrachromosomally (Gurniak et al, (1990) Current Genetics 17, 321–325.) so they are unsuitable for use in the biotechnology industry.

The practical application of plasmids constructed from sections of Ddp2 has been limited by technical difficulties. The majority of techniques used in molecular biology are designed for use in the bacterium *E. coli* so the manipulation of Dictyostelium DNA requires it to be cloned into a vector capable of replication in *E. coli*. Consequently, research on Ddp2 has concentrated on the construction of recombinant "shuttle vectors" containing sequences allowing replication in both *E. coli* and *Dictyostelium spp*. Plasmid pMUW111 illustrates a shuttle vector that the present inventors have constructed (FIG. 4), which contains a 4.139 Kb Hind III—ScaI restriction fragment of Ddp2. This is close to the minimum amount of Ddp2 which can maintain extrachromosomal replication in wild type strains of Dictyostelium. Leiting and Noegel (1988 Plasmid 20, 241–248) have used a similar 4.0 Kb fragment of Ddp2 with approximately 300 bp deleted close to the Xho I restriction site to construct a 9.6 Kb shuttle vector called pnDe1. However, despite containing minimal sections for the extrachromosomal replication of Ddp2, both these shuttle vectors (pMUW111 and pn DE1) suffer from problems of instability when maintained in *E. coli*. This is consistent with the Ddp2 DNA containing sequences that are unstable in *E. coli*. This problem can be mitigated by the use of host strains which lack exo-nuclease I and have low plasmid copy number (e.g. strain CES 201), but such hosts frequently present problems in preparing sufficient plasmid DNA for gene cloning experiments and for transforming back into Dictyostelium.

The necessity of using pieces of Ddp2 DNA approximately 4 Kb long to construct shuttle vectors also raises problems with regard to the final size of the plasmid. The shuttle vector must contain selectable markers for both hosts together with appropriate promoter and termination sequences. These sequences comprise nearly 50% of the size of plasmids pMUW111 and pnDe1. In addition, to be of any practical use a shuttle vector must be capable of carrying additional DNA containing a gene to be expressed in Dictyostelium together with appropriate controlling sequences. These additional sequences are likely to amount to a minimum of at least 2 Kb of DNA, bringing the total plasmid size to around 12 kilobase pairs. Increasing the size of the plasmid to over 10 Kb decreases its stability, a factor of considerable importance for the commercial production of recombinant proteins where, in order to avoid contamination of the product, regulatory authorities do not permit the use the antibiotic selection to ensure plasmid maintenance while cells are grown for extended periods. A large plasmid also raises difficulties since fewer restriction enzymes will cut the plasmid at only one position, the most suitable sites for genetic manipulations.

Shuttle vectors capable of being easily manipulated in *E. coli* and transferred back into *Dictyostelium spp.* are an essential pre-requisite for realising the potential of Dictyostelium in biotechnology. The present inventors have discovered means by which such vectors containing sections of Ddp2 smaller than 4 Kb can be constructed.

The present inventors have elucidated the full nucleotide sequence of the plasmid Ddp2 and have determined that a portion of this sequence encodes a gene designated Rep. The present inventors have shown that the presence of a polypeptide encoded by the Rep gene is essential for extrachromosomal replication of the Ddp2 plasmid.

DISCLOSURE OF THE INVENTION

Accordingly, in a first aspect the present invention consists in a polypeptide which facilitates the extrachromosomal replication of a recombinant plasmid in *Dictyostelium Spp*, the recombinant plasmid including an origin of replication derived from a Ddp2-like plasmid, but lacking functional genes for extrachromosomal replication in wild type *Dictyostelium Spp*.

In a preferred embodiment of this aspect of the present invention the recombinant plasmid includes an origin of replication derived from plasmid Ddp2.

In a preferred embodiment of this aspect of the present invention the polypeptide has an amino acid sequence substantially as shown in FIG. 2 (SEQ ID NO: 3).

In a further preferred embodiment of this aspect of the present invention the polypeptide is encoded by a DNA sequence substantially as shown in FIG. 1 (SEQ ID NO: 2) from nucleotide 2378 to nucleotide 5038.

As used herein the phrase "Ddp2-like plasmid" is intended to cover plasmids having similar structure and similar functional regions to plasmid Ddp2. One example of such a Ddp2-like plasmid is plasmid pDG1.

In a second aspect the present invention consists in a recombinant plasmid vector, said vector being characterised in that it includes an origin of replication derived from plasmid Ddp2 or plasmid pDG1 and that it lacks functional genes for extrachromosomal replication in wild type Dictyostelium.

In a third aspect the present invention consists in a recombinant plasmid vector containing a DNA sequence substantially as shown in FIG. 1 (SEQ ID NO: 2) from nucleotide 1 to nucleotide 2436 or a subsection thereof, and lacking functional genes for extrachromosomal replication in wild type *Dictyostelium spp.*

In a fourth aspect the present invention consists in a recombinant plasmid vector containing a DNA sequence substantially as shown in FIG. 1 (SEQ ID NO: 2) from nucleotide 1153 to nucleotide 1775 or a subsection thereof, and lacking functional genes for extrachromosomal replication in wild type *Dictyostelium spp.*

In a fifth aspect the present invention consists in a recombinant plasmid vector containing the DNA sequence TGTCATGACA (SEQ ID NO: 1) but lacking functional genes for extrachromosomal replication in wild type *Dictyostelium spp.*

In a sixth aspect the present invention consists in a recombinant plasmid vector containing a DNA sequence substantially as shown in FIG. 1 (SEQ ID NO: 2) from nucleotide 1 to nucleotide 3241 or a portion thereof and lacking functional genes for extrachromosomal replication in wild type *Dictyostelium spp.*

It is presently preferred that the recombinant plasmid vector includes a heterologous DNA sequence(s) encoding a desired polypeptide, a promoter sequence(s) that controls the expression of the heterologous DNA sequence(s), and preferably a sequence(s) including a selectable marker.

In a preferred embodiment of the present invention the recombinant plasmid vector includes a DNA sequence encoding a polypeptide and regulatory sequences for secretion of the desired polypeptide.

In a further preferred embodiment of the present invention the recombinant plasmid vector includes an expression cassette comprising a promoter DNA sequence derived from the Dictyostelium Actin 15 gene, a DNA sequence encoding the secretion signal peptide sequence of the D19 gene which encodes the protein PsA and a DNA sequence for RNA polyadenylation signal derived from the Actin 15 gene.

In a further preferred embodiment of the present invention, the recombinant vector includes the sequence of plasmid pMUW102, plasmid pMUW130 or plasmid pMUW1530 and a heterologous DNA sequence encoding a desired polypeptide together with DNA sequences enabling the expression of the sequence encoding the desired polypeptide.

In a seventh aspect, the present invention consists in a recombinant strain of Dictyostelium, the recombinant strain being characterised in that the strain includes a gene encoding a polypeptide which facilitates the extrachromosomal replication of a recombinant plasmid, the recombinant plasmid including an origin or replication derived from plasmid Ddp2 but lacking the functional gene for extrachromosomal replication in wild type Dictyostelium.

In a preferred embodiment of the present invention the recombinant plasmid includes an origin of replication derived from plasmid Ddp2, and is more preferably the recombinant plasmid of one of the second to sixth aspects of the present invention.

The gene encoding the polypeptide which facilitates the extrachromosomal replication of the recombinant plasmid may be present in a chromosome of the recombinant strain of Dictyostelium or carried on a second plasmid, the second plasmid lacking an origin of replication derived from Ddp2. It is, however, presently preferred that the gene encoding the polypeptide is carried on a chromosome.

It is presently preferred that the recombinant strain of Dictyostelium has included within a chromosome the Rep. gene.

In a further preferred embodiment of the present invention the chromosome of the recombinant strain of Dictyostelium includes a sequence substantially as shown in FIG. 1 (SEQ ID NO: 2) from nucleotide 1885 to nucleotide 5292.

In a further preferred embodiment of the present invention the recombinant strain of Dictyostelium harbors a recombinant plasmid, the recombinant plasmid including an origin of replication derived from plasmid Ddp2 or plasmid pDG1, and preferably a DNA sequence encoding a desired polypeptide together with a DNA sequence enabling the expression of the sequence encoding the desired polypeptide, but lacking functional genes for extrachromosomal replication in wild type Dictyostelium.

In an eighth aspect the present invention consists in a method of producing a desired polypeptide comprising the following steps:
1. Transforming a recombinant strain of Dictyostelium with a recombinant plasmid vector including a DNA sequence encoding the desired polypeptide and sequences enabling the expression of the DNA sequence encoding the desired polypeptide;
2. Culturing the recombinant strain of Dictyostelium under conditions which allow the expression of the DNA sequence encoding the desired polypeptide and allowing the desired polypeptide to be produced either as a cell bound form or be secreted; and
3. Recovering the secreted desired polypeptide; characterised in that the recombinant plasmid vector includes an origin of replication derived from plasmid Ddp2 but lacks the functional genes for extrachromosomal replication in wild type Dictyostelium; and
that the recombinant strain of Dictyostelium includes a gene encoding a polypeptide which facilitates the extrachromosomal replication of the recombinant plasmid.

As used herein the phrase "cell bound form" is intended to cover proteins either internal to the cell or present on the cell membrane.

In a preferred embodiment of this aspect of the present invention the gene encoding the polypeptide which facilitates the extrachromosomal replication of the recombinant plasmid is present in a chromosome of the recombinant strain. Alternatively the gene is carried on a second recombinant plasmid present in the recombinant strain.

In a ninth aspect the present invention consists in a DNA molecule which includes a nucleotide sequence which encodes a polypeptide and which is capable of transforming Dictyostelium strains such that recombinant plasmid vectors which include an origin of replication derived from a Ddp2-like plasmid, preferably plasmid Ddp2, are incapable of extrachromosomal replication in wild type *Dictyostelium spp.* are capable of extrachromosomal replication in the transformed Dictyostelium strain.

In a preferred embodiment of this aspect of the present invention the DNA molecule includes a sequence substantially as shown in FIG. 1 (SEQ ID NO: 2) from nucleotide 2378 to nucleotide 5038, or part thereof.

As stated above, the present invention relates to the construction of extrachromosomal plasmid vectors for Dictyostelium using much smaller sections of the plasmid Ddp2 than has previously been possible. The present invention enables the construction of plasmid vectors containing an origin of replication derived from Ddp2 which can be encoded on a section of Ddp2 DNA of less than 3.0 Kb, but omit sections of Ddp2 DNA that contain genes for polypeptides essential for replication and preferably DNA sequences that are unstable when cloned in *E. coli*. The replication of such plasmids can be achieved by maintaining them in recombinant strains of Dictyostelium where the polypeptides required for plasmid replication are provided by genes inserted into the chromosomal DNA of the host cell or alternatively into another compatible plasmid vector. The present invention enables the production of a wide range of plasmid vectors which may be constructed using the techniques known in the art and disclosed herein, including plasmids designed for the expression of recombinant protein products in *Dictyostelium spp.*

The present invention further comprises the use of these recombinant Dictyostelium strains for the maintenance of recombinant plasmids containing an origin of replication derived from Ddp2 but lacking functional genes for replication proteins. The maintenance of recombinant plasmids in hosts that have been genetically modified to supply polypeptides necessary for plasmid replication is likely to be a crucial factor in the production of recombinant proteins using *Dictyostelium spp.*

SHORT DESCRIPTION OF THE DRAWINGS

In order that the nature of the present invention may be more clearly understood preferred forms thereof will now be described with reference to the following examples and accompanying figures, in which:

FIG. 1 (SEQ ID NO: 2) is the nucleotide sequence of the Dictyostelium plasmid Ddp2. The sequence of one strand of DNA is shown, numbered clockwise from the SalI restriction enzyme site. The position of the recognition sites of restriction enzymes SalI, HindIII, BglII, NdeI, ClaI, EcoRI, EcoRV, PstI, BclI, XbaI, XhoI, AccI, HindII and ScaI are indicated. START and STOP indicates the position of the first and last codons of the Rep gene respective.

KEY: A=Adenine. C=Cytosine. G=Guanine. T=Thymine;

FIG. 2 is the amino acid sequence (SEQ ID NO: 3) of the polypeptide encoded by the Rep gene as derived from the DNA sequence of plasmid Ddp2. The nucleotide sequence of the coding strand of the Rep gene, numbered clockwise from the cleavage site of the SalI restriction enzyme, is aligned with the amino acid sequence predicted from the standard genetic code.

KEY:
A = Adenine.
C = Cytosine.
G = Guanine.
T = Thymine.
a = Alanine.
c = Cysteine.
d = Aspartic acid.
e = Glutamic acid.
f = Phenylalanine.
g = Glycine.
h = Histidine.
i = Isoleucine.
k = Lysine.
l = Leucine.
m = Methionine.
n = Asparagine.
p = Proline.
q = Asparagine.
r = Arginine.
s = Serine.
t = Threonine.
v = Valine.
w = Tryptophan;

FIG. 10 is the nucleotide sequence (SEQ ID NO: 5) of the shuttle vector pMUW1530. The sequence of one strand of DNA is shown, numbered anti-clockwise from the ClaI restriction enzyme site. The position of the recognition sites of restriction enzymes ClaI, ScaI, BamHI, BglII and NdeI are indicated.

Figure 11:
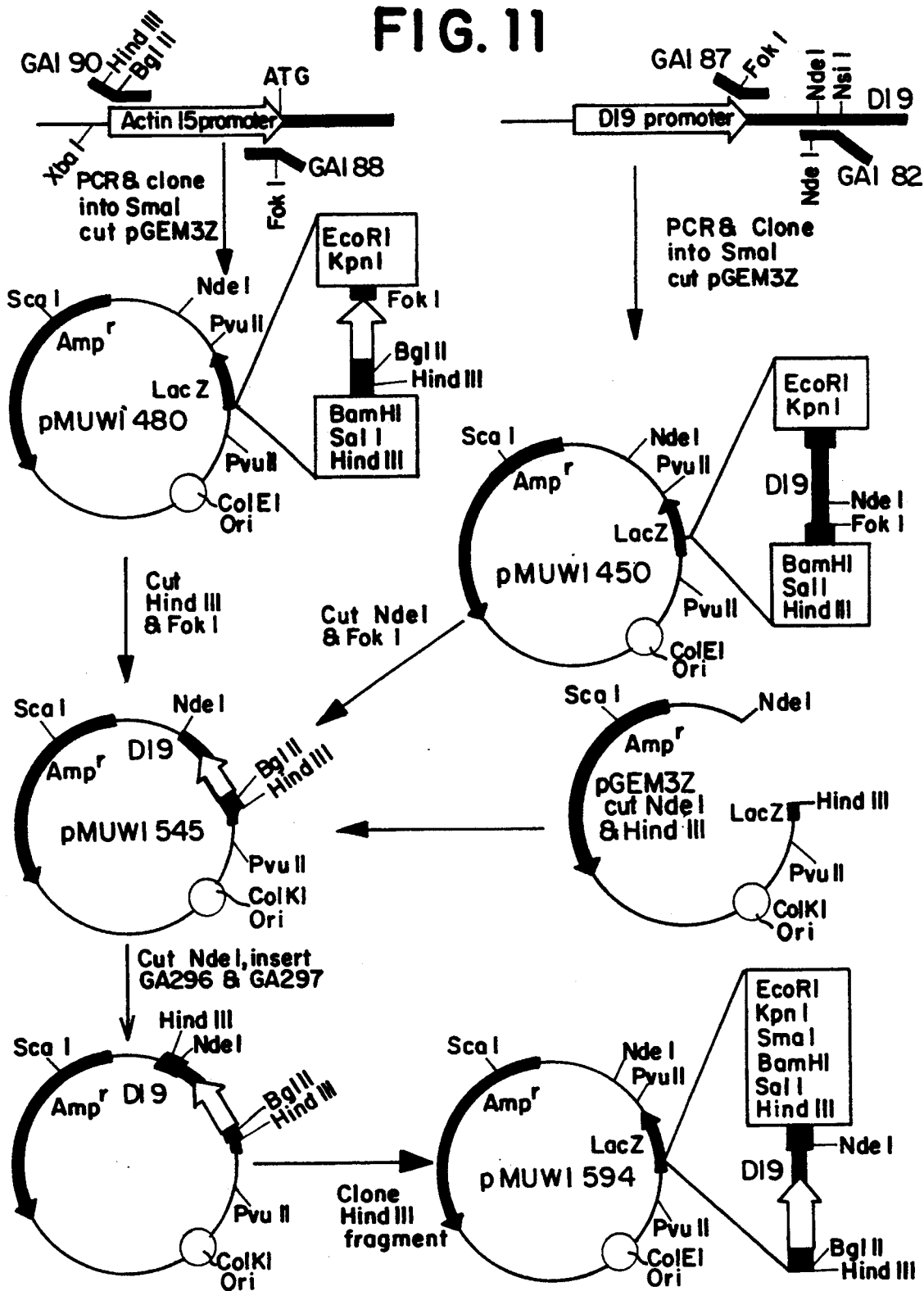
Figure 12:
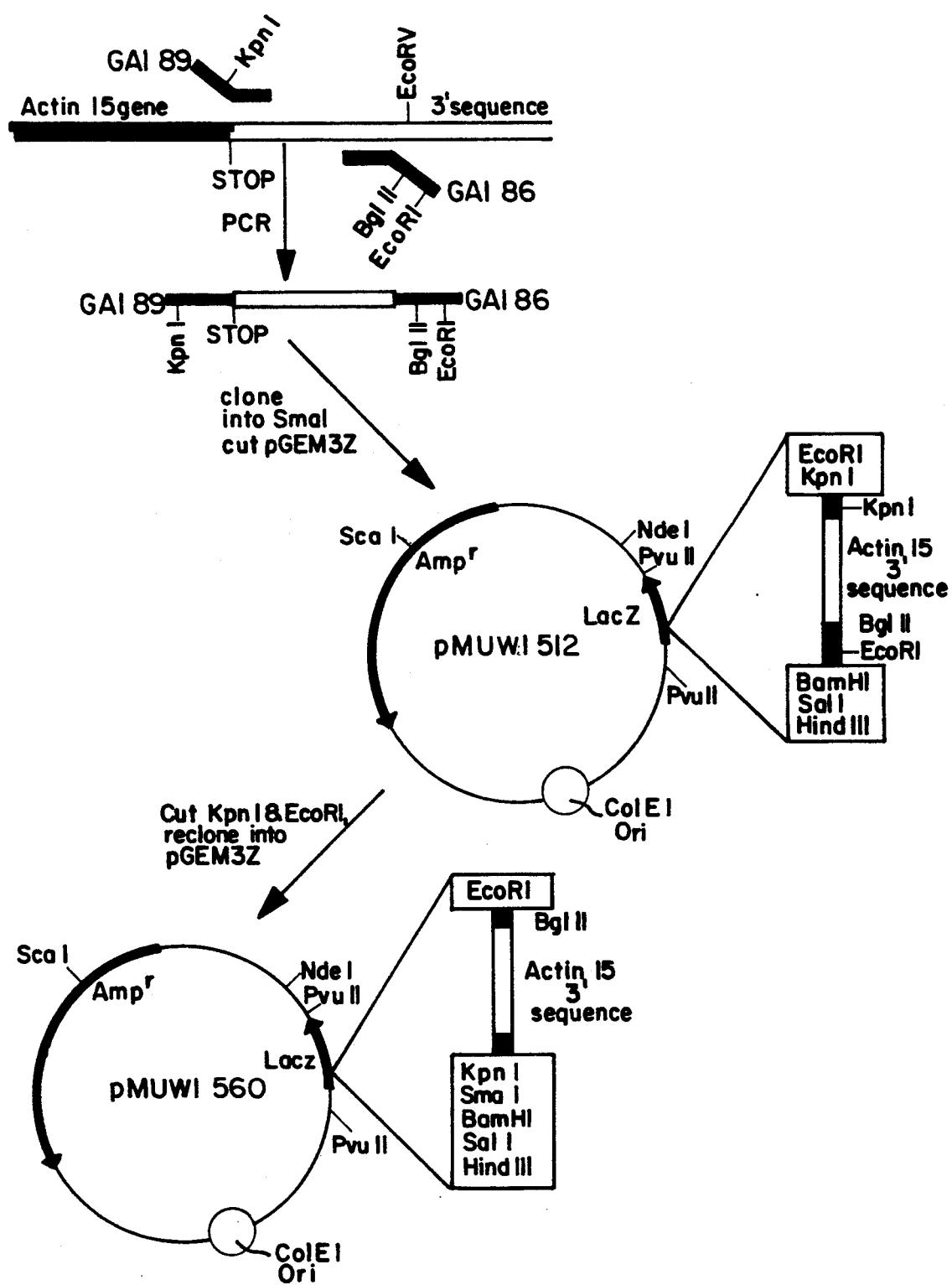
Figure 13:
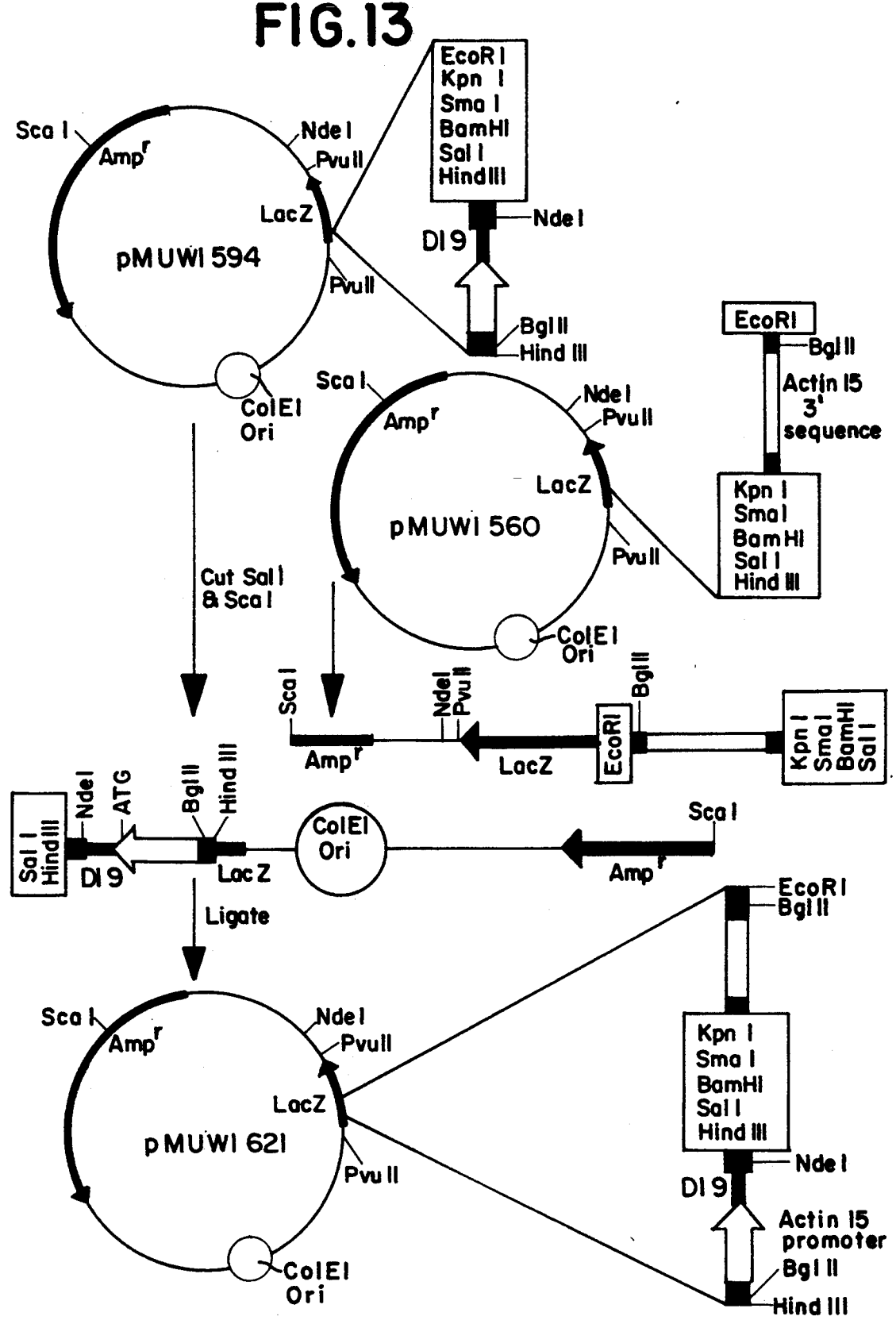
Figure 14:
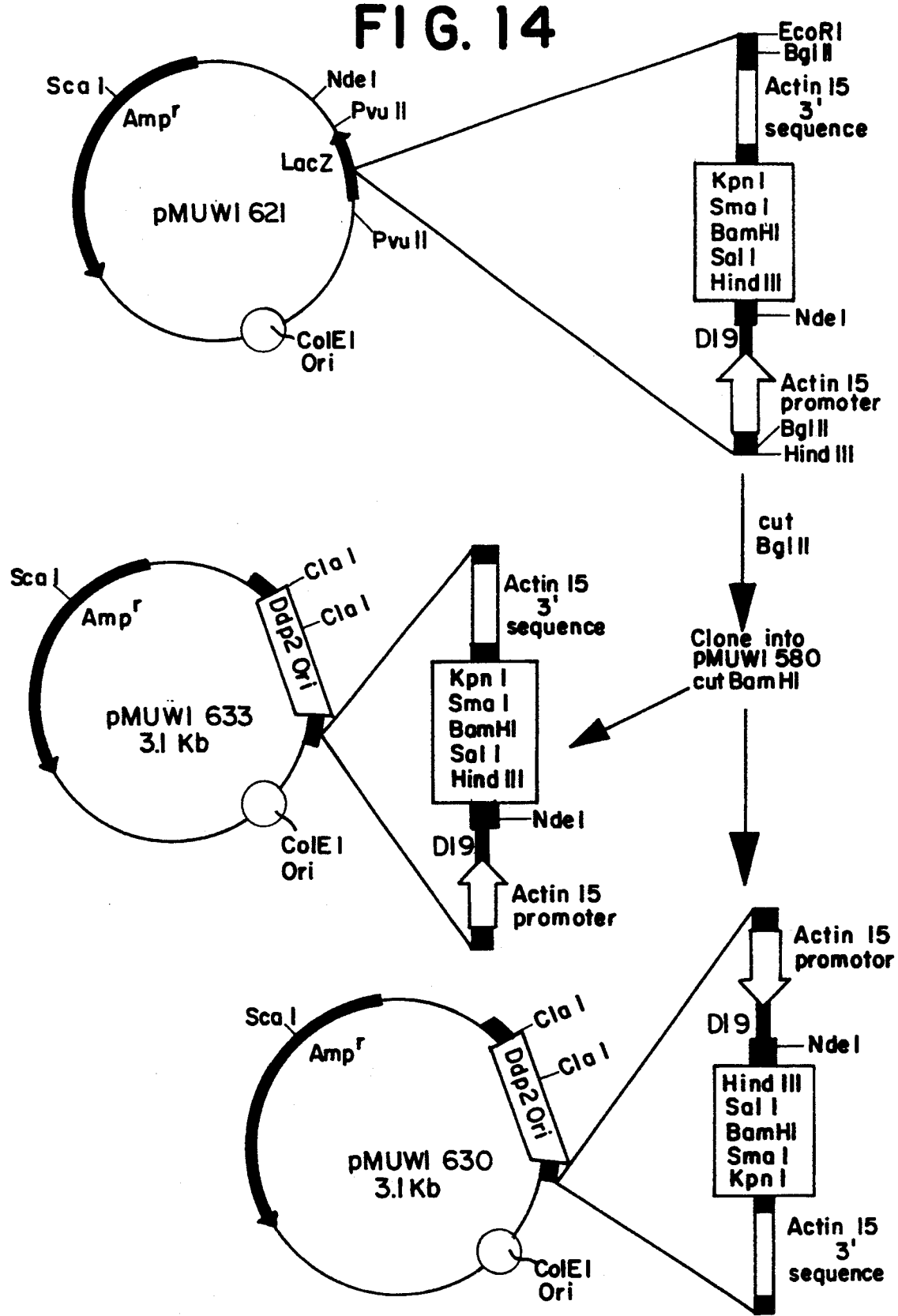

KEY: A=Adenine. C=Cytosine. G=Guanine. T=Thymine;

FIG. 11 is a schematic representation of the construction of the promoter and secretion signal sequence sections of an expression cassette in plasmid pMUW1594;

FIG. 12 is a schematic representation of the cloning of the polyadenylation sequence from the Dictyostelium Actin 15 gene into plasmid pMUW1560;

FIG. 13 is a schematic representation of the construction of the expression cassette in pMUW1621;

FIG. 14 is a schematic representation of the construction of an expression vectors pMUW1630 and pMUW1633 by insertion of the expression cassette into the shuttle vector pMUW1580; and FIG. 15 is the nucleotide sequence (SEQ ID NO: 4) of the expression vector pMUW1630. The sequence of one strand of DNA is shown, numbered anti-clockwise from the ClaI restriction enzyme site. The position of the recognition sites of restriction enzymes ClaI, ScaI, NsiI, HindIII, SmaI and KpnI are indicated. START indicates the position of the first codon of secretion signal peptide in the expression cassette.

KEY: A=Adenine. C=Cytosine. G=Guanine. T=Thymine.

BEST MODE OF CARRYING OUT THE INVENTION

Figure 3:
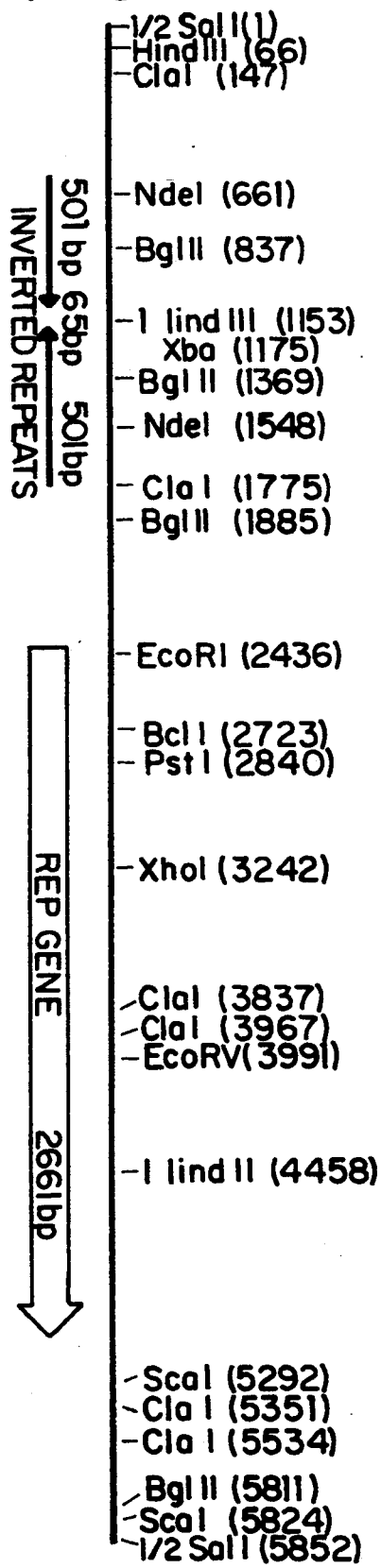
FIG. 3 is a schematic representation of the major structural features of Ddp2 aligned with a map of the cleavage sites of some restriction enzymes.
Figure 4:
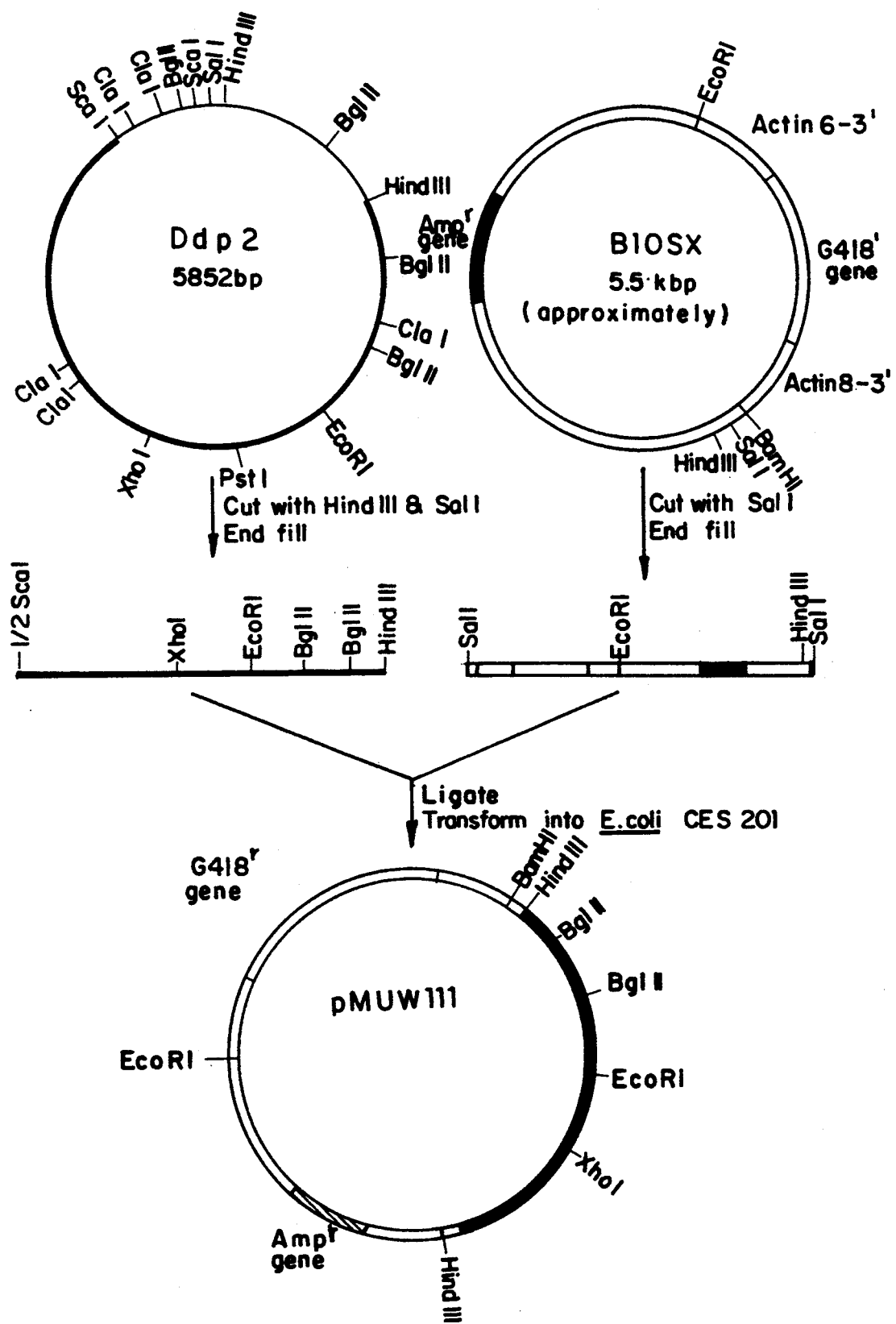
FIG. 4 is a schematic representation of the construction of plasmid pMUW111.

The present inventors have established for the first time the full nucleotide sequence of the Dictyostelium plasmid Ddp2 as shown in FIG. 1 (SEQ ID NO: 2). The nucleotide sequence has been numbered clockwise around the circular DNA molecule starting at the single cut site of the SalI restriction enzyme. Detailed examination of the DNA sequence of Ddp2 has allowed different functional regions of the plasmid to be distinguished, as shown in FIG. 3, and regions likely to be unstable when cloned in *E. coli*. The elucidation of these different functional regions has allowed the present inventors to overcome a number of the technical problems that have hitherto limited the use of extrachromosomal vectors in Dictyostelium.

The DNA sequence of Ddp2 between nucleotide 2378 and 5038 encodes a gene referred to herein as Rep. This section of Ddp2 contains a large "open reading frame" where one of the six possible ways to read the triple nucleotide genetic code (known as codons) has a long region without any of the codons that act as stop signals for protein translation. Such an "open reading frame" considered along with flanking sequences that are similar to the promoter and poly-adenylation signals of previously described Dictyostelium genes (Kimmel & Firtel, 1982 In The Development of *Dictyostelium discoideum*, Academic Press, New York, pp234-324) is strong evidence that the Rep gene could be transcribed into RNA and translated into a polypeptide containing 887 amino acids with the sequence (SEQ ID NO: 3) shown in FIG. 2. Evidence supporting the view that the Rep gene is translated into a polypeptide comes from the inability of plasmids constructed with interruptions to the Rep gene, for example pMUW102, to replicate in wild type strains of *Dictyostelium discoideum*. The RNA and polypeptide product of the Rep gene has not yet been detected and it is believed to be produced in only low amounts to positively regulate the initiation of plasmid replication by the host enzymes that normally replicate chromosomal DNA. However, it should be appreciated that either the messenger RNA or the translated polypeptide derived from the Rep gene could be processed by the cellular biochemical machinery to produce one or more shorter polypeptides. It is also likely that the polypeptide also contains regions that act as negative regulators of plasmid copy number. None of these areas of uncertainty subtract from the basic discovery that at least part of the open reading frame encodes a polypeptide that is essential for the replication of Ddp2. This finding explains the previously established need for shuttle vectors to contain a large section of Ddp2 DNA since such vectors would need to contain both the origin of replication and an additional 2.66 kilobase pair Rep gene plus flanking control sequences.

Plasmid vectors based on Ddp2 need to contain DNA from the section of Ddp2 between the HindIII restriction enzyme site at 1153 base pairs and the BglII restriction enzyme site at 1885 base pairs.

Figure 5:
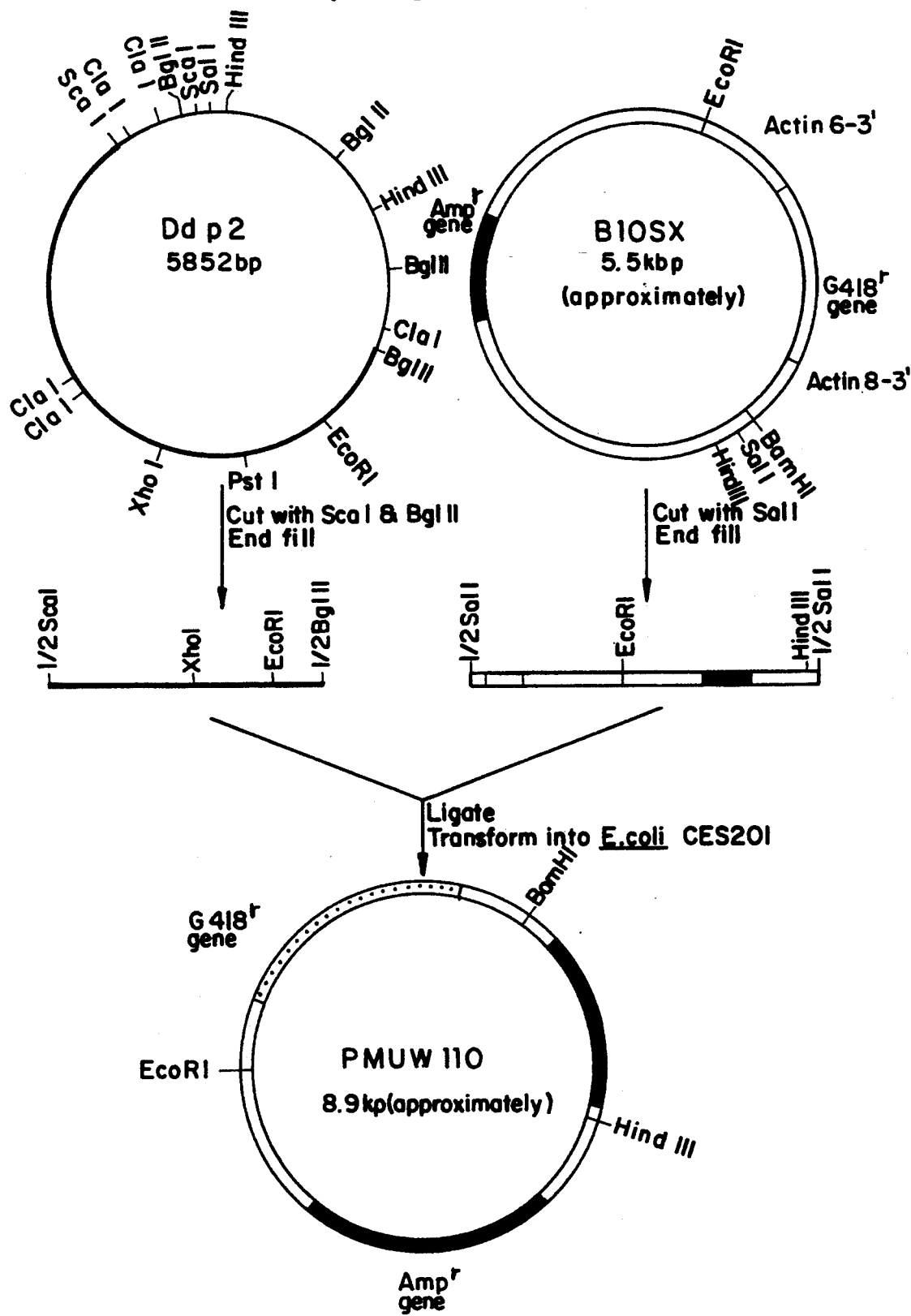
FIG. 5 is a schematic representation of the construction of plasmid pMUW110.
Figure 6:
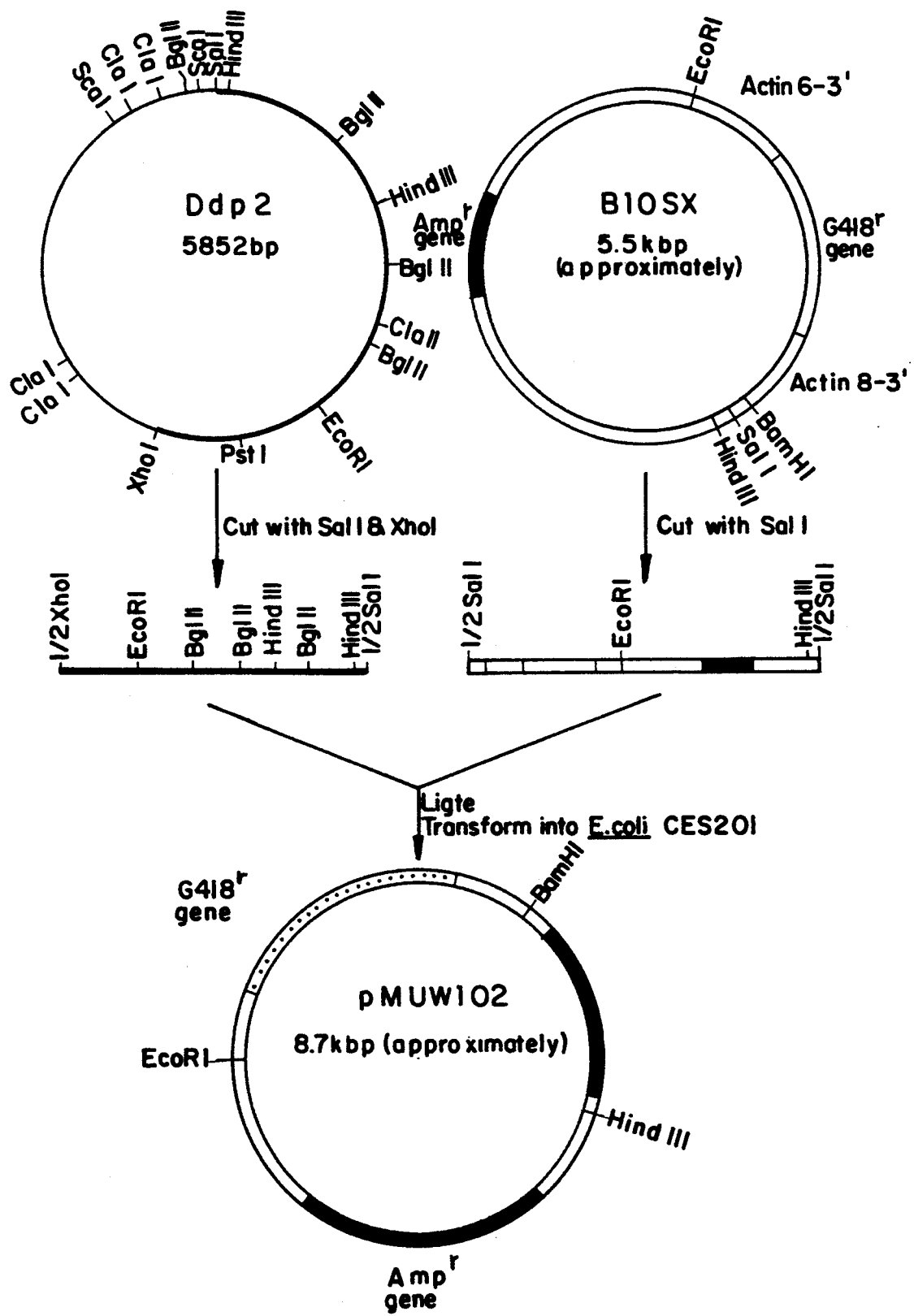
FIG. 6 is a schematic representation of the construction of plasmid pMUW102.
Figure 7:
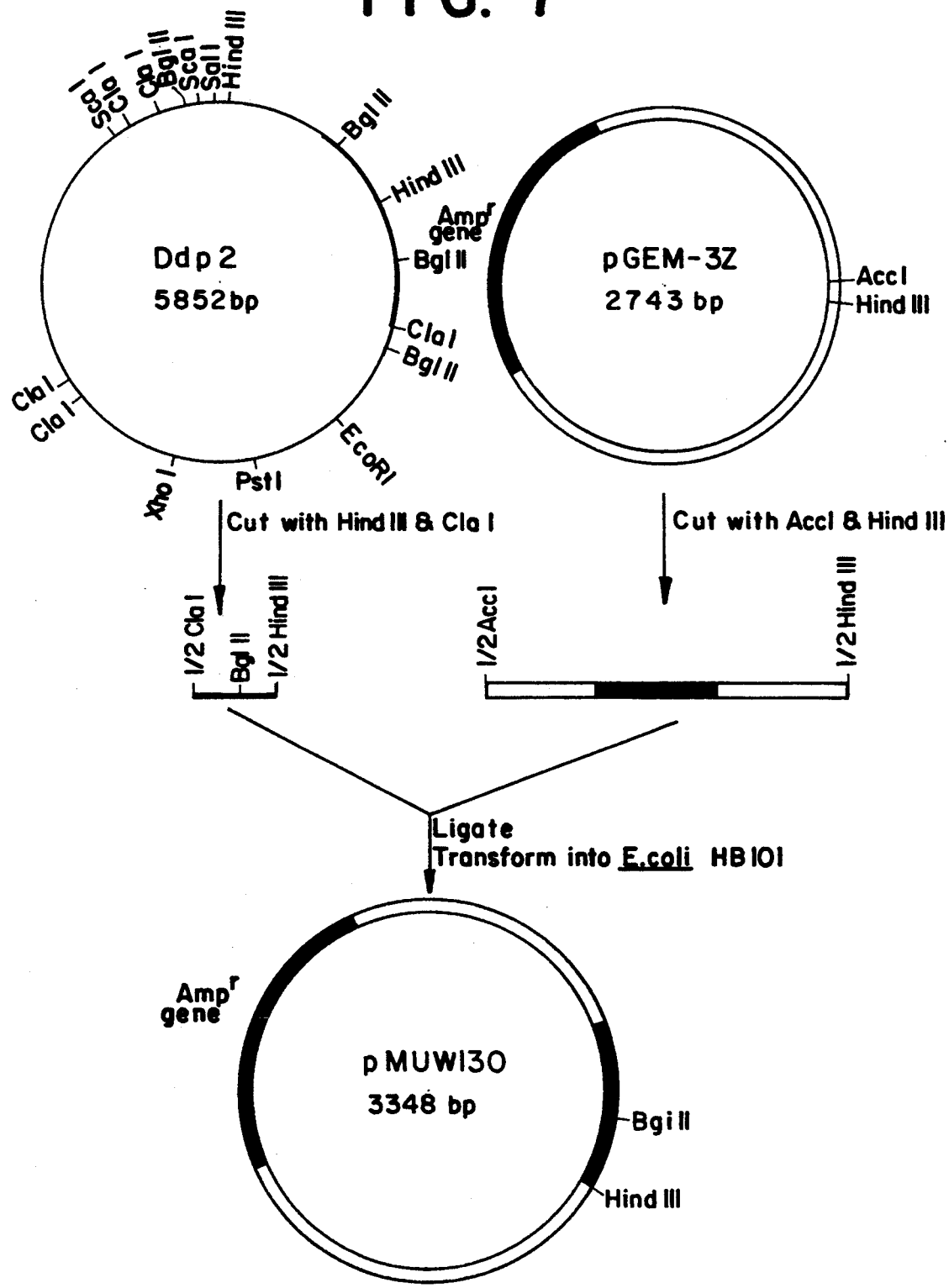
FIG. 7 is a schematic representation of the construction of plasmid pMUW130.
Figure 8:
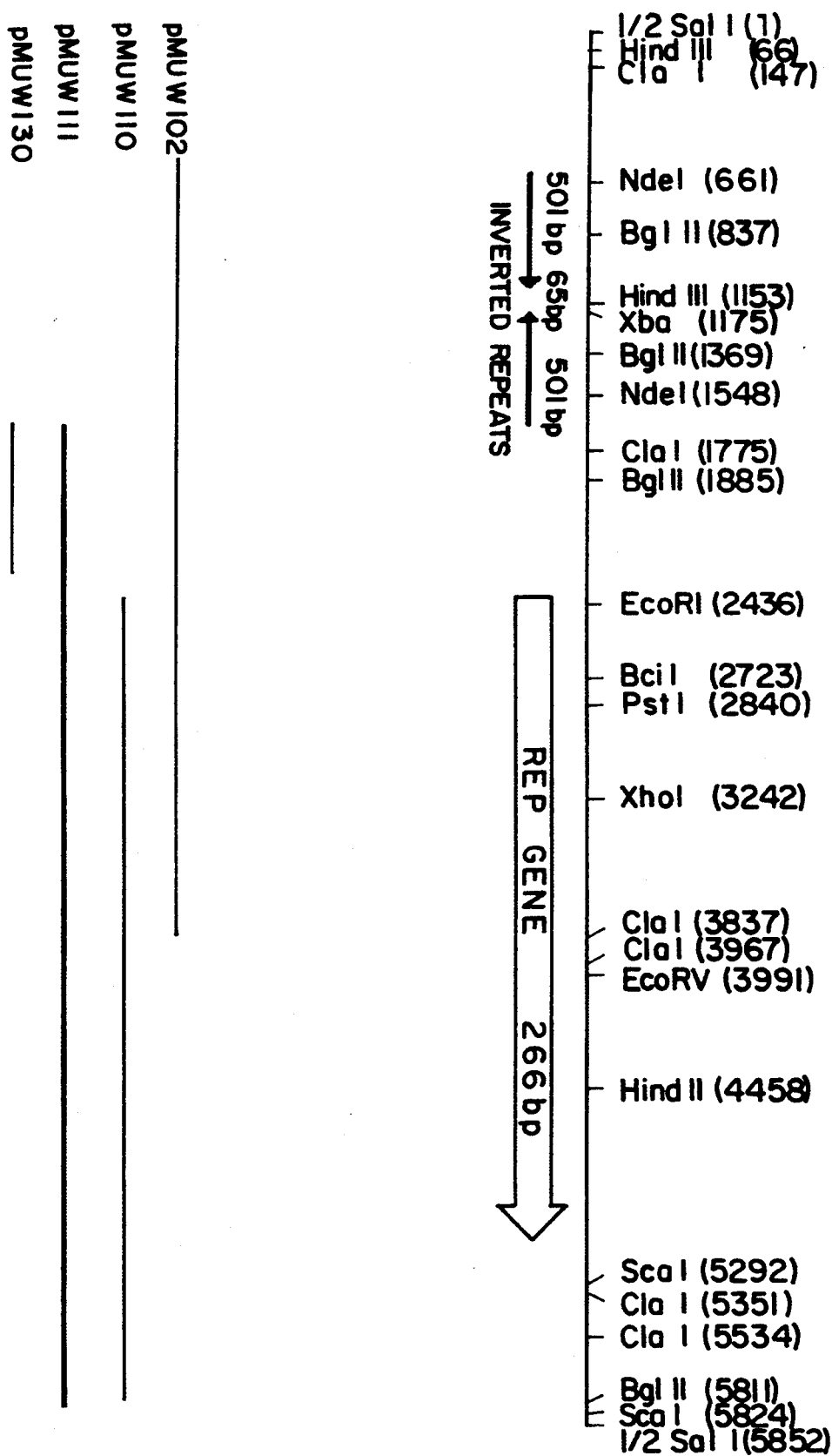
FIG. 8 is a schematic representation which summarizes the Ddp2 sequences used to construct plasmids pMUW111, pMUW102, pMUW110 and pMUW130.
Figure 9:
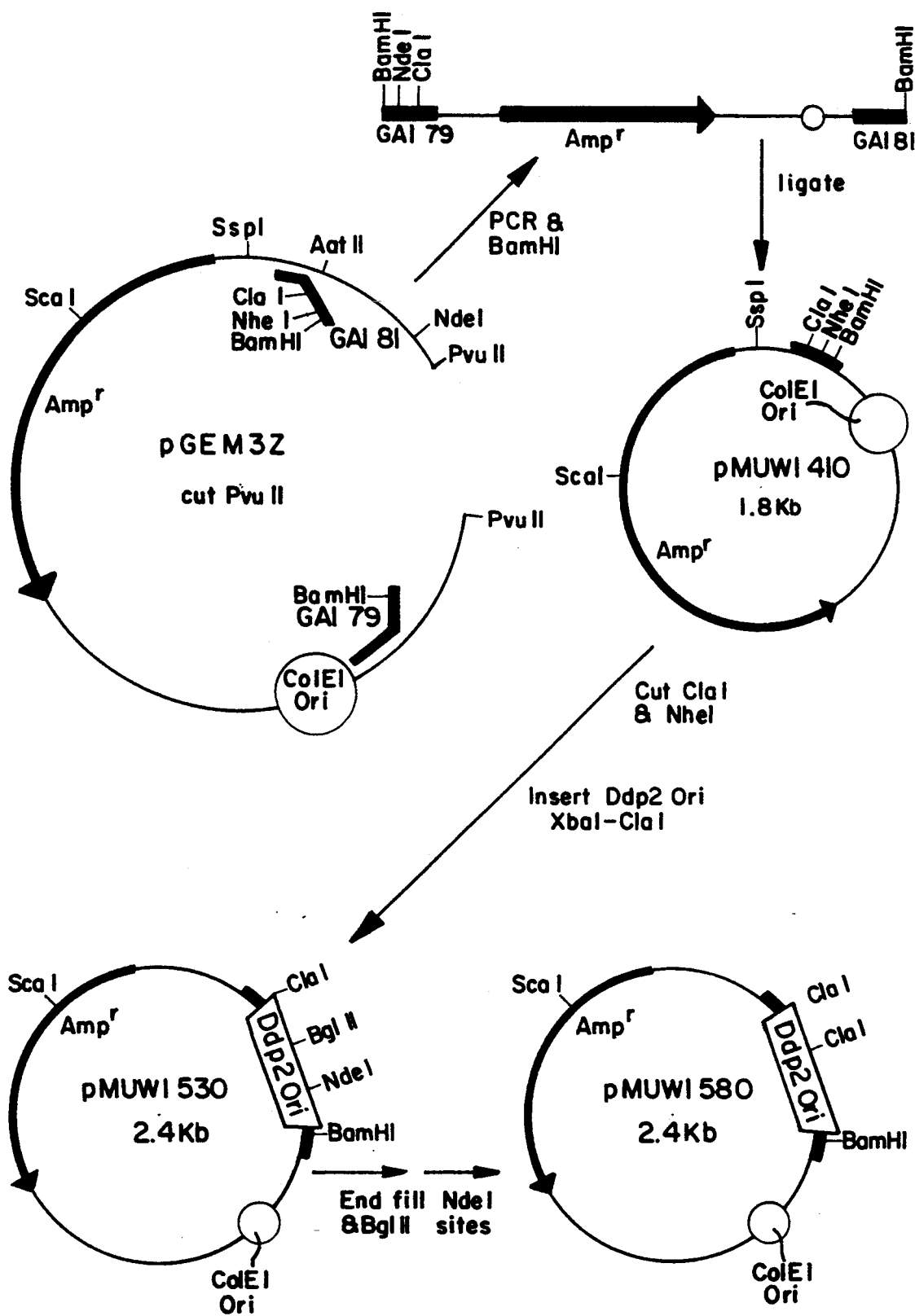
FIG. 9 is a schematic representation of the construction of the shuttle vectors pMUW1530 and pMUW1580.

This is demonstrated by the inability of plasmids that lack this section of DNA, for example pMUW110 (FIG. 5), to replicate in wild type strains of Dictyostelium. Plasmid pMUW110 contains the complete Rep gene plus flanking sequences including the polyadenylation sequences and 483 nucleotides encompassing the promoter region. Thus pMUW110 contains the sequences required to produce the polypeptide required for replication, but lacks a functional origin of replication. Consequently, a Ddp2 origin of DNA replication or associated control sequences must lie before the BglII restriction enzyme site at 1885 base pairs. This region of Ddp2 is present in plasmid pMUW102 which contains the section of Ddp2 between the HindIII restriction enzyme site at 1153 base pairs and the XhoI restriction enzyme site at 3242 base pairs using plasmid pMUW102 (FIG. 6), but plasmid pMUW102 lacks a functional Rep gene and so is unable to replicate in wild type strains of Dictyostelium. The presence of a functional origin of replication in plasmid pMUW102 is demonstrated by transforming it into Dictyostelium strains along with plasmid pMUW110 to provide the essential replication polypeptide from the Ddp2 Rep gene. The present inventors experimental results clearly show that plasmid pMUW110 is inserted into the chromosomal DNA to form a stable recombinant strain of Dictyostelium and, in the same cells, plasmid pMUW102 is stably maintained as an extrachromosomal plasmid. This demonstration of an extrachromosomal plasmid containing an origin of replication from plasmid Ddp2 and its maintenance in a Dictyostelium strain by virtue of chromosomal DNA containing the Rep gene encoding polypeptides essential for plasmid replication represents a significant technical advance. It is apparent to one skilled in the art that similar techniques can be utilised for the construction of a diverse range of plasmid vectors for Dictyostelium.

It is relevant to briefly examine the mechanism for selecting cells that were successfully transformed with both pMUW102 and pMUW110. Both these vectors contain a selectable marker conferring resistance to the antibiotic G418, but other genes could be used to serve the same function. In fact the present inventors have developed another resistance gene bleomycin for use as a selectable marker in Dictyostelium. The G418 resistance gene is under the control of Dictyostelium actin 6 promoter and the actin 8 3' poly-adenylation signals to ensure that it is expressed in Dictyostelium cells to provide a method of selecting the few cells that take up the plasmid DNA. Plasmid pMUW110 which lacks an origin of replication can only be retained in those few cells where the plasmid becomes integrated into the chromosomal DNA. Any cells that are transformed with only plasmid pMUW102 can only be resistant to G418 if the plasmid becomes integrated into the chromosomal DNA since this plasmid cannot replicate without the polypeptide produced by the Rep gene. However, some of the cells that receive both plasmids can have the plasmid pMUW110 integrated into the chromosomal DNA in a manner that preserves the function of the Rep gene and so will be able to maintain multiple extrachromosomal copies of the plasmid pMUW102. Once the cells transformed with both plasmids pMUW102 and pMUW110 have been selected by resistance to G418 they may be stably maintained in the absence of the antibiotic.

Plasmid pMUW102 contains 2089 base pairs of Ddp2; a considerably smaller section of Ddp2 than previously known to be capable of extrachromosomal replication. This sequence has been substantially shortened by removing more of the Ddp2 DNA sequences that are not essential for the replication of plasmid pMUW102 in recombinant strains of Dictyostelium. The results with plasmid pMUW130 confirms that all the DNA sequences necessary for stable extrachromosomal replication at high copy number are contained in a 622 base pair HindIII-ClaI fragment of Ddp2. In the light of present knowledge as disclosed herein, it is also relatively simple to ascertain the essential sequences within the section of Ddp2 between the HindIII restriction enzyme site at 1153 base pairs and the ClaI restriction enzyme site at 1885 base pairs using standard molecular biology techniques such as deletions and insertions. Experiments to determine the minimum section of Ddp2 DNA sequence necessary for plasmid vector construction have been carried out. Several copies of a TGTCATGACA (SEQ ID NO: 1) sequence are essential for the function of the Ddp2 origin of replication.

The use of smaller sections of Ddp2 for vector construction than previously possible allows the omission of some of the sequences likely to be responsible for plasmid instability in E. coli. Plasmid pMUW130 contains only one copy of sequences in the 501 base pair inverted repeat of Ddp2 and does not contain the long stretches of poly-adenine or poly-thymidine found between the end of the open reading frame and the SalI restriction enzyme site. Such inverted repeats and poly-adenine or poly-thymidine sequences are known to be unstable in E. coli. Plasmid pMUW130 also omits the (GATGAA)11 (SEQ ID NO: 19) repeat found at the end of the Rep gene and which is also likely to be unstable in E. coli. Therefore, it appears that the smaller sections of Ddp2 used to construct plasmid vectors according to this invention have less of the problems of stability in E. coli than were previously encountered using larger segments of Ddp2 DNA.

The integrating plasmid pMUW110 contains all the information necessary for the controlled expression of the Ddp2 Rep gene required to maintain the copy number of plasmid pMUW102. This control of plasmid copy number could not be predicted since there would be no direct linkage between the number of copies of the plasmid and the Rep gene as in the original plasmid. It is thought that this copy number control is probably achieved by an auto-regulatory mechanism where the product of the Rep gene represses further transcription from the Rep gene and so maintains a constant cellular concentration of the polypeptide that regulates plasmid replication. The localisation of the promoter sequences to the section of Ddp2 DNA between the BgIII restriction enzyme site and the start of the Rep gene, as disclosed herein, allows future experiments to determine the regulatory mechanisms governing the transcription of the open reading frame and control of plasmid copy number. It is anticipated that this approach will lead to experimental control of plasmid replication and copy number by suitable modification or duplication of the control sequences.

In the experiments described herein, the plasmid pMUW110 has been stably integrated into the Dictyostelium chromosomal DNA using the same selective marker, G418 resistance, as present on the extrachromosomal plasmid pMUW102. However, there would be advantages in using a different selective marker on the integrating vector from that used for the extrachromosomal plasmid. The present inventors have developed a thymidylate synthase gene as a second marker for selection in a Dictyostelium discoideum strain that is unable to synthesise thymidine (Chang et al, 1989, Nucleic Acids Research 17, 3655-3661). The thymidylate synthase selection has the advantage for biotechnological uses in that the selection is maintained in the absence of any antibiotic. Clearly any combination of selectable markers can be used on the integrating or extrachromosomal vectors, but the preferred combination is to have the thymidylate synthase marker on the extrachromosomal plasmid and maintain it in the enzyme deficient Dictyostelium strain. This means that, without using any antibiotic selection, any host cell losing either the extrachromosomal plasmid or the functional integrated vector would be unable to grow since any cell losing the production of the polypeptide necessary for plasmid replication would also lose the functions encoded on the extrachromosomal plasmid.

Examples of the application of the invention have been demonstrated by the construction of a range of shuttle vectors and the production of a recombinant protein in Dictyostelium discoideum. The novel shuttle vectors pMUW1530, pMUW1570 and pMUW1580 incorporate the Ddp2 origin of replication on the 600 bp XbaI—ClaI fragment (1175-1775 bp) of Ddp2 into a small E. coli plasmid (pMUW1510) that contains close to the minimal amount of sequence from pBR322 required for replication in E. coli in order to reduce the potential for these sequences to adversely effect the function of the shuttle vector in D. discoideum. Other useful features of these shuttle vectors is that they contain very few sites for six base restriction enzymes, apart from single BamHI and ClaI sites in appropriate positions for the insertion of additional DNA without disrupting essential functions. Sequences that might be inserted into such sites include genes for the production of recombinant proteins or selective markers, promoter sequences to control gene function and signal sequences for the correct processing of messenger RNA molecules and the translated proteins. This is illustrated by the construction of a novel "expression cassette" suitable for the production and secretion of a recombinant proteins from Dictyostelium cells. This expression cassette contains the promoter from the D. discoideum actin 15 gene, a section of the D19 gene encoding a secretion signal peptide, the polylinker from the E. coli plasmid pGEM3Z (for insertion of genes for expression) and lastly the polyadenylation signal from the D. discoideum actin 15 gene. However, it will be apparent to one skilled in the art that a wide range of similar constructs could be made for this purpose using DNA sequences from other genes or even completely synthetic sequences serving the same functions.

The applications of the shuttle vector based on the technology disclosed in this document was demonstrated by the production of a recombinant protein from an E. coli gene for enzyme B-glucuronidase from D. discoideum cells containing an expression vector constructed by inserting the expression cassette into the shuttle vector pMUW1580.

Plasmid Ddp2 is believed to be the first functionally characterized member of a new group of structurally and functionally similar plasmids. This new group of plasmids can be defined as all encoding a single polypeptide of 700–1000 amino acids which is essential for plasmid replication and which has sequence homologies with the Ddp2 Rep gene, indicating a common evolutionary origin. Further, the origin of replication of these plasmids is associated with one arm of an inverted repeat sequence that is distinct from the Rep gene. The inventors confidently predict that the techniques they have disclosed in this application can be used to construct further extrachromosomal plasmid vectors for use in the biotechnology industry starting from the functionally analogous regions of any of this broader group of "Ddp2-like" plasmids.

The only other member of this "Ddp2-like" group of plasmids to have been sequenced to date is plasmid pDG1 isolated from a unidentified Dictyostelium species (Orii et al (1987) Nucleic Acids Res. 15, 1097–1107). Plasmid pDG1 has a very similar structure to Ddp2, possessing similar sized inverted repeats and a single open reading frame analogous to the Rep gene of Ddp2. Despite plasmid pDG1 having been fully sequenced, nothing is known regarding the functions of these features or the location of the origin of replication (Orii et al (1989) Nucleic Acids Res. 17, 1395–1408). The only recombinant shuttle vector produced with pDG1 sequences incorporated the long, 4.2 Kb ClaI fragment of pDG1, i.e., omitting only 0.2 Kb from the whole plasmid (Orii et al (1989) Nucleic Acids Res. 17, 1395–1408). Such pDG1 based plasmids are very unstable in *E. coli* (Saing et al (1988) Mol. Gen. Genet. 214, 1–5) and so are unsuitable for use in the production of recombinant proteins.

The plasmid pDG1 is recognized as a member of the "Ddp2-like" group of plasmids by virtue of its having a similar structure and having sequence homologies with Ddp2 in the region of the open reading frame at both the DNA and amino acid levels. The non-coding regions of these two plasmids have little sequence homology, apparently being free to diverge in the course of evolution. The presence of large inverted repeats in both pDG1 and Ddp2 is probably not a key feature of the group of "Ddp2-like" plasmids as only one copy is essential for the replication of Ddp2.

In the light of the functional data from the analogous regions of Ddp2, as disclosed in this application it is possible to re-evaluate the pDG1 sequence data and predict that pDG1 origin of replication lies outside the operating reading frame and overlaps with one of the inverted repeats. In addition, the speculation (Ori et al (1989) Nucleic Acids Res. 17, 1395–1408) concerning the weak homologies of the Rep gene with reverse transcriptase is unlikely to be correct as the homology is not conserved in Ddp2. The Rep gene of Ddp2 can be aligned with the open reading frame of pDG1 with 35% of amino acids in identical positions indicating considerable evolutionary homologies. The proteins encoded by the two plasmids also have similar structures, being comprised of two similar sized domains separated by a threonine rich sequence and the carboxy terminus of both proteins being a highly acidic glutamic and aspatic acid rich sequence. To one skilled in the art, the similarities between the proteins produced by these two plasmids indicates they have very similar functions and also indicates regions of high sequence homology which are most likely to have roles crucial for the proteins function. Whilst it is unlikely that the protein from pDG1 would be sufficient to cause replication of the Ddp2 origin of replication (and vice versa) because the sequence recognized by the protein is likely to be specific to the individual origin of replication, it is very likely that novel proteins constructed from sections of both proteins would function correctly. For example, the replacement of the acidic carboxy terminus of the Ddp2 Rep protein with the carboxy terminus of the pDG1 protein should not affect the ability of the molecule to allow replication from the Ddp2 origin of replication. Furthermore, it should be possible to change the specificity of the Ddp2 Rep gene simply by replacing the section of the protein that recognizes the Ddp2 origin of replication by a section recognizing an origin of replication from another member of the "Ddp2-like" group of plasmids. Clearly, the basic technology disclosed in this application, whereby, the replication protein and the origin of replication are separated onto separate vectors, is capable of a wide range of different applications for the construction of plasmid vectors incorporating sections from the broad group of "Ddp2-like" plasmids.

EXAMPLE 1

Sequencing of plasmid Ddp2

Our laboratory at Macquarie University sequenced Ddp2 by cutting Ddp2 DNA into many small fragments and cloning them separately into a commercially available plasmid called pGEM3Z (Promega Corporation, Madison, USA). In this vector, small sections of Ddp2 DNA were stable and could be sequenced using a technique called "double stranded sequencing" where a small oligonucleotide is used to prime the synthesis of a new radio-labelled DNA strand on a template of denatured plasmid DNA. The oligonucleotide primer can be the complementary sequence to the SP6 or T7 regions flanking the cloning site or it can be a custom synthesised oligonucleotide with a sequence that matches part of the cloned Ddp2 DNA.

Ddp2 DNA was digested with the restriction enzymes ClaI, Sau3A, AluI or RsaI and cloned into the plasmid pGEM3Z at the AccI, BamHI or SmaI restriction enzyme sites using standard molecular biology techniques, and transformed into the *E. coli* strain JM109. Clones containing Ddp2 DNA were selected at random and stored in broth containing 15% glycerol and stored at −80 degrees.

Plasmid DNA from the clones was prepared using alkaline lysis and a RNAse enzyme treatment as recommended by the Promega literature on pGEM3Z. Before use in the sequencing reaction, 4 ug of each plasmid was alkaline denatured with a brief treatment with 0.4M sodium hydroxide, precipitated with ethanol and annealed with 10 picomoles of oligonucleotide primer according to the procedure recommended by Pharmacia LKB Biotechnology (Uppsala, Sweden) for their T7 DNA polymerase sequencing kit which was used for the sequencing reaction. The sequencing reaction used ATP radio-labelled with $^{35}S$. The radio-labelled DNA was separated on 6% acrylamide/8M urea gels which were then fixed in 10% methanol plus 10% acetic acid, dried and autoradiographed. The sequence revealed by the autoradiography films were entered into a computer and then overlapping sequences matched automatically and compiled into the complete DNA sequence of Ddp2.

The full sequence of Ddp2 is available from the EMBL data base, accession number X51478.

EXAMPLE 2

Location of the Origin of Replication of Ddp2

In further experiments the Ddp2 origin of replication was located to within the HindIII—ClaI fragment (1153–1775 bp) of Ddp2 as in plasmid pMUW130.

pMUW111

The plasmid pMUW111 was constructed by inserting the 4.1 Kb HindIII to ScaI fragment of Ddp2 into the SalI site of BIOSX. BIOSX is an integrating *D.discoideum/E. coli* shuttle vector constructed by Nellen et al. (Gene. 39 (1985) 155–163) and contains the Ampicillin and Kanamycin/G418 antibiotic resistance genes.

Ddp2 plasmid was first digested with restriction enzymes HindIII and ScaI. After the digestion was completed, the Hind III 5' overhang ends were made blunt using an end-filling reaction involving the enzyme DNA polymerase I "Klenow fragment". After this reaction was completed, it was fractionated in a 0.8% TBE agarose gel. The 4.1 Kb fragment was then excised from the gel and purified using a commercial kit, "Gene-Clean" (BIO101,Inc., USA). The purified DNA was then ligated with BIOSX that had been digested with SalI and end-filled. After ligation, the mixture was transformed into *E. coli* strain CES201 (Leach, D. R. F. and Stahl, F. W. (1983). Nature 305, 448–451). CES201 was made competent for transformation using the procedure as published by Hanahan, D. (J. Mol. Biol. (1983) 166, 557–580). The transformation mixture was then plated onto Luria-agar containing 50 ug/ml ampicillin. *E. coli* ampicillin resistance transformants containing pMUW111 were confirmed by restriction fragment mapping of isolated plasmids and also by radioactive hybridization using Ddp2 as a probe.

10 ug of pMUW111 was then used to transform Dictyostelium axenic strain, AX3K, using the standard calcium phosphate precipitation procedure developed by Nellen W. et al. (Mol. Cell. Biol. (1984) 4, 2890–2898) with G418 selection. To determine if pMUW111 was capable of autonomous replication, total nuclear DNA was isolated from G418 resistant transformants and then screened on a "lysis in the gel" as described by Noegel A. et al (J. Mol. Biol. (1985) 185, 447–450). The gel was then southern-transferred onto zeta-probe blotting membrane (Bio-RAD) and hybridized using $^{32}$P-labelled Ddp2 DNA. Autoradiography showed that pMUW111 had a higher mobility than the bulk chromosomal DNA, indicating it existed as an autonomously replicating plasmid.

pMUW102

The plasmid pMUW102 was constructed by inserting the 3.2 Kb SalI to XhoI fragment of Ddp2 into the Sal I site of BIOSX. This fragment contained only part of the open reading frame. Hence a complete functional protein(s) would not be expected to be produced by this construct.

Ddp2 plasmid was first digested with restriction enzymes SalI and XhoI. The sample was then fractionated in a 0.8% TBE agarose gel. The 3.2 Kb fragment was then excised from the gel and purified using a commercial kit, "Gene-Clean". The purified DNA was then ligated with BIOSX that had been digested with SalI. After ligation, the mixture was transformed into competent *E. coli* strain CES201. The transformation mixture was then plated onto Luria-agar containing 50 ug/ml ampicillin. *E. coli* ampicillin resistant transformants containing pMUW102 were confirmed by restriction fragment mapping of isolated plasmids and also by radioactive hybridization using Ddp2 as a probe.

10 ug of pMUW102 was then used to transform *D. discoideum* axenic strain, AX3K, using standard calcium phosphate precipitation procedure with G418 selection. To determine the fate of pMUW102, total nuclear DNA was isolated from G418 resistant transformants and then screened on a "lysis in the gel". The gel was then southern-blotted onto Zeta-probe blotting membrane and hybridized using $^{32}$P-labelled Ddp2 DNA. Autoradiography showed that pMUW102 had the same mobility as the bulk chromosomal DNA, indicating it had integrated into chromosomal DNA and it was not capable of existing as a free plasmid. This experiment demonstrated that an intact open reading frame is essential for existence as an autonomously replicating plasmid.

pMUW110

The plasmid pMUW110 was constructed by inserting the 3.4 Kb BglII to ScaI fragment of Ddp2 into the Sal I site of BIOSX. This fragment contained the whole open reading frame "Rep gene" and the 5' and 3' flanking sequences that control the production of protein(s) specified by the open reading frame.

Ddp2 plasmid was first digested with restriction enzymes ScaI and BglII. After the digestion was completed, the BglII 5' overhang ends were made blunt using an end-filling reaction involving the enzyme DNA polymerase I "Klenow fragment". After this reaction was completed, the sample was fractionated in a 0.8% TBE agarose gel. The 3.4 Kb fragment was then excised from the gel and purified using a commercial kit, "Gene-Clean". The purified DNA was then ligated with BIOSX that had been digested with SalI and end-filled.

After ligation, the mixture was transformed into *E. coli* strain CES201 that had been made competent for transformation. The transformation mixture was then plated onto Luria-agar containing 50 ug/ml ampicillin. *E. coli* ampicillin resistant transformants containing pMUW110 were confirmed by restriction fragment mapping of isolated plasmids and also by radioactive hybridization using Ddp2 as a probe.

10 ug of pMUW110 was then used to transform *D. discoideum* axenic strain, AX3K, using standard calcium phosphate precipitation procedure with G418 selection. To determine the fate of pMUW110, total nuclear DNA was isolated from G418 resistant transformants and then screened on a "lysis in the gel". The gel was then southern-transferred onto zeta-probe blotting membrane and hybridized using $^{32}$P-labelled Ddp2 DNA. Autoradiography showed that pMUW110 had the same mobility as the bulk chromosomal DNA, indicating it had integrated into the chromosomal DNA and it was not capable of existing as a free plasmid.

The difference between pMUW111 and pMUW110 is that 732 nucleotides between the HindIII restriction enzyme site at 1153 base pairs and the BglII restriction enzyme site at 1885 base pairs is missing in pMUW110. Hence the inability of pMUW110 to exist as a plasmid in AX3K could be explained by one of the following:
i) The 732 bp sequence contained part of the origin of replication (ORI) of the plasmid Ddp2.
ii) The 732 bp sequence contained cis acting element(s) that control the production of protein(s) specified by the open reading frame.

The first explanation was found to be correct by a subsequent experiment involving the co-transformation of AX3K with both pMUW102 and pMUW110. Screening of the G418-resistant transformants revealed that pMUW102 had a higher mobility than the bulk chromosomal DNA. This proved that pMUW102 could exist as an extrachromosomal plasmid only in the presence of pMUW110, which contained the intact open reading frame and hence is capable of providing the transacting protein(s) required for pMUW102 to replicate as a plasmid.

pMUW130

The plasmid pMUW130 was constructed by inserting the 622 base pair HindIII to ClaI fragment from Ddp2 (i.e. 1153 base pair to 1775 base pair) into the commercial E. coli plasmid pGEM3Z (Promega Corporation, Madison, USA) which had been digested with AccI and HindIII restriction enzymes. The construction of the plasmid used the same procedure as that of pMUW102 (above) except that the E. coli strain used was HB101.

Plasmid pMUW130 contains most of the 732 base pairs sequence that are in plasmid pMUW102, but not in plasmid pMUW110 and which was thought to be required for extrachromosomal replication. An experiment where pMUW102 and pMUW110 were co-transformed into D. discoideum strain AX3K demonstrated that pMUW130 can replicate extrachromosomally in the presence of pMUW110 which has been integrated into the chromosomal DNA. This confirms that an origin of DNA replication is located on this small HindIII—ClaI fragment of Ddp2 DNA. At approximately 3.3 kilobase pairs of DNA, pMUW130 was substantially smaller than previous shuttle vectors that had been constructed for Dictyostelium spp.

The location of an origin of replication on the HindIII—ClaI fragment incorporated into plasmid pMUW130 raises interesting scientific questions as to whether the similar sequences that occur in the small HindIII fragment (66-1153 bp) are also capable of acting as an origin of replication. This was investigated by cloning the small HindIII fragment (66-1153 bp) into the Hind III site of plasmid B10SX to form plasmid pMUW105. However, plasmid pMUW105 was unable to replicate extrachromosomally when mixed with plasmid pMUW110 (to provide the Rep gene) and transformed into D. discoideum strain AX3K. The small HindIII fragment in pMUW105 contains an entire, near perfect copy of the 501 bp inverted repeat sequence that forms most of the Ddp2 origin of replication in plasmid pMUW130. So the failure of pMUW105 to replicate extrachromosomally demonstrates that either the sequences just outside the 501 bp inverted repeat are essential for replication or the 11 nucleotide substitutions between the two copies of the 501 bp inverted repeat have prevented the copy in the small HindIII fragment in pMUW105 from acting as the origin of replication. Both of these possibilities result in the absence of or changes to copies of the DNA sequence TTTTTTGTCATGACACTTTTTTTTTTTTGTCATGACA (SEQ ID NO: 6), one copy of which lies just outside the 501 bp inverted repeat in pMUW130 and while a second copy of which is altered in pMUW105. This sequence contains two copies of a 10 bp palindrome TGTCATGACA (SEQ ID NO: 1) (i.e. the two halves are symmetrical, so the complementary DNA strand will have the same sequence in the opposite orientation). Such palindromic sequences are typical of many sites recognized by DNA binding proteins, which would be consistent with this sequence being important for regulation of the origin of replication.

The Ddp2 origin of replication in plasmid pMUW130 contains two copies of the above oligo T sequence, each of which contains two palindromes. Deletion of one copy of the sequence by cutting out the HindIII—BglII restriction fragment (1153-1369 bp, numbered according to Ddp2) of plasmid pMUW130 produced plasmid pMUW138 which is unable to replicate extrachromosomally in D. discoideum, thus demonstrating the importance of this sequence for the function of the origin of replication. However, it is unlikely that this sequence is the actual origin of replication, which is believed to lie in flanking sequences.

EXAMPLE 3

Construction of a Small Shuttle Vector

A list of oligonucleotide sequences used in vector constructions is shown in Table I.

Despite plasmid pMUW130 being a great improvement on all shuttle vectors previously available for D. discoideum, it has some drawbacks for use in the biotechnology industry. Plasmid pMUW130 contains a disrupted polylinker (concentrated region of restriction enzyme sites) and DNA sequences derived from the Lac operon and the parent pBR322 plasmid which are not required in a Dictyostelium vector.

Ideally, the restriction enzyme sites in an expression plasmid should be only in positions convenient for the manipulation of the gene to be expressed and the amount of unnecessary DNA should be minimized. Shuttle plasmid pMUW 1530 was designed specifically for the purpose of easy manipulation of inserted sequences. This plasmid contains the minimal sequences derived from pBR322 that allow replication in E. coli plus the ampicillin resistance selective marker. The "poison sequences" that are known to interfere with replication from the SV40 origin of replication (Lusky & Botchan (1981) Nature 293, 79-81.) and gene expression in mammalian cells (Peterson et al (1987) Mol. Cell. Biol. 7, 1563-1567) were excluded, although as yet their influence on D. discoideum plasmids is unknown. Other features of the plasmid include the creation of two unique six base restriction sites (BamHI and ClaI) positions suitable for the insertion of expression cassettes or selective markers.

TABLE 1

LIST OF OLIGONUCLEOTIDE SEQUENCES USED IN VECTOR CONSTRUCTION.

The sequence (5' to 3') of the oligonucleotides synthesised at Macquarie University is shown together with the approximate position of restriction enzyme cutting sites.

PCR primers for cloning the actin15 promotor

GA190 (SEQ ID NO: 10).  TGGCCAAGCTTAGATCTACAAATTAATTAATCCC
                        EaeI    HindIII      BglII GA188 (SEQ ID NO: 11).         CCCGGGATGTTCACCATGCATTTTTATTTTTTA
                        SmaI/AvaI   FokI         NsiI PCR primers for cloning the actin15 3' region

TABLE 1-continued

LIST OF OLIGONUCLEOTIDE SEQUENCES USED IN VECTOR CONSTRUCTION.

GA189 (SEQ ID NO: 16).   TGCCGGTACCTAAATCATGAATGAAAGTGCT
                         KpnI

GA186 (SEQ ID NO: 17).   CCCGGGAATTCAGATCTTTTCATGGAGATTGTAT
                         SmaI/AvaI  EcoRI  BglII

PCR primers for cloning the secretion signal from the D19 gene

GA187 (SEQ ID NO: 12).   GGGAAGCTTGGATGAATTCAAAAAATGAAATTCCAACAT
                         HindIII    FokI    EcoRI GA182 (SEQ ID NO: 13).   CCCGGGTCGACCTGCTATTGCATTTGCATATGTTAA
                         SmaI/AvaI  SalI  BsmpI              NdeI Linker inserted into NdeI site to complete secretion signal sequence GA297 (SEQ ID NO: 14).   TACGCCAATGCATATGAAAGCT
                                   NsiI   HindIII
                                          NdeI GA296 (SEQ ID NO: 15).   TAAGCTTTCATATGCATTGGCG
                         HindIII  NdeI   NseI PCR primers used to clone pGEM3Z origin of replication GA181 (SEQ ID NO: 8).    GGGGTGGATCCGCTAGCCGCATCGATAGGTGGCACTTTTCGG
                               BamHI  NheI         ClaI GA179 (SEQ ID NO: 7).    GGAGGGATCCAAAGGCCAGCAAAAGGCCAGCAAAAGGC
                              BamHI Sequencing oligonucleotide for pMUW1410

GA220 (SEQ ID NO: 9).    GAAGCATTTATCAGGG

Linker used to clone the gene for B-glucuronidase

GA310 (SEQ ID NO: 18).   AATTCCCGGG
                         EcoRI  SmaI pMUW1410

Plasmid pMUW1410 is an *E. coli* plasmid which was made to be the basis for construction of a series of shuttle vectors, including pMUW1530.

Plasmid pMUW1410 was constructed using two synthetic oligonucleotides GA179 (SEQ ID NO: 7) and GA181 (SEQ ID NO: 8) as primers to amplify the required pGEM3Z sequence in a polymerase chain reaction (PCR). The two oligonucleotide primers were each designed as two sections, the 5' end of the sequences containing restriction sites required for cloning and the 3' end of the sequences specifically matching the sequence of the plasmid pGEM3Z. The 3' end of the oligonucleotide GA179 (SEQ ID NO: 7) is the same as the pGEM3Z nucleotides 452–472 bp (Promega Corp. numbering system) while the 3' end of oligonucleotide GA181 (SEQ ID NO: 8) is complementary to pGEM3Z nucleotides 2254–2240 bp, i.e. they prime opposite strands of the pGEM3Z DNA during the PCR reaction.

The PCR reaction was carried out using 10 ng of pGEM3Z cut with restriction enzyme PvuII to linearized the plasmid, 20 pico moles of each oligonucleotide, 0.03 mM of each of the four deoxynuclotide triphosphates dATP, dTTP, dCTP and dGTP, Taq polymerase buffer (Biores) to a final volume of 50 ul and 1.25 units of Taq polymerase (Biores). The reaction was carried out for eight cycles using 120 second incubations at 95 degrees to denature, 50 degrees to anneal and 72 degrees for the extension reaction. The polymerase was removed from product of the PCR reaction by extracting with phenol, then chloroform and the DNA precipitated with ethanol at −20 degrees. The product of the PCR (which consisted of the pGEM3Z sequence 452–2254 bp flanked by the sequences of the two oligonucleotides GA179 (SEQ ID NO: 7) and GA181) (SEQ ID NO: 8) was then digested with the restriction enzyme BamHI to cleave the BamHI sites at the 5' end of the two oligonucleotides, and then the enzyme removed by extraction with 50% phenol/chloroform, chloroform and then the DNA was precipitated with three volumes of ethanol at −70 degrees. Finally, the DNA product of the PCR reaction was self ligated using the BamHI sticky ends to form intact plasmids and the plasmids transformed into the *E. coli* strain Dh5a(Bethesda Research Laboratories) by electroporation using the procedures recommended by Biorad, the manufacturer of the "Gene pulser" equipment. The transformed cells were spread onto LB agar containing 100 ug ampicillin per ml. *E. coli* clones resistant to ampicillin were selected, their plasmids (e.g. pMUW1410) prepared by alkaline lysis and checked for size and the desired pattern of restriction enzyme sites using agar electrophoresis.

The plasmid pMUW1410 was approximately 1.8 Kb in size as expected for the desired portion of pGEM3Z (452–2254 bP) containing the pBR332 origin of replication and the ampicillin gene. Indeed, the ability of the *E. coli* clone containing pMUW1410 to replicate on ampicillin agar means the plasmid must contain a functional origin of replication and the ampicillin resistance gene. pMUW1410 also contains restriction sites for ClaI, BamHI and NheI derived from the synthetic oligonucleotides. The sequence of the plasmid pMUW1410 in the region of the BamHI site was confirmed using a T7 polymerase sequencing kit (Pharmacia) and a synthetic oligonucleotide GA220 (SEQ ID NO: 9) which is designed to anneal to the ampicillin gene (2149-2164 bp, pGEM3Z numbering) so that the sequencing reaction covers the sequence derived from the oligonucleotides GA179 (SEQ ID NO: 7) and GA181 (SEQ ID NO: 8). The sequencing reaction confirmed that the oligonucleotides GA179 and GA181 used to create pMUW1410 had in fact bound to the expected positions in pGEM3Z and excludes the possibility of errors due to miss-priming at any other position.

pMUW1530

Shuttle vector pMUW1530 was constructed by inserting the XbaI—ClaI fragment (1175-1775 bp) of Ddp2 containing the origin of replication into the NheI and ClaI sites of plasmid pMUW1410.

Plasmid pMUW1015 containing the large AluI (1155-3223 bp) fragment of Ddp2 was used as the source of the Ddp2 origin of replication. 10 ug of pMUW1015 was digested with XbaI and EcoRI restriction enzymes and a 1.2 Kb DNA fragment (i.e. 1175-2436 bp of Ddp2) isolated by agarose gel purification. The appropriate DNA band was excised from the electrophoresis gel and frozen to disrupt the gel matrix. The DNA was extracted using the centrifugation methods of Heery et al ((1990) TIG 6,173.) and then phenol/chloroform extracted and ethanol precipitated to remove traces of the ethidium bromide stain. The DNA was further digested with the ClaI restriction enzyme and the 0.6 Kb XbaI—ClaI fragment (1175-1775 bp, Ddp2 numbering) gel purified as described above.

Plasmid pMUW1410 was digested with the restriction enzyme NheI and subsequently with enzyme ClaI, since the NheI site is too close to the ClaI site to cut efficiently after the ClaI enzyme has cut. The digestion was then dephosphorylated by adding 1/40th volume of 20% SDS, 1/6th volume of 1M Tris buffer pH 9.0 and then 1 unit of Calf intestinal alkaline phosphatase (Boehringer) and incubating at 37 degrees for one hour. The enzyme was then removed by extracting with 50% phenol/chloroform followed by chloroform extraction and then the DNA precipitated with ammonium acetate and two volumes of ethanol.

The XbaI—ClaI fragment from plasmid pMUW1015 (i.e. the Ddp2 origin of replication) prepared above was ligated into the plasmid pMUW1415 (cut with NheI and ClaI and treated with alkaline phosphatase), transformed into the *E. coli* strain "Sure" (Statagene) and plated onto LB agar containing 100 ug ampicillin per ml. *E. coli* clones resistant to ampicillin were selected, their plasmids (e.g. pMUW1530) prepared by alkaline lysis and checked for size and the desired pattern of restriction enzyme sites using agar electrophoresis.

Plasmid pMUW1530 is a 2.4 Kb shuttle plasmid containing the Ddp2 origin of replication inserted into the NheI and ClaI sites of plasmid pMUW1410. Evidence confirming this includes the presence of the BglII and NdeI sites from the Ddp2 origin of replication at the expected distance from the BamHI and ClaI sites found in pMUW1410. pMUW1530 does not contain the XbaI or NheI restriction sites used for cloning since the compatible "sticky ends" were destroyed by the ligation.

5 ug of pMUW1530 mixed with 5 ug of plasmid pMUW110 was then used to transform *D. discoideum* axenic strain, AX3K, using the standard calcium phosphate precipitation procedure with G418 selection. G418 resistant transformants were screened by "lysis in a gel", southern blotting onto Zeta-probe membrane and probed with $^{32}$P labelled pGEM3Z. This demonstrated the presence of an extrachromosomal plasmid with the size of plasmid pMUW1530 containing pGEM3Z DNA sequences.

pMUW1570

Shuttle vector pMUW1570 is the same as pMUW1530, but with the NdeI restriction site removed to allow NdeI to be used for the manipulation of genes cloned into the plasmid.

Plasmid pMUW1530 was digested with the NdeI restriction enzyme in 11 ul of 10 mM Tris buffer pH 7.5, 10 mM MgCl and 50 mM NaCl. The ends of the DNA were then filled by simply adding 1 unit of T7 polymerase and 3 ul of the "C long" mix of deoxynucleotides supplied with the Pharmacia T7 polymerase sequencing kit and incubating at room temperature for five minutes. The plasmid was then religated by adding 2 ul ligation buffer (Boehringer), adjusting the volume to 20 ul by adding water and 1 unit of T4 ligase and then incubating at 4 degrees overnight. The religated plasmid was transformed into the *E. coli* strain "Sure" (Statagene) and plated onto LB agar containing 100 ug ampicillin per ml. *E. coli* clones resistant to ampicillin were selected, their plasmids (e.g. pMUW1570) prepared by alkaline lysis and checked for size and the absence of the NdeI restriction site.

pMUW1580

Shuttle vector as pMUW1580 is the same pMUW1570, but with the BglII restriction site removed to allow BglII to be used for the manipulation of genes cloned into the plasmid.

Plasmid pMUW1530 was digested with the NdeI restriction enzyme, end filled with T7 polymerase, self ligated and transformed into *E. coli* using the same procedures as for pMUW1570. *E. coli* clones resistant to ampicillin were selected, their plasmids (e.g. pMUW1580) prepared by alkaline lysis and checked for size and the absence of the BglII restriction site.

Plasmid pMUW1580 contains a second ClaI site created by end filling the BglII site. However, in most strains of *E. coli* this sequence is methylated so that the ClaI enzyme will not cut the new ClaI site.

5 ug of pMUW1580 was mixed with 5 ug of plasmid pMUW110 and used to transform the *D. discoideum* axenic strain, AX3K, using the standard calcium phosphate precipitation procedure with G418 selection. G418 resistant transformants were screened by "lysis in a gel", southern blotting onto Zeta-probe membrane and probed with $^{32}$P labelled pGEM3Z. This demonstrated an extrachromosomal plasmid with the size of plasmid pMUW1580 containing pGEM3Z DNA sequences. Thus, plasmid pMUW1580 is a small, 2.4 Kb shuttle vector containing the minimum number of six base restriction sites, which is particularly suitable for use in the construction of expression vectors.

EXAMPLE 4

Construction of an Expression Cassette

An "expression cassette" is a single, easily cloned piece of DNA which contains in their correct relative positions all the sequences required to ensure expression of a gene and the correct processing of the messenger RNA and protein product. Usually the cassette contains a number of restriction sites (polylinker) behind the promoter in a good position for inserting the gene to be expressed. The use of a well designed expression cassette greatly facilitates the expression of a range of genes and is much preferred to the alternative of cloning all the necessary DNA sequences on an adhoc basis.

We have designed a novel expression cassette specifically for insertion into the BamHI site of the shuttle vectors pMUW1530, pMUW1570 and pMUW1580. The expression cassette is designed to minimize the amount of unnecessary DNA sequences and restriction sites. This was achieved by cloning the required control and signal sequences using PCR techniques to insert at key positions the restriction sites required for cloning, using sites that can be destroyed during the construction procedure. The cassette contains a promoter from the *D. discoideum* actin 15 gene, a sequence coding for a secretion signal peptide, a polylinker containing restriction sites allowing the insertion of genes for expression and a polyadenylation signal sequence from the *D. discoideum* actin 15 gene.

Each component section of the expression cassette was cloned separately and then assembled into the complete cassette inside the polylinker of pGEM3Z.

Cloning the Actin 15 Promoter, Plasmid pMUW1480

The actin 15 promoter was selected because it is well characterised and is known to be expressed at a relatively high level soon after the onset of starvation (Cohen et al (1986) EMBO J. 5, 3361-3366). For the purpose of the production of recombinant proteins, this pattern of expression is desirable to avoid the protein being produced during active growth where the resulting metabolic drain may cause a selective advantage for any non-secreting mutants.

The two synthetic oligonucleotides GA190 (SEQ ID NO: 10) and GA188 (SEQ ID NO: 11) were used as primers to amplify the required actin 15 promoter sequence in a polymerase chain reaction (PCR). The two oligonucleotide primers were each designed as two sections, the 5' end of the sequences containing restriction sites required for cloning and the 3' end of the sequences specifically matching the sequence of the Actin 15 gene in plasmid pTS1 (Chang et al (1989) Nucleic Acids Res. 17, 3655-3661). The 3' ends of the oligonucleotide GA190 (SEQ ID NO: 10) is the same as the promoter nucleotides between −247 and −230 (numbering back from A of the ATG start codon) while the 3' end of oligonucleotide GA188 (SEQ ID NO: 11) is complementary to nucleotides between +3 and −13, i.e. they prime opposite strands of the actin 15 DNA during the PCR reaction.

The PCR reaction was carried out using 30 ng of pTS1 cut with restriction enzymes PvuII and ScaI to ensure the plasmid is unable to replicate during later cloning steps, 20p moles of each oligonucleotide, 0.03 mM of each of the four deoxynucleotide triphosphates dATP, dTTP, dCTP and dGTP, Taq polymerase buffer (Biores) to a final volume of 50 ul and 1.25 units of Taq polymerase (Biores). The reaction was carried out for ten cycles using 120 second incubations at 95 degrees to denature, 40 degrees to anneal and 72 degrees for the extension reaction. At the end of the PCR reaction, 1 unit of T4 polymerase was added and incubated at room temperature for 15 minutes to ensure the ends of the DNA were blunt. 20 ug of glycogen in 1 ul (Boehringer) was added and 2 ul of acetate buffer (to aid precipitation of the small DNA fragments) before the polymerases were removed by extracting with 50% phenol in choroform, then chloroform and the DNA precipitated with three volumes of ethanol at −70 degrees.

The product of the PCR reaction (consisting of the Actin 15 promoter sequence between −247 and +3 relative to the start codon flanked by the sequences of the two oligonucleotides GA190 (SEQ ID NO: 10) and GA188 (SEQ ID NO: 11)) was shown to have the expected size of approximately 300 bp by electrophoresis in 1.6% agarose against size markers (BRESA) of phage SPP-1 digested with the restriction enzyme EcoRI.

The DNA product of the PCR reaction was mixed with 100 ng of pGEM3Z which had been cut with the restriction enzyme SmaI to create blunt ends. The mixture was ligated with 3 units of T4 ligase in ligation buffer for two hours at room temperature and then precipitated with ammonium acetate and two volumes of ethanol. The religated plasmids were transformed into the *E. coli* strain Dh5a (Bethesda Research Laboratories) by electropotation using the procedures recommended by Biorad, the manufacturer of the "gene pulser" equipment. The transformed cells were plated onto LB agar containing 100 ug ampicillin per ml, 0.5 mM IPTG (isopropyl-B-d-thiogalactopyanoside) and 50 ug X-Gal (5-bromo-4-chloro-3-indolyl-B-galactoside) per ml. *E. coli* clones resistant to ampicillin and producing large white colonies (indicating the plasmid has DNA inserted into the polylinker) were selected, their plasmids (e.g. pMUW1480) prepared by alkaline lysis and checked for size and the desired pattern of restriction enzyme sites using agar electrophoresis.

The plasmid pMUW1480 digested by the restriction enzyme PvuII produced a fragment with approximately of 700 bp, comprised of 379 bp of pGEM3Z sequences containing an approximately 300 bp insert, as expected for the desired actin 15 promoter (250 bp) flanked by the sequences derived from the synthetic oligonucleotides GA190 (SEQ ID NO: 10) and GA188 (SEQ ID NO: 11). pMUW1480 also contains restriction sites for HindIII, BglII, NsiI and FokI derived from the synthetic oligonucleotides. The identity of the promoter inserted into plasmid pMUW1480 was confirmed by sequencing using a T7 polymerase sequencing kit (Pharmacia) and commercially supplied oligonucleotides (Promega) which anneal to SP6 and T7 regions flanking the polylinker. The sequencing excludes any possibility of errors in the sequence.

Cloning a Sequence for a Secretion Signal, Plasmid pMUW1450

Secretion of a protein requires a signal sequence at the amino terminal end of the polypeptide. This signal peptide is the first part of the protein to be transcribed and causes the ribosome to bind to the endoplasmic reticulum membranes and feed the nascent polypeptide across the membrane into the lumen of endoplasmic reticulum. Subsequently, the signal peptide is cleaved from the rest of the protein.

The *D. discoideum* protein PsA possesses a 20 amino acid signal peptide which has characteristics typical of many eukaryotic signal peptides (Perlman & Halvorson (1983) J. Mol. Bio. 167, 391-409) and so it should be a reliable signal to use of the secretion of recombinant proteins.

The two synthetic oligonucleotides GA187 (SEQ ID NO: 12) and GA182 (SEQ ID NO: 13) were used as primers in a PCR reaction to amplify the DNA sequence coding for the PsA signal peptide from the D19 gene encoding the PsA protein (Early et al (1988) Mol.

Cell. Biol. 8, 3458–3466). The methods used were the same as described for cloning the actin 15 promoter (see above). However, some difficulty occurred in cloning the correct product of the PCR reaction.

The plasmid pMUW1450 gave the correct size fragment when digested by the restriction enzyme PvuII, but when the insert was sequenced it was found that the oligonucleotide GA182 (SEQ ID NO: 13) had not annealed to the D19 DNA in the anticipated position at the 3' end of the signal sequence. The DNA cloned in plasmid pMUW1450 contained the first oligonucleotide GA187 (SEQ ID NO: 12) in the correct position 5' to the D19 start codon, but the DNA sequence continued past the end of the signal peptide as far as the PvuII site near the center of the gene. Investigation of the reason for the failure of the oligonucleotide GA182 to prime the PCR reaction correctly established that this sequence forms a hair pin loop, so it was unlikely to be available for binding to the D19 gene.

An alternative approach to modifying the 3' end the DNA coding for the PsA signal peptide is described below.

Fusion of the Promoter with the D19 (PsA) gene, Plasmid pMUW1545

Plasmid pMUW1450 contains the restriction sites derived from oligonucleotide GA187 that are required for the promoter and D19 gene sequences to be fused. This required a three way ligation to force clone the two DNA fragments into the NdeI and HindIII sites of pGEM3Z.

The DNA fragments to be fused were prepared by cutting 5 ug of plasmid pMUW1450 with the restriction enzymes NdeI and ScaI and then purifying the largest (1.8 Kb) DNA fragment containing the D19 sequences by gel purification as described previously. The NdeI cleavage site at the end of this fragment occurs within the D19 sequence coding for the signal peptide. The promoter sequence was prepared by cutting 5 ug of plasmid pMUW1480 with the HindIII and EcoRI restriction enzymes, which cut the HindIII site in oligonucleotide GA190 (SEQ ID NO: 10) derived sequence 5' to the promoter and the EcoRI site in the polylinker, yielding a 0.3 Kb fragment which was then purified by gel electrophoresis. The DNA fragments containing the D19 and promoter fragments were mixed together and digested with the FokI restriction enzyme which creates compatible ends at the ATG start codons in both sequences. The FokI digested fragments were extracted with 50% phenol in chloroform, then chloroform and then precipitated with three volumes of ethanol at −70 degrees. The FokI fragments were ligated with 0.5 ug of pGEM3Z which has been cut with HindIII and NdeI, treated with alkaline phosphatase and purified by gel electrophoresis as described for plasmid pMUW1410. The religated plasmids were transformed into the E. coli "Sure" strain as described above and plated onto LB agar containing 100 ug ampicillin per ml. E. coli clones resistant to ampicillin were selected, their plasmids (e.g. pMUW1545) prepared by alkaline lysis and checked for the presence of the BglII restriction site from the oligonucleotide GA190 (SEQ ID NO: 10), and the absence of the NsiI restriction sites that should have been removed from both of the inserted fragments.

Construction of the Full Promoter/Signal Sequence, pMUW1594

In order to replace the 3' end of the D19 sequence coding for the signal peptide a synthetic DNA sequence was cloned into the NdeI restriction site of plasmid pMUW1545. The synthetic DNA sequence is composed of two synthetic oligonucleotides GA297 (SEQ ID NO: 14) (+ve strand) and a complementary sequence GA296 (SEQ ID NO: 15) (−ve stand) which anneal to form double stranded DNA with ends compatible with the NdeI restriction site. In designing these oligonucleotides, the opportunity was taken to change the DNA sequence to optimize the codon usage for highly expressed genes, remove the potential to form hair pin loops and to remove the NdeI restriction site used to insert the oligonucleotides, leaving a single NdeI site suitable for cloning at the signal peptide cleavage site. The DNA sequence changes do not alter the encoded amino acid sequence of the signal peptide.

The oligonucleotide GA297 (SEQ ID NO: 14) and GA296 (SEQ ID NO: 15) were phosphorylated with T4 kinase. 50p moles of each oligonucleotides in 50 ul "One-for-all" buffer (Pharmacia) and 2 uM dATP was incubated with 20 units T4 ligase at 37 degrees for 30 minutes and then the enzyme destroyed by heating to 100 degrees.

Plasmid pMUW1545 was linearized with NdeI restriction enzyme and ligated with 1 p mole of phosphorylated oligonucleotides GA297 and GA296 using 0.5 units of T4 ligase at 4 degrees overnight. The religated plasmids were transformed into the E. coli strain "Sure" (Statagene) and after one hour incubation at 37 degrees the organisms were inoculated into 500 ml LB broth containing 100 ug ampicillin per ml. After being shaken for 18 hours at 37 degrees, the cells were harvested and the mixed population of plasmids purified by alkaline lysis. 5 ug of the resulting mixture of plasmids were digested with the Hind III restriction enzyme and an approximately 0.3 Kb fragment of DNA purified by gel electrophoresis as described above. This 0.3 Kb fragment of DNA could only come from plasmids that are cut in the polylinker and also have the synthetic DNA sequence (which contains a second HindIII site) inserted into the NdeI restriction site of pMUW1545. Thus, this 0.3 Kb fragment contains the full promoter signal sequence construct.

The 0.3 Kb promoter—signal sequence was ligated into pGEM3Z that had been cut with HindIII, treated with alkaline phosphatase and purified by gel electrophoresis. The religated plasmid were transformed into the E. coli strain "Sure" (Statagene) and plated onto LB agar containing 100 ug ampicillin per ml. E. coli clones resistant to ampicillin were selected and their plasmids (e.g. pMUW1594) prepared by alkaline lysis. Plasmids were checked for size and the correct orientation of the promoter (i.e. 5' to the polylinker) using the position of the BglII site 5' to the promoter. Clones were further screened by T7 polymerase sequencing (Pharmacia) using oligonucleotide GA187 (SEQ ID NO: 12) to check the orientation of the inserted synthetic DNA sequence. Plasmid pMUW1594 had the required promoter and signal sequence in frame with the pGEM3Z polylinker encoded lac operon sequences.

Cloning the Actin 15 Polyadenylation Signal, Plasmid pMUW1512

The two synthetic oligonucleotides GA189 (SEQ ID NO: 16) and GA186 (SEQ ID NO: 17) were used as primers to amplify the actin 15 polyadenylation sequence in a polymerase chain reaction (PCR). The two oligonucleotide primers were each designed as two sections, the 5' end of the sequences containing restrictions sites required for cloning and the 3' end of the sequences specially matching the sequence of the Actin 15 gene in plasmid pTS1 (Chang et al (1989) Nucleic Acids Res. 17, 3655–3661). The 3' end of the oligonucleotide GA189 is designed to bind at the stop codon of the actin 15 gene and has one extra base pair added to the original sequence in order to place stop codons in all three reading frames, while the 3' end of oligonucleotide GA186 (SEQ ID NO: 17) is complementary to the sequence approximately 305 bp 3', immediately preceding a EcoRV restriction site. The oligonucleotide GA186 replaces the EcoRV restriction site with BglII and EcoRI site for use in cloning.

The PCR amplification of the polyadenylation sequence was carried out using the identical DNA preparations and methods to the cloning of the actin 15 promoter described above, apart from the use of a different pair of oligonucleotides and the transformation of the plasmids into the "Sure" strain of E. coli. The plasmids produced (e.g. pMUW1512) were digested by the restriction enzyme PvuII and screened for the presence of a fragment of approximately 800 bp, comprised of 379 bp of pGEM3Z sequences containing an approximately 400 bp insert. The plasmids were further digested with the restriction enzymes BglII, EcoRI and KpnI (separately) to check for the presence of the restriction sites from the two oligonucleotides. Plasmids pMUW1512 and pMUW1515 (opposite orientations of the insert) were sequenced to confirm the polyadenylation signal contained no errors using a T7 polymerase sequencing kit (Pharmacia) and commercially supplied oligonucleotides (Promega) which anneal to SP6 and T7 regions flanking the polylinker.

5 ug of plasmid pMUW1512 was digested with KpnI and subsequently with EcoRI restriction enzymes and an approximately 0.4 Kb fragment containing the polyadenylation signal purified by gel electrophoresis as described previously. This 0.4 Kb fragment was ligated into 1 ug of plasmid pGEM32 which was also digested with KpnI and EcoRI, treated with alkaline phosphatase and then purified by gel electrophoresis. The plasmids were transformed into E. coli strain "Sure" plated onto LB agar containing ampicillin as described previously. Plasmids (e.g. pMUW1560) from the ampicillin resistant clones were screened for the correct sized insert (0.4 Kb) and the presence of a BglII site derived from oligonucleotide GA186 (SEQ ID NO: 17). Plasmid pMUW1560 contains the actin 15 polyadenylation signal in the correct position and orientation for the final expression cassette.

Construction of the Complete Expression Cassette, Plasmid pMUW1621

The expression cassette was completed in a single cloning step combining the fused promoter/signal sequence from plasmid pMUW1594 with the polyadenylation sequence from plasmid pMUW1560.

Plasmid pMUW1560 was digested with the restriction enzymes SalI and ScaI and the smaller 1.2 kG Kb fragment containing the polyadenylation signal purified by gel electrophoresis as previously described. Plasmid pMUW1594 was also digested with SalI and ScaI enzymes and the larger 2 Kb fragment containing the promoter and signal sequence purified by gel electrophoresis. The two fragments were pooled, ligated and transformed into the "Sure" strain of E. coli. The identity of the isolated plasmids (e.g. pMUW1621) was confirmed by cutting with the restriction enzyme BglII to produce a 0.7 Kb fragment. This fragment can only be produced by plasmids containing two BglII sites, one derived for the oligonucleotide GA190 (SEQ ID NO: 10) used to clone the promoter and the second derived from oligonucleotide GA186 (SEQ ID NO: 17) used to clone the polyadenylation signal.

Insertion of the Expression Cassette into the Shuttle Vector

The shuttle vector pMUW1580 was linearized using restriction enzyme BamHI, treated with alkaline phosphatase and purified by gel electrophoresis as previously described. The expression cassette in the 0.7 Kb BglII fragment from plasmid pMUW1621 was also purified by gel electrophoresis and ligated into the linearized plasmid pMUW1580. The ends of the DNA fragments produced by the BglII and BamHI enzymes are compatible, so both restriction sites are destroyed in the ligation. The resulting plasmids produced in the E. coli "Sure" strain were digested with ClaI and HindIII enzymes to screen for the presence of the polylinker in the expression cassette and the orientation of the expression cassette in the plasmid. Plasmids pMUW1630 and 1633 had the opposite orientations of the expression cassette.

Insertion of the GUS Gene into the Expression Vector

The GUS gene is the E. coli gene for the enzyme B-glucuronidase which has been modified by the insertion of SalI and NcoI restriction enzyme sites at the start codon of the gene, an EcoRI site at the 3' end of the gene and a BamHI site removed from the center of the gene (Jefferson et al (1986) PNAS 83, 8447). Plasmid pRAJ275 containing this construct was purchased from Clontech Laboratories Inc., California, USA.

In order that the GUS gene could be easily sequenced, it was inserted into pGEM3Z. The GUS gene was cut out of plasmid pRAJ175 with the restriction enzymes SalI and EcoRI, purified by gel electrophoresis and ligated into plasmid pGEM3Z which had been cut with the same enzymes, treated with alkaline phosphatase and gel purified. The plasmid with the GUS gene inserted was pMUW1550.

A SmaI restriction site was inserted into the EcoRI site of plasmid pMUW1550 using oligonucleotide GA310 (SEQ ID NO: 18) as a linker. Oligonucleotide GA310 was phosphorylated as previously described in the section on the construction of the full promoter/signal sequence. 1 pmole of phosphorylated GA310 (SEQ ID NO: 18) was mixed with 0.5 ug of plasmid pMUW1550 which had been cut with the EcoRI restriction enzyme and purified by gel electrophoresis. The mixture was ligated at 4 degrees overnight and then transformed into the E. coli "Sure" strain. The transformants were incubated for one hour in SOC medium and then inoculated into 50 ml of LB broth containing 100 ug ampicillin per ml. After shaking at 37 degrees for 18 hours the cells were harvested, plasmids purified and cut with the SmaI restriction enzyme. Only the plasmids containing the oligonucleotide GA310 (SEQ ID NO: 18) contain a SmaI site, so the linearized plasmids were purified by gel electrophoresis, religated and transformed back into the E. coli strain "Sure".

1 ug of plasmid pMUW1558 containing a the GUS gene with the SmaI restriction site inserted into the EcoRI site at the 3' end of the gene was cut with the restriction enzymes SalI and SmaI and the 1.9 Kb gene purified by gel electrophoresis. The polylinker in the expression vector pMUW1630 was also cut with the restriction enzymes SalI and SmaI, treated with alkaline phosphatase and purified by gel electrophoresis. The two purified DNA fragments were ligated, transformed into the "Sure" strain of E. coli and plasmids purified from ampicillin resistant clones. Plasmid pMUW1653 contained the GUS gene cloned in frame into the SalI site of the expression vector. This was confirmed by restriction mapping using the sites for NcoI and EcoRI enzymes at the 5' and 3' ends of the GUS Gene respectively. The region of the fusion between the sequence encoding the secretion signal and the 5' end of the GUS gene sequencing plasmid was confirmed by DNA sequencing using a T7 polymerase kit (Pharmacia) and oligonucleotide GA187 (SEQ ID NO: 12).

Expression of the GUS gene in *D. discoideum*

The suitability of the expression vector for the expression of recombinant genes was confirmed by transforming 5 ug of the expression plasmid pMUW1653 (containing the E. coli B-glucuronidase gene) and 5 ug of plasmid pMUW110 (containing the Ddp2 Rep gene and a G418 resistance marker) into *D. discoideum* strain AX3K using the calcium phosphate precipitation procedure described previously. After one week under G418 selection, the culture supernatant from the transformants was tested for the presence of the GUS enzyme activity using 1 mM p-nitrophenyl-B-D glucuronide substrate in 50 mM sodium phosphate pH7.0, 10 mM 2-mercaptoethanol and 0.1% Triton X-100. A green colouration indicated the presence of the enzyme B-glucuronidase secreted from *D. discoideum*. Culture supernatants from cells transformed with the expression vector pMUW1630 did not contain B-glucuronidase.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:
1. A method of producing a desired polypeptide comprising the following steps:
   a) preparing a recombinant plasmid vector comprising an origin of replication from plasmid Ddp2 or pDG1 and a DNA sequence encoding the desired polypeptide, wherein plasmid Ddp2 or pDG 1 and a DNA sequence encoding the desired polypeptide, wherein said plasmid vector lacks DNA sequences encoding a Rep protein required for extrachromosomal replication in wild type Dictyostelium;
   b) preparing a recombinant strain of Dictyostelium comprising a gene encoding a Rep polypeptide which allows replication of the recombinant plasmid of step (a);
   c) transforming the recombinant Dictyostelium of step (b) with the recombinant plasmid vector of step (a);
   d) culturing the transformed Dictyostelium of step (c) under conditions which allow expression of the DNA sequence encoding the desired polypeptide; and
   e) recovering the desired polypeptide.

2. A method as claimed in claim 1 in which the desired polypeptide is produced in a cell bound form.

3. A method as claimed in claim 1 in which the gene encoding the Rep-polypeptide is present on the chromosome of the recombinant strain.

4. A method of producing a desired polypeptide comprising the following steps:
   a) preparing a recombinant plasmid vector comprising an origin of replication from plasmid Ddp2 or pDG1 and a DNA sequence encoding the desired polypeptide, wherein said plasmid vector lacks DNA sequences encoding a Rep protein required for extrachromosomal replication in wild type Dictyostelium;
   b) preparing a recombinant plasmid vector comprising a gene encoding a Rep polypeptide which allows replication of the recombinant plasmid of step (a);
   c) preparing a recombinant strain of Dictyostelium by transformation of Dictyostelium with the recombinant plasmid vectors of steps (a) and (b);
   d) culturing the transformed Dictyostelium of step (c) under conditions which allow expression of the DNA sequence encoding the desired polypeptide; and
   e) recovering the desired polypeptide.

5. A recombinant strain of Dictyostelium which harbours a recombinant plasmid, said recombinant plasmid comprising an origin of replication from plasmid Ddp2 or plasmid pDG1, said plasmid lacking a functional Rep gene required for extrachromosomal replication in wild type Dictyostelium, said recombinant strain comprising a chromosomally located gene encoding a Rep polypeptide which allows replication of said recombinant plasmid.

6. A recombinant strain of Dictyostelium as claimed in claim 5 in which the Rep polypeptide has an amino acid sequence as shown in FIG. 2 (SEQ ID NO: 3).

7. A recombinant strain of Dictyostelium as claimed in claim 5 in which the gene encoding the Rep polypeptide has a DNA sequence as shown in FIG. 1 (SEQ ID NO: 2) from nucleotide 2378 to nucleotide 5038.

8. A recombinant strain of Dictyostelium as claimed in claim 5 in which the gene encoding the Rep polypeptide has a DNA sequence as shown in FIG. 1 (SEQ ID NO: 2) from nucleotide 1885 to nucleotide 5292.

9. A recombinant plasmid vector comprising an origin of replication from plasmid Ddp2 or plasmid pDG1 and at least one heterologous DNA sequence, said heterologous DNA sequence encoding a desired polypeptide and at least one promoter sequence that controls expression of said desired polypeptide, wherein said plasmid vector lacks DNA sequences encoding a Rep protein required for extrachromosomal replication in wild type Dictyostelium.

10. A recombinant plasmid as claimed in claim 9 in which the heterologous DNA sequence includes a DNA sequence encoding a polypeptide signal for secretion of the desired polypeptide.

11. A recombinant plasmid vector as claimed in claim 9 in which the recombinant plasmid vector includes an expression cassette comprising a promoter DNA sequence from Dictyostelium Actin 15 gene, a DNA sequence encoding the secretion signal peptide sequence of the D19 gene of the protein PsA and a DNA signal sequence for RNA polyadenylation from the Actin 15 gene.

12. Recombinant plasmid vector pMUW102.
13. Recombinant plasmid vector pMUW111.
14. Recombinant plasmid vector pMUW110.
15. Recombinant plasmid vector pMUW130.
16. Recombinant plasmid vector pMUW1530.
17. Recombinant plasmid vector pMUW1570.
18. Recombinant plasmid vector pMUW1580.
19. Recombinant plasmid vector pMUW1630.
20. Recombinant plasmid vector pMUW1633.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:1:

TGTCATGACA    10

( 2 ) INFORMATION FOR SEQ ID NO:2:

( i ) SEQUENCE CHARACTERISTICS:
        ( A ) LENGTH: 5852 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( i x ) FEATURE:
        ( A ) NAME/KEY: CDS
        ( B ) LOCATION: 2378..5038

( i x ) FEATURE:
        ( A ) NAME/KEY: CDS
        ( B ) LOCATION: 2378..5038

( x i ) SEQUENCE DESCRIPTION: SEQ ID NO:2:

TCGACAAATA  TCAAGGGTTG  GAATCTTGTA  AAAATTTTCC  CGTTATCGCA  AACAATCAAA    60

GTTTAAGCTT  CAATCTTCAA  TAATAATTTT  AACTTTATCT  CTTTCAATTT  TAATAATTTT    120

```
TTTCAAAAAT  TGAAAATGGT  ATAGATCGAT  AGATCACCTT  TTTTAGAGAT  AAACCATGAA   180
AAAGACATAA  AAAATAAAGG  TCATCAAAGT  ATTAAAAAAA  ATTAATTATC  TTTTTAACTT   240
TGAAAAAAAA  AAATAAAAAA  AAATAAAAAA  AAAAAATTCT  TTGTTTTAAT  AACTTTTAAA   300
ATTATTAAAA  ATAGTATAGA  TTTAAAGATC  ACAATTTTTT  ATAATTAACT  ACATAAAATT   360
TATAAAAAAT  GAGGGTCATG  AAGATATATA  ATAATTATT   TAATTATTAA  ATATTTAATT   420
ATTTATTTAA  CTTAAAAAAA  AAAAAAGGA   AAAAAGGAA   AAAAAAGTG   AAAAGGTGG    480
GAAATGAAA   AAAAAGTGA   AAAAATGCC   CAAAAAATT   TTTATATGAG  AAAAAAATTA   540
CGTAAAAAAA  AAATAAGTCT  GACCCAAATC  GAAAAATAAT  AAAAGAGGGG  AAAGTAATTA   600
TAACTAGGTT  AGTTTTTTAT  AATTTTTACA  TATTTGTTAA  TAACTTTTAA  TTTTGAATCA   660
TATGATATTA  CATCGTCCCG  TTGAAAAAAA  AAAAAAAAAT  TTTTTTTTCA  AACATTTTCA   720
TTTTTTAAAA  AATGATATAA  AATTTTAAAC  TAAACTATTT  TATTAAATAC  AAATATATAA   780
CTTTATCTTA  ATCAATTTTT  TTGGTTTATA  CATATTTATG  TTCGTACTGA  AGTATAGATC   840
TTATTACTAA  AGTTCAAAA   GTTTTAAAAA  AAATTAAAGG  GGGTAAATAT  ATAACTTTCT   900
GTTTTTTTCA  ATTCTGTCAT  GACAGAAAGG  TAAAAGTGT   CATGACAAAA  AAAAAAAAA    960
AAAAAATTTA  TTTCTTCAAT  AGGTATTGAA  ATGACCTCCG  TTTTAATAA   AAGTATATA   1020
TTTGTGCTTT  CCTAGATGAA  ATAAGGTTAT  TTGAGCTTAA  TTCAGATTAT  TATAAGATTA  1080
TTATAAAAAA  ATGAAAAACT  GTCATGACAG  TTTTTGTAAG  TTTCTTATAG  TTTTTTTTAA  1140
TGATCTGAAT  TAAGCTTAAA  TAACCTTATT  TCATCTAGAC  GAGCACAAAT  ATATACTTTT  1200
TATTAAAAAC  GGAGGTCATT  TCAATACCTA  TTGAAGAAAT  AAATTTTTT   TTTTTTTTT   1260
TTTGTCATGA  CACTTTTTTT  TTTTTGTCAT  GACAGAATTG  AAAAAAACAG  AAAGTTATAT  1320
ATTTACCCCC  TTTAATTTTT  TTTAAAACTT  TTGAAACTTT  AGTAATAAGA  TCTATACTTC  1380
AGTACGAACA  TAAATATGTA  TAAACCAAAA  AAATTGATTA  AGATAAAGTT  ATATGTTTGT  1440
ATTTAATAAA  ATAGTTTAGT  TTAAAATTTT  ATATCATTTT  TTAAAAAATG  AAAATGTTTG  1500
AAAAAAAAAA  TTTTTTTTTT  TTTTTCAAC   GGGACGATGT  AATATCATAT  GATTCAAAAT  1560
TAAAAGTTAT  TAACAAATAT  GTAAAATTA   TAAAAAACTA  ACCTAGTTAT  AATTACTTTC  1620
CCCTCTTTTT  TTTTTTTTTT  TTTGTCATGA  CACTTTTTTT  TTTTGTCAT   GACACTTTTT  1680
TTTTAAAAAA  AAAAAAAAAA  ATGTTAAAAT  ACTATTTGAT  GACATTCATT  TTTCCTAGTT  1740
TTTTTTTAGA  TAGATATAAA  AATAAATTGC  CTATCGATAT  ATACTTAATT  TATTAAGATT  1800
GAATAATATT  TTAATTTTTA  ATAAATTCTA  CTTTTTTTTT  TTTTTCTTT   TTTTTTAAA   1860
TTTTAAAATT  TTTTTTTTTT  ATTAGATCTC  ATAATTAAAA  ATCAATTTAA  AATTAAAAGT  1920
TATTTTTAAA  TATGCAAAAA  CTATAAAAAA  CTAATGTAGT  TTAACCAACT  TTTTCTATT   1980
TCTTTTTTTT  TTTTTTTTT   TTTTTACTT   TGAAAAAAAA  AAAAAAAAA   AAAAAAAAA   2040
AAACCCTCAT  TATAAATATT  AATTACTTTG  GTTTTTTTG   ATTTTTTTT   TAATAAATTT  2100
AAAATTTTAT  TCTCTATCTA  ATTATACCTT  ATTTATAAAT  ATTGGATAAT  ATATCAAATA  2160
TTTATCAGTT  TTGGCATGAC  AATTTTAATT  ATATTTATTT  TTGATTAAT   TTTTTTTTT   2220
TTTTTTTTTT  AAAATTCTT   TTTTTTTTTT  TTATTTTTA   ATTTTAATT   TTATTTTTC   2280
CCACACTTTC  ATTTATTTT   ATTTATTTA   TTGTAAATTC  ATTTTATTTA  TTTTAATTA   2340
AATAGTTTTG  GTTTAATTTT  ATTCAAAGAT  TTTAAAA ATG GAC GAA CTT ATT TCT    2395
                                        Met Asp Glu Leu Ile Ser
                                          1               5

TGG GAT AGG TTT TTT AAG TTT TTT GTA ATA CTT TTG GAA GAA TTC AAA        2443
Trp Asp Arg Phe Phe Lys Phe Phe Val Ile Leu Leu Glu Glu Phe Lys
         10                  15                  20
```

```
GGT TGT AAA AGA AAT GAT GTG CGT TTG AGT GTC GAT TAT GAC ATT CTT          2491
Gly Cys Lys Arg Asn Asp Val Arg Leu Ser Val Asp Tyr Asp Ile Leu
        25                  30                  35

TCT GGT ATT TAT TCG CCA CGT ACA TTT GTA CTA AAG GAA GTC TTT AGA          2539
Ser Gly Ile Tyr Ser Pro Arg Thr Phe Val Leu Lys Glu Val Phe Arg
    40                  45                  50

GCA GTG GCC GTC TCT TAT GAT GAA TCT GAA ATA GAT TTA TTC AGA TTG          2587
Ala Val Ala Val Ser Tyr Asp Glu Ser Glu Ile Asp Leu Phe Arg Leu
55                  60                  65                  70

GGT TCA GTG TTT CCT GGT ACT TCT TTA TAT TCA TAT ATT CCA GGT ATT          2635
Gly Ser Val Phe Pro Gly Thr Ser Leu Tyr Ser Tyr Ile Pro Gly Ile
            75                  80                  85

TTC AGT TTA AAA GAT TTC CTT TTA ATT TCA AAA ACT AAA TCG GGT AAA          2683
Phe Ser Leu Lys Asp Phe Leu Leu Ile Ser Lys Thr Lys Ser Gly Lys
        90                  95                 100

ATA AGA GTT TCG GAT GTA GAT CAA GCA ATA TTA ATT TTT GAT CAT TTT          2731
Ile Arg Val Ser Asp Val Asp Gln Ala Ile Leu Ile Phe Asp His Phe
    105                 110                 115

TCT AGA ATT TCA GAT AAA CAA GTA TTT CGT AAA GAT ATT ATT CCA GGT          2779
Ser Arg Ile Ser Asp Lys Gln Val Phe Arg Lys Asp Ile Ile Pro Gly
120                 125                 130

TAT AGA ACC TTT GAA AAA TCA ATA TCG AGC GAG TAC AAA ATC TCG GAT          2827
Tyr Arg Thr Phe Glu Lys Ser Ile Ser Ser Glu Tyr Lys Ile Ser Asp
135                 140                 145                 150

GGT CGT GCT GCA GGA GTG AGT TGG TTC AAT TTA GTT AGT AAA ATA AGC          2875
Gly Arg Ala Ala Gly Val Ser Trp Phe Asn Leu Val Ser Lys Ile Ser
            155                 160                 165

ACT TAT TGT AAA AAT CAT CCC TTG TTT GCC GAA AAT CCA ACA TAT AAA          2923
Thr Tyr Cys Lys Asn His Pro Leu Phe Ala Glu Asn Pro Thr Tyr Lys
        170                 175                 180

CAT GTG GAT TTT ATA TCA ATG TTA TCA CTG GTG CAT GGA ATC ATT GTT          2971
His Val Asp Phe Ile Ser Met Leu Ser Leu Val His Gly Ile Ile Val
    185                 190                 195

GAT TCC CAA AAT GAA GAT GAG AAT AAT GTT TCG GCA ATG TAC TCT CTG          3019
Asp Ser Gln Asn Glu Asp Glu Asn Asn Val Ser Ala Met Tyr Ser Leu
200                 205                 210

AAT CCT TTT GTG GAT CTT GAA AAA AGT GAT ATA CCA GGG GCT GTT CAA          3067
Asn Pro Phe Val Asp Leu Glu Lys Ser Asp Ile Pro Gly Ala Val Gln
215                 220                 225                 230

AGT AGA GTT ACT ACA AAT AGA ACT AGA GGT TCA AGG TCT AAT TCC AAT          3115
Ser Arg Val Thr Thr Asn Arg Thr Arg Gly Ser Arg Ser Asn Ser Asn
            235                 240                 245

TTG AAT AAT CCA ACA ACA ACA ACA ACT ACT ACT ACC ACT ACA ACT              3163
Leu Asn Asn Pro Thr Thr Thr Thr Thr Thr Thr Thr Thr Thr Thr
        250                 255                 260

ACC GCA CCA ATT ACT ACT AGA AGT AAA AGA AAA TCT GAC GAC TCT GTA          3211
Thr Ala Pro Ile Thr Thr Arg Ser Lys Arg Lys Ser Asp Asp Ser Val
    265                 270                 275

CAA GAA CAA AGC TCA CGA CAA CCA AAA ACC TCG AGA AAG TCT GGT TCT          3259
Gln Glu Gln Ser Ser Arg Gln Pro Lys Thr Ser Arg Lys Ser Gly Ser
280                 285                 290

CTT AAG GAT GTC AGA ATT AAC AAT ATA TCA GTA GAT TCA AGT TCC AGT          3307
Leu Lys Asp Val Arg Ile Asn Asn Ile Ser Val Asp Ser Ser Ser Ser
295                 300                 305                 310

GAA TCT GAT GTG ATT ATG TCA GTT TCA AAC CGT TTA AAA TGT TAT CTT          3355
Glu Ser Asp Val Ile Met Ser Val Ser Asn Arg Leu Lys Cys Tyr Leu
            315                 320                 325

TTG GAA GCA GTT GTA AAC AAA GGA GAG ATC GGT TTA GAA GTC GTC AAA          3403
Leu Glu Ala Val Val Asn Lys Gly Glu Ile Gly Leu Glu Val Val Lys
        330                 335                 340

GAA GTT TTA AAA GAT TTA CAG GAC AAA AAT TAT GCC ACA GGT TTA CTT          3451
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Glu | Val | Leu | Lys | Asp | Leu | Gln | Asp | Lys | Asn | Tyr | Ala | Thr | Gly | Leu | Leu |      |
|     |     | 345 |     |     |     |     | 350 |     |     |     |     | 355 |     |     |     |      |
| GAA | AAC | ATT | TTC | AAT | CAC | AAC | AAG | TCT | GAA | AGG | GTC | ATA | ACA | CTT | TCA | 3499 |
| Glu | Asn | Ile | Phe | Asn | His | Asn | Lys | Ser | Glu | Arg | Val | Ile | Thr | Leu | Ser |      |
|     | 360 |     |     |     |     | 365 |     |     |     |     | 370 |     |     |     |     |      |
| AGT | AGT | TTT | TTT | GAA | ATT | GCT | TCA | AAA | ATT | AAC | TAT | GAT | GAA | GTT | AAG | 3547 |
| Ser | Ser | Phe | Phe | Glu | Ile | Ala | Ser | Lys | Ile | Asn | Tyr | Asp | Glu | Val | Lys |      |
| 375 |     |     |     | 380 |     |     |     |     | 385 |     |     |     |     |     | 390 |      |
| TTC | AGT | GAA | CTC | AGT | ATT | GAT | GTT | CTG | GAA | TCG | GCA | AAG | AGA | TTA | ACA | 3595 |
| Phe | Ser | Glu | Leu | Ser | Ile | Asp | Val | Leu | Glu | Ser | Ala | Lys | Arg | Leu | Thr |      |
|     |     |     |     | 395 |     |     |     |     | 400 |     |     |     |     | 405 |     |      |
| TTC | GAG | AAA | AAT | ACA | AAT | ATA | TTA | ATT | CCA | ACC | AAT | AAT | TTT | AAA | GAA | 3643 |
| Phe | Glu | Lys | Asn | Thr | Asn | Ile | Leu | Ile | Pro | Thr | Asn | Asn | Phe | Lys | Glu |      |
|     |     |     | 410 |     |     |     |     | 415 |     |     |     |     | 420 |     |     |      |
| GGT | TTT | GAA | TTT | TTA | TGG | GTT | CCA | ATT | GTT | AAT | GGT | ATT | GCT | TCA | ACT | 3691 |
| Gly | Phe | Glu | Phe | Leu | Trp | Val | Pro | Ile | Val | Asn | Gly | Ile | Ala | Ser | Thr |      |
|     |     | 425 |     |     |     |     | 430 |     |     |     |     | 435 |     |     |     |      |
| TCT | GTC | TTT | GTT | TCA | CCA | AAT | AAT | TAT | TCA | AGT | GGT | TCA | TTT | GCA | AAT | 3739 |
| Ser | Val | Phe | Val | Ser | Pro | Asn | Asn | Tyr | Ser | Ser | Gly | Ser | Phe | Ala | Asn |      |
|     | 440 |     |     |     |     | 445 |     |     |     |     | 450 |     |     |     |     |      |
| GTA | GAA | TCT | GCT | TTA | AAG | TTG | ATT | CAT | CTT | TGC | ATT | TCT | TTA | GGA | AAT | 3787 |
| Val | Glu | Ser | Ala | Leu | Lys | Leu | Ile | His | Leu | Cys | Ile | Ser | Leu | Gly | Asn |      |
| 455 |     |     |     |     | 460 |     |     |     |     | 465 |     |     |     |     | 470 |      |
| ATA | AAT | GGT | TTC | CTC | TCT | ATT | AGA | TCA | ATT | ACA | TTT | GAT | ACA | TTT | AAA | 3835 |
| Ile | Asn | Gly | Phe | Leu | Ser | Ile | Arg | Ser | Ile | Thr | Phe | Asp | Thr | Phe | Lys |      |
|     |     |     |     | 475 |     |     |     |     | 480 |     |     |     |     | 485 |     |      |
| TCG | ATT | ACA | AAG | GAT | CTT | ATT | CCA | ATG | TCG | AAA | AGA | ATG | CTG | GAC | CTT | 3883 |
| Ser | Ile | Thr | Lys | Asp | Leu | Ile | Pro | Met | Ser | Lys | Arg | Met | Leu | Asp | Leu |      |
|     |     |     | 490 |     |     |     |     | 495 |     |     |     |     | 500 |     |     |      |
| GAA | CAA | GGC | TTC | CGA | AAA | CTT | AGA | GAT | GCT | TGG | AAT | AAT | AGT | AAT | AAA | 3931 |
| Glu | Gln | Gly | Phe | Arg | Lys | Leu | Arg | Asp | Ala | Trp | Asn | Asn | Ser | Asn | Lys |      |
|     |     | 505 |     |     |     |     | 510 |     |     |     |     | 515 |     |     |     |      |
| AAA | TCC | AAA | GTT | CAA | GAT | AGT | GAT | ATT | AGT | GGC | ATC | GAT | ACA | GAG | GAT | 3979 |
| Lys | Ser | Lys | Val | Gln | Asp | Ser | Asp | Ile | Ser | Gly | Ile | Asp | Thr | Glu | Asp |      |
|     | 520 |     |     |     |     | 525 |     |     |     |     | 530 |     |     |     |     |      |
| ACA | AAG | TTG | ATA | TCA | TTT | GTC | CAC | GAG | TTT | ATA | AAT | GAT | AAT | TTA | TAT | 4027 |
| Thr | Lys | Leu | Ile | Ser | Phe | Val | His | Glu | Phe | Ile | Asn | Asp | Asn | Leu | Tyr |      |
| 535 |     |     |     |     | 540 |     |     |     |     | 545 |     |     |     |     | 550 |      |
| TTA | AAA | CTA | TCA | AAA | GAA | GAA | GAT | GGA | CTA | ATG | CTA | GTA | GAC | TTT | CCA | 4075 |
| Leu | Lys | Leu | Ser | Lys | Glu | Glu | Asp | Gly | Leu | Met | Leu | Val | Asp | Phe | Pro |      |
|     |     |     |     | 555 |     |     |     |     | 560 |     |     |     |     | 565 |     |      |
| ACA | TCA | ACA | CTT | TTT | ATG | AGA | TAC | AAT | CCA | AAT | AGC | ATT | GAT | AAC | AAA | 4123 |
| Thr | Ser | Thr | Leu | Phe | Met | Arg | Tyr | Asn | Pro | Asn | Ser | Ile | Asp | Asn | Lys |      |
|     |     |     | 570 |     |     |     |     | 575 |     |     |     |     | 580 |     |     |      |
| GTT | GGT | TTC | ATG | TTC | CAT | TGC | CGT | TCA | GAG | ATT | TCA | AAG | TTT | CAA | AGT | 4171 |
| Val | Gly | Phe | Met | Phe | His | Cys | Arg | Ser | Glu | Ile | Ser | Lys | Phe | Gln | Ser |      |
|     |     |     | 585 |     |     |     |     | 590 |     |     |     |     | 595 |     |     |      |
| TGT | AAA | AAC | CAC | TCG | ATA | GAT | AAC | CTT | GTT | TTA | TCA | TTT | ACT | CCA | AAT | 4219 |
| Cys | Lys | Asn | His | Ser | Ile | Asp | Asn | Leu | Val | Leu | Ser | Phe | Thr | Pro | Asn |      |
| 600 |     |     |     |     | 605 |     |     |     |     | 610 |     |     |     |     |     |      |
| AAC | ATT | AAA | AAT | ATA | TCA | CAG | GAT | AAT | GAA | AAT | GAG | CTT | AAA | AAG | AAA | 4267 |
| Asn | Ile | Lys | Asn | Ile | Ser | Gln | Asp | Asn | Glu | Asn | Glu | Leu | Lys | Lys | Lys |      |
| 615 |     |     |     |     | 620 |     |     |     |     | 625 |     |     |     |     | 630 |      |
| TAT | TCG | TTG | ATG | GTC | AGT | GAT | TTT | AGA | AAT | GTT | CCA | AAG | GTG | ACA | CCA | 4315 |
| Tyr | Ser | Leu | Met | Val | Ser | Asp | Phe | Arg | Asn | Val | Pro | Lys | Val | Thr | Pro |      |
|     |     |     |     | 635 |     |     |     |     | 640 |     |     |     |     | 645 |     |      |
| AAA | TTT | ATA | CCT | TCT | GAA | TTT | AAA | AGG | TTT | ACA | ATC | ATT | ACG | TTC | ACA | 4363 |
| Lys | Phe | Ile | Pro | Ser | Glu | Phe | Lys | Arg | Phe | Thr | Ile | Ile | Thr | Phe | Thr |      |
|     |     |     | 650 |     |     |     |     | 655 |     |     |     |     | 660 |     |     |      |
| AAC | AAT | TCA | TAC | AAT | GCC | AAT | AGA | GTA | TTT | GCG | TTT | GAC | GAC | ATC | TCA | 4411 |
| Asn | Asn | Ser | Tyr | Asn | Ala | Asn | Arg | Val | Phe | Ala | Phe | Asp | Asp | Ile | Ser |      |
|     |     | 665 |     |     |     |     | 670 |     |     |     |     | 675 |     |     |     |      |

```
AGT GGA ATT TCA ATC ACA AAT GTT AAA AAT ATC CAC GCA AAG GGT CAA    4459
Ser Gly Ile Ser Ile Thr Asn Val Lys Asn Ile His Ala Lys Gly Gln
        680                 685                 690

CGA AAC TTT GAA ATC TAC GAA ACA TTA CTG GGA AGT ACC AGG ATT ATT    4507
Arg Asn Phe Glu Ile Tyr Glu Thr Leu Leu Gly Ser Thr Arg Ile Ile
695                 700                 705                 710

CGT GCA TTT TTC TGC GCT CCA TGC TTG ATC CAA ATC AAT AAT TTT AAA    4555
Arg Ala Phe Phe Cys Ala Pro Cys Leu Ile Gln Ile Asn Asn Phe Lys
                715                 720                 725

TTT GCC ACA GAT AAG TTA ATT GAT GAC CAA AGT GTA AAT CAC CAG ATT    4603
Phe Ala Thr Asp Lys Leu Ile Asp Asp Gln Ser Val Asn His Gln Ile
            730                 735                 740

GCA TCT TTG GAA ATT AAA AAC TTA TCA TAT CTT CCG CTC GAC ATC AAG    4651
Ala Ser Leu Glu Ile Lys Asn Leu Ser Tyr Leu Pro Leu Asp Ile Lys
        745                 750                 755

GTT AGA GGT AGT ACA GTT GGA ACG ATT AAG GGT GGA GAG ACA GCT CCT    4699
Val Arg Gly Ser Thr Val Gly Thr Ile Lys Gly Gly Glu Thr Ala Pro
    760                 765                 770

ATT ATT ATA AAC TCA GAA GAA TTT ACG TTT TCT ATC TCA TGC CTT GAT    4747
Ile Ile Ile Asn Ser Glu Glu Phe Thr Phe Ser Ile Ser Cys Leu Asp
775                 780                 785                 790

ATT AGA TTT AGT GCA TCC TTA ATT TCT AAA ACA AAA CTA AGC CAA CTT    4795
Ile Arg Phe Ser Ala Ser Leu Ile Ser Lys Thr Lys Leu Ser Gln Leu
                795                 800                 805

CCA ACA TTT GCT CCA GAT GAA AGG TAC AAT AAA GAG ACT AAC ATT TTA    4843
Pro Thr Phe Ala Pro Asp Glu Arg Tyr Asn Lys Glu Thr Asn Ile Leu
            810                 815                 820

AAA GTT TTG GAT CAA TGT GAT GAA CTT ACT CGA ACG TTT TTA AAT AAC    4891
Lys Val Leu Asp Gln Cys Asp Glu Leu Thr Arg Thr Phe Leu Asn Asn
        825                 830                 835

TAT AAA ATA GCT AAT AAA CTA TCA ACC ATT GAA AAT TAT TTA TAT AAT    4939
Tyr Lys Ile Ala Asn Lys Leu Ser Thr Ile Glu Asn Tyr Leu Tyr Asn
    840                 845                 850

AAT TTT ATG GGA CTA GAA GAT GAA GAT GAA GAT GAA GAT GAA GAT GAA    4987
Asn Phe Met Gly Leu Glu Asp Glu Asp Glu Asp Glu Asp Glu Asp Glu
855                 860                 865                 870

GAT GAA GAT GAA GAT GAA GAT GAA GAT GAA GAT GAA GAC GAA GAT GGG    5035
Asp Glu Asp Glu Asp Glu Asp Glu Asp Glu Asp Glu Asp Glu Asp Gly
                875                 880                 885

TAT TGAATTATCA TACTTTAAAA ATTAATTAAA TAAATAAAAA AAAAAAAATG         5088
Tyr

ATTTCAATTT AAATATATAC ATATATATAT ATATAAAATG AGATTAATAA AACTTTTGAG  5148

ACCAACATTT AATGAGATTT CTGATGCTGT TTATTTTGCC TGGAATGAGA GCAAAAGGCT  5208

AAAAAACATG AGAGAGAATA TAATAATAAA GGAAAACTTG GGAAAAAGGA TCTAGTATCC  5268

ATTTCCATAT TAATCCGTGC AGTACTATTA ATTAAAAAAA TACTTTAAAA AAAATTTTAA  5328

AAACATGGAA AATTATATAG ATCGATAGAT CACTAATTTT TAAAATTAAA TATATTAAAT  5388

TTATAAAAAT TGAAGTTCAT CAAGATATAT AGATAATTAT TTAATTATTT GAATTTTAA   5448

AAAAAAAAAA AAAAAAAAAA AAAAAATCAA ATATGTTTAT TGTTTAAGA TTTTTTAATC   5508

TCGTCAATGA TTTTAAAATA AAAATCGATA CATAATTTTA AAAAAACCC TTTACATTTT   5568

TTATTTTAAT TCCAAATTTA TACATTTTTT ATTTTTTTT TTTTTTTTT TTTTTTTTT    5628

AATTTAAATT TTTTTTTTTT TTTTTTTTTT ATTTATTTAA AATTTAATTA TTAATTTTAT  5688

AAATAAAAAA TAGAAATATA AGTAAAAAAA CAAACAACAA ATAACATATA TAAAAAAATA  5748

CAAATAACAA ATAATTAAAT AAAATTAAATA ACCATTAAAA ATGTATATTA ATAAATTTAA 5808

AAGATCTTTA TTAGTACTAT TGTTACTTTG TAATATTCTT CCTG                   5852
```

( 2 ) INFORMATION FOR SEQ ID NO:3:

( i ) SEQUENCE CHARACTERISTICS:
        ( A ) LENGTH: 887 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Asp  Glu  Leu  Ile  Ser  Trp  Asp  Arg  Phe  Phe  Lys  Phe  Phe  Val  Ile
 1              5                        10                      15

Leu  Leu  Glu  Glu  Phe  Lys  Gly  Cys  Lys  Arg  Asn  Asp  Val  Arg  Leu  Ser
                20                       25                      30

Val  Asp  Tyr  Asp  Ile  Leu  Ser  Gly  Ile  Tyr  Ser  Pro  Arg  Thr  Phe  Val
           35                       40                      45

Leu  Lys  Glu  Val  Phe  Arg  Ala  Val  Ala  Val  Ser  Tyr  Asp  Glu  Ser  Glu
      50                       55                      60

Ile  Asp  Leu  Phe  Arg  Leu  Gly  Ser  Val  Phe  Pro  Gly  Thr  Ser  Leu  Tyr
 65                       70                      75                           80

Ser  Tyr  Ile  Pro  Gly  Ile  Phe  Ser  Leu  Lys  Asp  Phe  Leu  Leu  Ile  Ser
                85                       90                      95

Lys  Thr  Lys  Ser  Gly  Lys  Ile  Arg  Val  Ser  Asp  Val  Asp  Gln  Ala  Ile
               100                      105                     110

Leu  Ile  Phe  Asp  His  Phe  Ser  Arg  Ile  Ser  Asp  Lys  Gln  Val  Phe  Arg
              115                       120                     125

Lys  Asp  Ile  Ile  Pro  Gly  Tyr  Arg  Thr  Phe  Glu  Lys  Ser  Ile  Ser  Ser
          130                       135                     140

Glu  Tyr  Lys  Ile  Ser  Asp  Gly  Arg  Ala  Ala  Gly  Val  Ser  Trp  Phe  Asn
145                       150                      155                     160

Leu  Val  Ser  Lys  Ile  Ser  Thr  Tyr  Cys  Lys  Asn  His  Pro  Leu  Phe  Ala
                165                      170                     175

Glu  Asn  Pro  Thr  Tyr  Lys  His  Val  Asp  Phe  Ile  Ser  Met  Leu  Ser  Leu
               180                      185                     190

Val  His  Gly  Ile  Ile  Val  Asp  Ser  Gln  Asn  Glu  Asp  Glu  Asn  Asn  Val
              195                      200                     205

Ser  Ala  Met  Tyr  Ser  Leu  Asn  Pro  Phe  Val  Asp  Leu  Glu  Lys  Ser  Asp
          210                      215                     220

Ile  Pro  Gly  Ala  Val  Gln  Ser  Arg  Val  Thr  Thr  Asn  Arg  Thr  Arg  Gly
225                       230                      235                     240

Ser  Arg  Ser  Asn  Ser  Asn  Leu  Asn  Asn  Pro  Thr  Thr  Thr  Thr  Thr  Thr
                245                      250                     255

Thr  Thr  Thr  Thr  Thr  Thr  Thr  Ala  Pro  Ile  Thr  Thr  Arg  Ser  Lys  Arg
               260                      265                     270

Lys  Ser  Asp  Asp  Ser  Val  Gln  Glu  Gln  Ser  Ser  Arg  Gln  Pro  Lys  Thr
          275                      280                     285

Ser  Arg  Lys  Ser  Gly  Ser  Leu  Lys  Asp  Val  Arg  Ile  Asn  Asn  Ile  Ser
     290                      295                      300

Val  Asp  Ser  Ser  Ser  Ser  Glu  Ser  Asp  Val  Ile  Met  Ser  Val  Ser  Asn
305                       310                      315                     320

Arg  Leu  Lys  Cys  Tyr  Leu  Leu  Glu  Ala  Val  Val  Asn  Lys  Gly  Glu  Ile
                325                      330                     335

Gly  Leu  Glu  Val  Val  Lys  Glu  Val  Leu  Lys  Asp  Leu  Gln  Asp  Lys  Asn
               340                      345                     350

Tyr  Ala  Thr  Gly  Leu  Leu  Glu  Asn  Ile  Phe  Asn  His  Asn  Lys  Ser  Glu
          355                      360                     365

Arg  Val  Ile  Thr  Leu  Ser  Ser  Ser  Phe  Phe  Glu  Ile  Ala  Ser  Lys  Ile
```

|     |     |     | 370 |     |     |     | 375 |     |     |     | 380 |     |     |     |
|-----|-----|-----|-----|-----|-----|-----|-----|-----|-----|-----|-----|-----|-----|-----|

Asn Tyr Asp Glu Val Lys Phe Ser Glu Leu Ser Ile Asp Val Leu Glu
385                 390                 395                 400

Ser Ala Lys Arg Leu Thr Phe Glu Lys Asn Thr Asn Ile Leu Ile Pro
            405                 410                 415

Thr Asn Asn Phe Lys Glu Gly Phe Glu Phe Leu Trp Val Pro Ile Val
            420                 425                 430

Asn Gly Ile Ala Ser Thr Ser Val Phe Val Ser Pro Asn Asn Tyr Ser
        435                 440                 445

Ser Gly Ser Phe Ala Asn Val Glu Ser Ala Leu Lys Leu Ile His Leu
    450                 455                 460

Cys Ile Ser Leu Gly Asn Ile Asn Gly Phe Leu Ser Ile Arg Ser Ile
465                 470                 475                 480

Thr Phe Asp Thr Phe Lys Ser Ile Thr Lys Asp Leu Ile Pro Met Ser
            485                 490                 495

Lys Arg Met Leu Asp Leu Glu Gln Gly Phe Arg Lys Leu Arg Asp Ala
            500                 505                 510

Trp Asn Asn Ser Asn Lys Lys Ser Lys Val Gln Asp Ser Asp Ile Ser
            515                 520                 525

Gly Ile Asp Thr Glu Asp Thr Lys Leu Ile Ser Phe Val His Glu Phe
530                 535                 540

Ile Asn Asp Asn Leu Tyr Leu Lys Leu Ser Lys Glu Glu Asp Gly Leu
545                 550                 555                 560

Met Leu Val Asp Phe Pro Thr Ser Thr Leu Phe Met Arg Tyr Asn Pro
            565                 570                 575

Asn Ser Ile Asp Asn Lys Val Gly Phe Met Phe His Cys Arg Ser Glu
            580                 585                 590

Ile Ser Lys Phe Gln Ser Cys Lys Asn His Ser Ile Asp Asn Leu Val
        595                 600                 605

Leu Ser Phe Thr Pro Asn Asn Ile Lys Asn Ile Ser Gln Asp Asn Glu
    610                 615                 620

Asn Glu Leu Lys Lys Lys Tyr Ser Leu Met Val Ser Asp Phe Arg Asn
625                 630                 635                 640

Val Pro Lys Val Thr Pro Lys Phe Ile Pro Ser Glu Phe Lys Arg Phe
            645                 650                 655

Thr Ile Ile Thr Phe Thr Asn Asn Ser Tyr Asn Ala Asn Arg Val Phe
            660                 665                 670

Ala Phe Asp Asp Ile Ser Ser Gly Ile Ser Ile Thr Asn Val Lys Asn
        675                 680                 685

Ile His Ala Lys Gly Gln Arg Asn Phe Glu Ile Tyr Glu Thr Leu Leu
    690                 695                 700

Gly Ser Thr Arg Ile Ile Arg Ala Phe Phe Cys Ala Pro Cys Leu Ile
705                 710                 715                 720

Gln Ile Asn Asn Phe Lys Phe Ala Thr Asp Lys Leu Ile Asp Asp Gln
            725                 730                 735

Ser Val Asn His Gln Ile Ala Ser Leu Glu Ile Lys Asn Leu Ser Tyr
            740                 745                 750

Leu Pro Leu Asp Ile Lys Val Arg Gly Ser Thr Val Gly Thr Ile Lys
        755                 760                 765

Gly Gly Glu Thr Ala Pro Ile Ile Asn Ser Glu Phe Thr Phe
    770                 775                 780

Ser Ile Ser Cys Leu Asp Ile Arg Phe Ser Ala Ser Leu Ile Ser Lys
785                 790                 795                 800

Thr Lys Leu Ser Gln Leu Pro Thr Phe Ala Pro Asp Glu Arg Tyr Asn
            805                 810                 815

| Lys | Glu | Thr | Asn | Ile | Leu | Lys | Val | Leu | Asp | Gln | Cys | Asp | Glu | Leu | Thr |
|---|---|---|---|---|---|---|---|---|---|---|---|---|---|---|---|
| | | | 820 | | | | 825 | | | | | 830 | | | |

| Arg | Thr | Phe | Leu | Asn | Asn | Tyr | Lys | Ile | Ala | Asn | Lys | Leu | Ser | Thr | Ile |
|---|---|---|---|---|---|---|---|---|---|---|---|---|---|---|---|
| | | 835 | | | | 840 | | | | | 845 | | | | |

| Glu | Asn | Tyr | Leu | Tyr | Asn | Asn | Phe | Met | Gly | Leu | Glu | Asp | Glu | Asp | Glu |
|---|---|---|---|---|---|---|---|---|---|---|---|---|---|---|---|
| | 850 | | | | | 855 | | | | | 860 | | | | |

| Asp | Glu | Asp | Glu | Asp | Glu | Asp | Glu | Asp | Glu | Asp | Glu | Asp | Glu | Asp | Glu |
|---|---|---|---|---|---|---|---|---|---|---|---|---|---|---|---|
| 865 | | | | | 870 | | | | 875 | | | | | | 880 |

| Asp | Glu | Asp | Glu | Asp | Gly | Tyr |
|---|---|---|---|---|---|---|
| | | | | 885 | | |

( 2 ) INFORMATION FOR SEQ ID NO:4:

( i ) SEQUENCE CHARACTERISTICS:
( A ) LENGTH: 3138 base pairs
( B ) TYPE: nucleic acid
( C ) STRANDEDNESS: single
( D ) TOPOLOGY: circular ( i i ) MOLECULE TYPE: DNA (genomic)

( i v ) ANTI-SENSE: NO ( x i ) SEQUENCE DESCRIPTION: SEQ ID NO:4:

| | | | | | |
|---|---|---|---|---|---|
| CGATAGGTGG | CACTTTTCGG | GGAAATGTGC | GCGGACCCC | TATTTGTTTA | TTTTTCTAAA | 60
| TACATTCAAA | TATGTATCCG | CTCATGAGAC | AATAACCCTG | ATAAATGCTT | CAATAATATT | 120
| GAAAAAGGAA | GAGTATGAGT | ATTCAACATT | TCCGTGTCGC | CCTTATTCCC | TTTTTTGCGG | 180
| CATTTTGCCT | TCCTGTTTTT | GCTCACCCAG | AAACGCTGGT | GAAAGTAAAA | GATGCTGAAG | 240
| ATCAGTTGGG | TGCACGAGTG | GGTTACATCG | AACTGGATCT | CAACAGCGGT | AAGATCCTTG | 300
| AGAGTTTTCG | CCCCGAAGAA | CGTTTTCCAA | TGATGAGCAC | TTTTAAAGTT | CTGCTATGTG | 360
| GCGCGGTATT | ATCCCGTATT | GACGCCGGGC | AAGAGCAACT | CGGTCGCCGC | ATACACTATT | 420
| CTCAGAATGA | CTTGGTTGAG | TACTCACCAG | TCACAGAAAA | GCATCTTACG | GATGGCATGA | 480
| CAGTAAGAGA | ATTATGCAGT | GCTGCCATAA | CCATGAGTGA | TAACACTGCG | GCCAACTTAC | 540
| TTCTGACAAC | GATCGGAGGA | CCGAAGGAGC | TAACCGCTTT | TTTGCACAAC | ATGGGGGATC | 600
| ATGTAACTCG | CCTTGATCGT | TGGGAACCGG | AGCTGAATGA | AGCCATACCA | AACGACGAGC | 660
| GTGACACCAC | GATGCCTGTA | GCAATGCCAA | CAACGTTGCG | CAAACTATTA | ACTGGCGAAC | 720
| TACTTACTCT | AGCTTCCCGG | CAACAATTAA | TAGACTGGAT | GGAGGCGGAT | AAAGTTGCAG | 780
| GACCACTTCT | GCGCTCGGCC | CTTCCGGCTG | GCTGGTTTAT | TGCTGATAAA | TCTGGAGCCG | 840
| GTGAGCGTGG | GTCTCGCGGT | ATCATTGCAG | CACTGGGGCC | AGATGGTAAG | CCCTCCCGTA | 900
| TCGTAGTTAT | CTACACGACG | GGGAGTCAGG | CAACTATGGA | TGAACGAAAT | AGACAGATCG | 960
| CTGAGATAGG | TGCCTCACTG | ATTAAGCATT | GGTAACTGTC | AGACCAAGTT | TACTCATATA | 1020
| TACTTTAGAT | TGATTTAAAA | CTTCATTTTT | AATTTAAAAG | GATCTAGGTG | AAGATCCTTT | 1080
| TTGATAATCT | CATGACCAAA | ATCCCTTAAC | GTGAGTTTTC | GTTCCACTGA | GCGTCAGACC | 1140
| CCGTAGAAAA | GATCAAAGGA | TCTTCTTGAG | ATCCTTTTTT | TCTGCGCGTA | ATCTGCTGCT | 1200
| TGCAAACAAA | AAAACCACCG | CTACCAGCGG | TGGTTTGTTT | GCCGGATCAA | GAGCTACCAA | 1260
| CTCTTTTTCC | GAAGGTAACT | GGCTTCAGCA | GAGCGCAGAT | ACCAAATACT | GTCCTTCTAG | 1320
| TGTAGCCGTA | GTTAGGCCAC | CACTTCAAGA | ACTCTGTAGC | ACCGCCTACA | TACCTCGCTC | 1380
| TGCTAATCCT | GTTACCAGTG | GCTGCTGCCA | GTGGCGATAA | GTCGTGTCTT | ACCGGGTTGG | 1440
| ACTCAAGACG | ATAGTTACCG | GATAAGGCGC | AGCGGTCGGG | CTGAACGGGG | GGTTCGTGCA | 1500
| CACAGCCCAG | CTTGGAGCGA | ACGACCTACA | CCGAACTGAG | ATACCTACAG | CGTGAGCTAT | 1560

-continued

```
GAGAAAGCGC CACGCTTCCC GAAGGGAGAA AGGCGGACAG GTATCCGGTA AGCGGCAGGG      1620
TCGGAACAGG AGAGCGCACG AGGGAGCTTC CAGGGGAAA  CGCCTGGTAT CTTTATAGTC      1680
CTGTCGGGTT TCGCCACCTC TGACTTGAGC GTCGATTTTT GTGATGCTCG TCAGGGGGGC      1740
GGAGCCTATC GAAAACGCC  AGCAACGCGG CCTTTTACG  GTTCCTGGCC TTTTGCTGGC      1800
CTTTTGCTGG CCTTTGGATC TACAAATTAA TTAATCCCAT CAAATCTTTA AAAAAAAAA      1860
TGGTTTAAAA AAACTTGGGT TGGTTAATTA TTATTTGAAA ATTTTAAAAC CCAAATTAAA      1920
AAAAAAAAT  GGGATTCAAA AATTTTTTTT TTTTTTTTT  TTTTTTTTT  TTTTTTTTT      1980
TTTTTTTCA  GATTGCATAA AAAGATTTTT TTTTTTTTT  TTTCTTATTT CTTAAAACAA      2040
ATAAATTAAA TTAAATAAAA AATAAAAATG AAATTCCAAC ATACATTTAT TGCATTATTA      2100
TCACTATTAA CATACGCCAA TGCATATGAA AGCTTGCATG CCTGCAGGTC GACTCTAGAG      2160
GATCCCCGGG TACCTAAATC ATGAATGAAA GTGCTTCACA TAAAATAAT  AATAATAATA      2220
TAACAATAAT AATATTTAAA TGTATAATAA AATTTAATTA CTTTTTTTT  AATGGTTGTT      2280
GATCTTTATC CGACCTTAAA AAAAAAAAA  TAAACCAAT  AGGCTATTGG TTTTTTTTT      2340
AATTGTTTTT TTATTTTTA  TTATTACTTT AATTATCATT TTTTAAATTA CAAAAAAAT      2400
TAAAAATCCA GATATTAAGG TATTTGCACT AGTGCTTTAA CGTTAAAATT TGAAAAAAAA      2460
AAAAATTAA  TAATTTTACC CTTTATGGGT AAACGATTCT CACATATAAT ACAATCTCCA      2520
TGAAAAGATC CGCTAGACGA GCACAAATAT ATACTTTTA  TTAAAAACGG AGGTCATTTC      2580
AATACCTATT GAAGAAATAA ATTTTTTTTT TTTTTTTT   TGTCATGACA CTTTTTTTT      2640
TTTGTCATGA CAGAATTGAA AAAACAGAA  AGTTATATAT TTACCCCCTT TAATTTTTT      2700
TAAAACTTTT GAAACTTTAG TAATAAGATC GATCTATACT TCAGTACGAA CATAAATATG      2760
TATAAACCAA AAAATTGAT  TAAGATAAAG TTATATGTTT GTATTTAATA AATAGTTTA      2820
GTTTAAAATT TTATATCATT TTTTAAAAAA TGAAATGTT  TGAAAAAAAA AATTTTTTT      2880
TTTTTTTCA  ACGGGACGAT GTAATATCAT ATATGATTCA AAATTAAAAG TTATTAACAA      2940
ATATGTAAAA ATTATAAAAA ACTAACCTAG TTATAATTAC TTTCCCTCT  TTTTTTTTT      3000
TTTTTTGTC  ATGACACTTT TTTTTTTTG  TCATGACACT TTTTTTTAA  AAAAAAAAA      3060
AAAAATGTTA AATACTATT  TGATGACATT CATTTTCCT  AGTTTTTTT  TAGATAGATA      3120
TAAAAATAAA TTGCCTAT                                                    3138
```

( 2 ) INFORMATION FOR SEQ ID NO:5:

( i ) SEQUENCE CHARACTERISTICS:
        ( A ) LENGTH: 2422 base pairs
        ( B ) TYPE: nucleic acid
        ( C ) STRANDEDNESS: single
        ( D ) TOPOLOGY: circular ( i i ) MOLECULE TYPE: DNA (genomic)

( i v ) ANTI-SENSE: NO ( x i ) SEQUENCE DESCRIPTION: SEQ ID NO:5:

```
CGATAGGTGG CACTTTTCGG GGAAATGTGC GCGGAACCCC TATTTGTTTA TTTTTCTAAA        60
TACATTCAAA TATGTATCCG CTCATGAGAC AATAACCCTG ATAAATGCTT CAATAATATT       120
GAAAAAGGAA GAGTATGAGT ATTCAACATT TCCGTGTCGC CCTTATTCCC TTTTTTGCGG       180
CATTTTGCCT TCCTGTTTTT GCTCACCCAG AAACGCTGGT GAAAGTAAAA GATGCTGAAG       240
ATCAGTTGGG TGCACGAGTG GGTTACATCG AACTGGATCT CAACAGCGGT AAGATCCTTG       300
AGAGTTTTCG CCCCGAAGAA CGTTTTCCAA TGATGAGCAC TTTTAAAGTT CTGCTATGTG       360
```

| | | | | | | |
|---|---|---|---|---|---|---|
| GCGCGGTATT | ATCCCGTATT | GACGCCGGGC | AAGAGCAACT | CGGTCGCCGC | ATACACTATT | 420 |
| CTCAGAATGA | CTTGGTTGAG | TACTCACCAG | TCACAGAAAA | GCATCTTACG | GATGGCATGA | 480 |
| CAGTAAGAGA | ATTATGCAGT | GCTGCCATAA | CCATGAGTGA | TAACACTGCG | GCCAACTTAC | 540 |
| TTCTGACAAC | GATCGGAGGA | CCGAAGGAGC | TAACCGCTTT | TTTGCACAAC | ATGGGGATC | 600 |
| ATGTAACTCG | CCTTGATCGT | TGGGAACCGG | AGCTGAATGA | AGCCATACCA | AACGACGAGC | 660 |
| GTGACACCAC | GATGCCTGTA | GCAATGCCAA | CAACGTTGCG | CAAACTATTA | ACTGGCGAAC | 720 |
| TACTTACTCT | AGCTTCCCGG | CAACAATTAA | TAGACTGGAT | GGAGGCGGAT | AAAGTTGCAG | 780 |
| GACCACTTCT | GCGCTCGGCC | CTTCCGGCTG | GCTGGTTTAT | TGCTGATAAA | TCTGGAGCCG | 840 |
| GTGAGCGTGG | GTCTCGCGGT | ATCATTGCAG | CACTGGGGCC | AGATGGTAAG | CCCTCCCGTA | 900 |
| TCGTAGTTAT | CTACACGACG | GGGAGTCAGG | CAACTATGGA | TGAACGAAAT | AGACAGATCG | 960 |
| CTGAGATAGG | TGCCTCACTG | ATTAAGCATT | GGTAACTGTC | AGACCAAGTT | TACTCATATA | 1020 |
| TACTTTAGAT | TGATTTAAAA | CTTCATTTTT | AATTTAAAAG | GATCTAGGTG | AAGATCCTTT | 1080 |
| TTGATAATCT | CATGACCAAA | ATCCCTTAAC | GTGAGTTTTC | GTTCCACTGA | GCGTCAGACC | 1140 |
| CCGTAGAAAA | GATCAAAGGA | TCTTCTTGAG | ATCCTTTTTT | TCTGCGCGTA | ATCTGCTGCT | 1200 |
| TGCAAACAAA | AAACCACCG | CTACCAGCGG | TGGTTTGTTT | GCCGGATCAA | GAGCTACCAA | 1260 |
| CTCTTTTTCC | GAAGGTAACT | GGCTTCAGCA | GAGCGCAGAT | ACCAAATACT | GTCCTTCTAG | 1320 |
| TGTAGCCGTA | GTTAGGCCAC | CACTTCAAGA | ACTCTGTAGC | ACCGCCTACA | TACCTCGCTC | 1380 |
| TGCTAATCCT | GTTACCAGTG | GCTGCTGCCA | GTGGCGATAA | GTCGTGTCTT | ACCGGGTTGG | 1440 |
| ACTCAAGACG | ATAGTTACCG | GATAAGGCGC | AGCGGTCGGG | CTGAACGGGG | GGTTCGTGCA | 1500 |
| CACAGCCCAG | CTTGGAGCGA | ACGACCTACA | CCGAACTGAG | ATACCTACAG | CGTGAGCTAT | 1560 |
| GAGAAAGCGC | CACGCTTCCC | GAAGGGAGAA | AGGCGGACAG | GTATCCGGTA | AGCGGCAGGG | 1620 |
| TCGGAACAGG | AGAGCGCACG | AGGGAGCTTC | CAGGGGGAAA | CGCCTGGTAT | CTTTATAGTC | 1680 |
| CTGTCGGGTT | TCGCCACCTC | TGACTTGAGC | GTCGATTTTT | GTGATGCTCG | TCAGGGGGGC | 1740 |
| GGAGCCTATC | GAAAACGCC | AGCAACGCGG | CCTTTTTACG | GTTCCTGGCC | TTTTGCTGGC | 1800 |
| CTTTTGCTGG | CCTTTGGATC | CGCTAGACGA | GCACAAATAT | ATACTTTTA | TTAAAAACGG | 1860 |
| AGGTCATTTC | AATACCTATT | GAAGAAATAA | ATTTTTTTTT | TTTTTTTTT | TGTCATGACA | 1920 |
| CTTTTTTTTT | TTTGTCATGA | CAGAATTGAA | AAAACAGAA | AGTTATATAT | TTACCCCCTT | 1980 |
| TAATTTTTTT | TAAAACTTTT | GAAACTTTAG | TAATAAGATC | TATACTTCAG | TACGAACATA | 2040 |
| AATATGTATA | AACCAAAAAA | ATTGATTAAG | ATAAAGTTAT | ATGTTTGTAT | TTAATAAAAT | 2100 |
| AGTTTAGTTT | AAAATTTTAT | ATCATTTTTT | AAAAAATGAA | AATGTTTGAA | AAAAAAATT | 2160 |
| TTTTTTTTTT | TTTTCAACGG | GACGATGTAA | TATCATATGA | TTCAAAATTA | AAAGTTATTA | 2220 |
| ACAAATATGT | AAAAATTATA | AAAACTAAC | CTAGTTATAA | TTACTTTCCC | CTCTTTTTTT | 2280 |
| TTTTTTTTTT | TGTCATGACA | CTTTTTTTTT | TTTGTCATGA | CACTTTTTTT | TTAAAAAAAA | 2340 |
| AAAAAAAAAT | GTTAAAATAC | TATTTGATGA | CATTCATTTT | TCCTAGTTTT | TTTTAGATA | 2400 |
| GATATAAAAA | TAAATTGCCT | AT | | | | 2422 |

( 2 ) INFORMATION FOR SEQ ID NO:6:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( i v ) ANTI-SENSE: NO ( x i ) SEQUENCE DESCRIPTION: SEQ ID NO:6:

TTTTTGTCA TGACACTTTT TTTTTTTGT CATGACA 37

( 2 ) INFORMATION FOR SEQ ID NO:7:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:7:

GGAGGGATCC AAAGGCCAGC AAAAGGCCAG CAAAAGGC 38

( 2 ) INFORMATION FOR SEQ ID NO:8:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:8:

GGGGTGGATC CGCTAGCCGC ATCGATAGGT GGCACTTTTC GG 42

( 2 ) INFORMATION FOR SEQ ID NO:9:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:9:

GAAGCATTTA TCAGGG 16

( 2 ) INFORMATION FOR SEQ ID NO:10:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:10:

TGGCCAAGCT TAGATCTACA AATTAATTAA TCCC 34

( 2 ) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:11:

CCCGGGATGT TCACCATGCA TTTTTATTTT TTA    33

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:12:

GGGAAGCTTG GATGAATTCA AAAAATGAAA TTCCAACAT    39

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:13:

CCCGGGTCGA CCTGCTATTG CATTTGCATA TGTTAA    36

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:14:

CACGCCAATG CATATGAAAG CT    22

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: NO ( x i ) SEQUENCE DESCRIPTION: SEQ ID NO:15:

TAAGCTTTCA TATGCATTGG CG    22

( 2 ) INFORMATION FOR SEQ ID NO:16:

( i ) SEQUENCE CHARACTERISTICS:
        ( A ) LENGTH: 31 base pairs
        ( B ) TYPE: nucleic acid (C) STRANDEDNESS: single
                (D) TOPOLOGY: linear (ii) MOLECULE TYPE: DNA (genomic)

(iv) ANTI-SENSE: NO (xi) SEQUENCE DESCRIPTION: SEQ ID NO:16:

TGCCGGTACC TAAATCATGA ATGAAAGTGC T                                              31

(2) INFORMATION FOR SEQ ID NO:17:

(i) SEQUENCE CHARACTERISTICS:
                (A) LENGTH: 34 base pairs
                (B) TYPE: nucleic acid
                (C) STRANDEDNESS: single
                (D) TOPOLOGY: linear (ii) MOLECULE TYPE: DNA (genomic)

(iv) ANTI-SENSE: NO (xi) SEQUENCE DESCRIPTION: SEQ ID NO:17:

CCCGGGAATT CAGATCTTTT CATGGAGATT GTAT                                           34

(2) INFORMATION FOR SEQ ID NO:18:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(iv) ANTI-SENSE: NO (xi) SEQUENCE DESCRIPTION: SEQ ID NO:18:

AATTCCCGGG                                                                      10

(2) INFORMATION FOR SEQ ID NO:19:

(i) SEQUENCE CHARACTERISTICS:
                (A) LENGTH: 66 base pairs
                (B) TYPE: nucleic acid
                (C) STRANDEDNESS: single
                (D) TOPOLOGY: linear (ii) MOLECULE TYPE: DNA (genomic)

(iv) ANTI-SENSE: NO (xi) SEQUENCE DESCRIPTION: SEQ ID NO:19:

GATGAAGATG AAGATGAAGA TGAAGATGAA GATGAAGATG AAGATGAAGA TGAAGATGAA               60

GATGAA                                                                          66